United States Patent
Das Gupta et al.

(10) Patent No.: US 9,969,781 B2
(45) Date of Patent: May 15, 2018

(54) COMPOSITIONS AND METHODS TO TREAT CANCER WITH CPG RICH DNA AND CUPREDOXINS

(76) Inventors: Tapas Das Gupta, River Forest, IL (US); Ananda Chakrabarty, Villa Park, IL (US)

(*) Notice: Subject to any disclaimer, the term of this patent is extended or adjusted under 35 U.S.C. 154(b) by 0 days. days.

(21) Appl. No.: 13/230,055

(22) Filed: Sep. 12, 2011

(65) Prior Publication Data
US 2012/0014877 A1    Jan. 19, 2012

Related U.S. Application Data

(62) Division of application No. 11/950,165, filed on Dec. 4, 2007, now Pat. No. 8,017,749.

(60) Provisional application No. 60/872,471, filed on Dec. 4, 2006.

(51) Int. Cl.
| | | |
|---|---|---|
| C07K 14/195 | (2006.01) | |
| C07K 14/21 | (2006.01) | |
| A61K 38/00 | (2006.01) | |

(52) U.S. Cl.
CPC ............ C07K 14/195 (2013.01); C07K 14/21 (2013.01); *A61K 38/00* (2013.01)

(58) Field of Classification Search
CPC ...... C07K 14/21; C07K 14/195; C07K 14/22; A61K 38/164; A61K 38/00; C12N 15/113; C12N 15/115; C12N 15/111; C12N 15/62; C12N 15/117; C12N 15/625
See application file for complete search history.

(56) References Cited

U.S. PATENT DOCUMENTS

| | | | |
|---|---|---|---|
| 4,817,384 A | 4/1989 | Okumura et al. | |
| 5,281,704 A | 1/1994 | Love et al. | |
| 5,412,148 A | 5/1995 | Keana | |
| 5,417,959 A | 5/1995 | Wallace | |
| 5,520,904 A | 5/1996 | Nosco et al. | |
| 5,567,411 A | 10/1996 | Keana et al. | |
| 5,679,810 A | 10/1997 | Love et al. | |
| 5,760,191 A | 6/1998 | Snow et al. | |
| 5,801,228 A | 9/1998 | Hollister et al. | |
| 5,804,161 A | 9/1998 | Long et al. | |
| 6,011,029 A | 1/2000 | Ding et al. | |
| 6,383,500 B1 | 5/2002 | Wooley et al. | |
| 6,551,795 B1* | 4/2003 | Rubenfield et al. | 435/69.1 |
| 7,084,105 B2 | 8/2006 | Chakrabarty et al. | |
| 7,301,010 B2 | 11/2007 | Chakrabarty et al. | |
| 7,338,776 B2 | 3/2008 | Pozueta Romero et al. | |
| 7,381,701 B2 | 6/2008 | Chakrabarty et al. | |
| 7,491,394 B2 | 2/2009 | Chakrabarty et al. | |
| 7,511,117 B2 | 3/2009 | Chakrabarty et al. | |
| 7,517,684 B2* | 4/2009 | Rubenfield et al. | 435/325 |
| 7,556,810 B2 | 7/2009 | Mehta et al. | |
| 7,618,939 B2* | 11/2009 | Gupta et al. | 514/1.1 |
| 7,740,857 B2 | 6/2010 | Chakrabarty et al. | |
| 7,807,182 B2 | 10/2010 | Laal et al. | |
| 7,807,183 B2* | 10/2010 | Hong et al. | 424/249.1 |
| 7,888,468 B2 | 2/2011 | Chakrabarty et al. | |
| 8,017,749 B2* | 9/2011 | Das Gupta et al. | 536/23.1 |
| 8,124,055 B2* | 2/2012 | Mehta et al. | 424/9.1 |
| 8,158,574 B2* | 4/2012 | Das Gupta et al. | 514/1 |
| 8,206,685 B2* | 6/2012 | Chakrabarty et al. | 424/9.2 |
| 8,227,402 B2* | 7/2012 | Das Gupta et al. | 514/1 |
| 8,232,244 B2* | 7/2012 | Das Gupta et al. | 514/19.3 |
| 8,372,962 B2* | 2/2013 | Mehta et al. | 536/23.7 |
| 8,530,635 B2* | 9/2013 | Chakrabarty et al. | 536/23.1 |
| 8,623,816 B2* | 1/2014 | Chakrabarty et al. | 514/4.4 |
| 2003/0181406 A1 | 9/2003 | Schetter et al. | |
| 2006/0040269 A1 | 2/2006 | Chakrabarty et al. | |
| 2006/0149037 A1 | 7/2006 | Chakrabarty et al. | |
| 2006/0166923 A1 | 7/2006 | Ahn et al. | |
| 2006/0251639 A1 | 11/2006 | Chakrabarty et al. | |
| 2006/0251669 A1 | 11/2006 | Chakrabarty et al. | |
| 2006/0292136 A1 | 12/2006 | Chakrabarty et al. | |
| 2007/0020624 A1 | 1/2007 | Rubenfield et al. | |

(Continued)

FOREIGN PATENT DOCUMENTS

| | | |
|---|---|---|
| CN | 1506375 | 6/2004 |
| CN | 1526718 A | 9/2004 |

(Continued)

OTHER PUBLICATIONS

Spencer et al, Journal of Bacteriology, Feb. 2003, p. 1316-1325 vol. 185, No. 4.*
XP-002559082, Rubenfield et al.
XP-002559083, Rubenfield et al.
Yamada et al., Cell Cycle, (Sep. 200), 3/9:1182-1187.
Yamada et al., Cell Cycle, (Jun. 2004), 3/6: 752-755.
Fialho et al., Current Opinion in Biotechnology, (2007) 18: 279-2886.
Kwan et al, Leukemia Research (2009) 33: 1392-1399.
Spencer et al. J. Bacteriology (Feb. 2003), 185/4 : 1316-1325.
Mathee et al., PNAS, (Feb. 25, 2008) 105/8: 3100-3105.
Fialho et al., Recent Patents on Anti-Cancer Drug Discovery, (Nov. 2007) 2/3: 224-234.

(Continued)

*Primary Examiner* — Nita M Minnifield
(74) *Attorney, Agent, or Firm* — Benesch, Friedlander, Coplan & Aronoff LLP

(57) ABSTRACT

The present invention relates to compositions comprising CpG rich DNA from *Pseudomonas aeruginosa*. The compositions optionally comprise a cupredoxin. The present invention includes specific CpG DNAs from *Pseudomonas aeruginosa* that are useful for treating cancer and other conditions in patients. These compositions are optionally in a pharmaceutically acceptable carrier and also optionally comprise a cupredoxin. The present invention further relates to methods to express proteins near cancer cells. These methods may be used to express therapeutic or diagnostic proteins near cancer cells in a patient suffering from cancer or other conditions, and can also be used for diagnosing cancer in a patient. This method uses the gene for azurin from *P. aeruginosa* as an expression system for azurin or heterologous proteins in *P. aeruginosa* or heterologous cells.

8 Claims, 8 Drawing Sheets

(56) References Cited

U.S. PATENT DOCUMENTS

| | | |
|---|---|---|
| 2008/0089878 A1 | 4/2008 | Chakrabarty et al. |
| 2008/0103087 A1 | 5/2008 | Mehta et al. |
| 2008/0131873 A1 | 6/2008 | Chakrabarty et al. |
| 2008/0139471 A1 | 6/2008 | Das Gupta et al. |
| 2008/0182782 A1 | 7/2008 | Chakrabarty et al. |
| 2008/0213185 A1 | 9/2008 | Hong et al. |
| 2008/0221015 A1 | 9/2008 | Chaudhari et al. |
| 2008/0226560 A1 | 9/2008 | Das Gupta et al. |
| 2008/0293619 A1 | 11/2008 | Chakrabarty et al. |
| 2008/0312413 A1 | 12/2008 | Chakrabarty et al. |
| 2009/0202441 A1 | 8/2009 | Taylor et al. |
| 2009/0208476 A1 | 8/2009 | Das Gupta et al. |
| 2009/0215692 A1 | 8/2009 | Das Gupta et al. |
| 2009/0226405 A1 | 9/2009 | Das Gupta et al. |
| 2009/0286719 A1 | 11/2009 | Das Gupta et al. |
| 2010/0008919 A1 | 1/2010 | Mehta et al. |
| 2011/0077387 A1* | 3/2011 | Hong et al. ............. 536/23.2 |
| 2012/0014877 A1* | 1/2012 | Das Gupta et al. ............ 424/9.1 |
| 2012/0196805 A1* | 8/2012 | Mehta et al. ............. 514/13.3 |
| 2012/0302509 A1* | 11/2012 | Das Gupta et al. ............. 514/19.3 |
| 2013/0011338 A1* | 1/2013 | Chakrabarty et al. ....... 424/9.34 |
| 2013/0084247 A1* | 4/2013 | Das Gupta et al. ............. 424/9.34 |
| 2013/0087247 A1* | 4/2013 | Aehle et al. ............. 141/346 |
| 2013/0210731 A1* | 8/2013 | Mehta et al. ............. 514/13.3 |
| 2014/0037554 A1* | 2/2014 | Chakrabarty et al. ....... 424/9.34 |
| 2014/0051643 A1* | 2/2014 | Suri et al. ............. 514/19.4 |
| 2014/0056820 A1* | 2/2014 | Hong et al. ............. 424/9.34 |
| 2014/0234957 A1* | 8/2014 | Weiss et al. ............. 435/320.1 |
| 2014/0287990 A1* | 9/2014 | Das Gupta et al. ............ 514/3.8 |

FOREIGN PATENT DOCUMENTS

| | | |
|---|---|---|
| DE | 4138042 A1 | 5/1993 |
| EP | 0727225 A2 | 8/1996 |
| EP | 1997019086 | 5/1997 |
| EP | 1998022461 | 5/1998 |
| EP | 1999007692 | 2/1999 |
| EP | 1999065913 | 12/1999 |
| EP | 1999067252 | 12/1999 |
| WO | 9730992 | 8/1997 |
| WO | 9825929 | 6/1998 |
| WO | 9838192 | 9/1998 |
| WO | 9854966 | 10/1998 |
| WO | 9901124 | 1/1999 |
| WO | 9902224 | 1/1999 |
| WO | 9902514 | 1/1999 |
| WO | 9903848 | 1/1999 |
| WO | 9924416 | 5/1999 |
| WO | 9923324 | 6/1999 |
| WO | 9927890 | 6/1999 |
| WO | 9943653 | 9/1999 |
| WO | 9954318 | 10/1999 |
| WO | 9954319 | 10/1999 |
| WO | 9954330 | 10/1999 |
| WO | 9967253 | 12/1999 |
| WO | 0000485 | 6/2000 |
| WO | 2005018662 | 3/2005 |
| WO | 2006088508 | 8/2006 |
| WO | 2007012004 | 1/2007 |
| WO | 2007024368 | 3/2007 |
| WO | 2008033820 | 3/2008 |
| WO | 2008033987 | 3/2008 |
| WO | 2008070666 | 6/2008 |
| WO | 2008070672 | 6/2008 |
| WO | 2008098216 | 8/2008 |
| WO | 2009078977 | 6/2009 |

OTHER PUBLICATIONS

Canters et al., FEBS letters, (1987), 212: 168-172.
Beattie et al, 5th AACR International Conference on Frontiers in Cancer Prevention Research, Nov. 12-15, 2006, Abstract A217, abstract only.
Yang et al. Pharmacol. Res., (2005) 52413-421.
Donnelly et al. Nature Medicine, (2003) 9/11:1354-1356.
DeGruijl et al. Nature Medicine, (1999)5/10:2235-1125.
Bitton, Current Opinion in Molecular Therapeutics, (2004) 6/1:17-25.
Weiner, J. Leukoc. Biol., (2000) 68:455-463.
Ballas et al. J. Immunol., (2001) 167: 4878-4886.
Agrawal et al. Trends in Molecular Medicine, (2002) 8/3:114-120.
Neguj, et al., "Immunomodulation Activity 3-10 of a Pseudomonas Aeruginosa Extract—Cantastim", Archives Roumaines De Pathologie Experimentale Et Demicrobiologie, Cartimex, Bucharest, Ro. vol. 44, No. 4 pp. 323-335 (1985) XP002910004.
Krieg et al., "Mechanism of Action of CPG DNA" Current Topics in Microbiology and Immunology vol. 247 pp. 1-21 (2000) XP 001002250.
Charkrabarty et al., J. Bacterial. 185: 2683-2686 (2003).
Vassaux et al., J. Pathol. 208: 290-298.
Tokunaga et al. Japan J. Infect. Dis. 52 1-11 (1999).
Modlin, Nature 408: 659-660 (2000).
Krieg, Nature Med. 9:831-835 (2003).
Herman & Baylin, New Eng. J. Med. 349: 2042-2054.
Feinberg & Tyeko, Nature Rev. Cancer 4 143-153 (2004).
Wang et al. Oncogene 24: 2705-2714 (2005).
Ghadiri & Fernholz, J. Am. Chem. Soc. 112; 9633-9635 (1990).
Zaborina et al. Microbiology 146: 2521-2530 (2000).
Yamada et al. PNAS, 99: 14098-14103 (2002).
Punj et al. Oncogene 23: 2367-2378 (2004).
Yamada et al., Infection & Immunity 70: 7054-7062 (2002).
Kay et al., J. Bacterial., 188:6026-6033 (2006).
Minton, Nature Rev. Microbiol. 1: 237-243 (2003).
Dang et al., Cancer Biol. Therap. 3: 326-337.
Futaki et al. J. Biol. Chem. 276(8): 5836-5840 (2001).
Papa et al. Cancer Res. 64(16): 5779-5786 (2004).
Miller et al. Biochem Pharmacol. 36 (1): 169-176 (1987).
Lee et al., J. Pept. Res. 63 (2): 69-84 (2004).
Schafmeister et al. J. Am. Chem. Soc. 122: 2891-5892 (2000).
Monk et al. BioDrugs 19(4): 261-278 (2005).
Defreest et al., J. Pept. Res. 63(5): 409-419 (2004).
Toth et al., Developmental Cell 1: 82-92 (2001).
Kastakioti et al., J. Bacteriol. 187: 4306-4314 (2005).
Thanassi et al., Mol. Membr. Biol. 22: 63-72 (2005).
Goto et al., Mol. Microbiol. 47: 549-559 (2003).
Cascales & Christie, Nature Rev. Microbiol. 1: 137-149 (2003).
Burns, Curr. Opin. Microbiol. 2: 25-29 (1999).
Hamilton et al., Mol. Microbiol. 55: 1704-1721 (2005).
Delgado et al., Infect. Immun. 74: 2975-2984 (2006).
Whitechurch et al. Science 295: 1487 (2002).
Kievitz et al. Microbiol. 146: 2365-2373 (2000).
He et al. Proc. Natl. Acad. Sci. 101: 2530-2535 (2006).
Van Der Meer et al., Arch. Microbiol. 175: 79-85 (2001).
Liang et al., J. Bacteriol. 185: 843-853 (2001).
Hong et al., Cell Cycle 5: 1633-1641 (2006).
Krieg, Curr. Onco. Rep. 6: 88-95 (2006).
Kandimalla et al. Proc. Natl. Acad. Sci. 102: 6925-6930 (2005).
Wu, Infect. and Immun. 73 No. 12: 8444-8448 (2005).
Punj, Cancer Biol. and Therapy 3 Issue 8: 708-714 (2004).
Punj, Biochem. Res. Comm. 312: 109-114 (2003).
Mahfouz, Plasmid. 57: 4-17 (2007).
XP-002559081, Bode et al.
XP-002559084, Brodeur et al.
XP-002910004, Neguj et al.
XP-001002250, Krieg et al.
XP-002559080, Rubenfield et al.
Chinese Office Action Appl. No. 200780050577.1, dated Nov. 17, 2011.
Yamada, et al., Cellular Microbiology 7(10) pp. 1418-1431 (2005).
Office Action, dated Nov. 21, 2013, in Japanese Patent Application No. 2009-540425.
Padilla et al.: "Production of antimicrobial substances by hospital bacteria, active against other micro-organisms," J. Hospital Infection, vol. 49, pp. 43-47 (2001).
Oshikawa et al.: "Antitumor Effect of OK-432-Drived DNA," J. Immunotherapy, vol. 29, No. 2, pp. 143-150 (Mar./Apr. 2006).

\* cited by examiner

```
CTCCCCCCCCGACCGCCCTCCCGCCGCCGCCGGGTGCATGCTGCCGGTCGCTTCGC
CGGGCTCCCCGGCGCCCCCCCCCCCCTCCGCCCCCGCCGCCCCGCCGCTCCCTCTCCT
CACTCTCCCCCGCTCCCGCACCCTGTTCGCCCCGCCCCCGCGCCCCCCCGCCCCCCC
GCCCCCCCCATCTCTTCCCACCCCGGCCGCTCAGTTCTTAACCGTCAGCGGCTCA
CTGACCCCCAGCCCCACCCACCTCACTCCCCCCCCCCCAGGCCCCCACGCGCCTTCCC CCCCCATCCTTC
```

FIG. 5A

```
                  1              10              20              30              40              50              60
8822              LNHFGMQPKASIGHNIVFA.AEVLDGVFKDGVGAA.DTDYVKPDDARVVAHTKLIGGGEESSLTLDPAKL
NG                LKHTGTQPKASMGHNLVIAKAEDMDGVFKDGVGAA.DTDYVKPDDARVVAHTKLIGGGEESSLTLDPAKL
NM                LKHTGTQPKASMGHNLVIAKAEDMDGVFKDGVGAA.DTDYVKPDDARVVAHTKLIGGGEESSLTLDPAKL
PAO1              LISHPGNLPKNVMGHNMWVLSTAADMQGVVTDGMASGLDKDYLKPDDSRVIAHTKLIGSGEKDSVIFDVSKL
CONSENSUS>50      LkHtGtqPKasmGHNlViakAed$#GVfkDGvgaa.DtDYvKPDDaRV!AHTKLIGgGEesSlTlDpaKL 70              80              90
8822              ADGD.YKFACTFPGHGALTSSQV.....
NG                ADGD.YKFACTFPGHGALMNGKVTLVD
NM                ADGD.YKFACTFPGHGALMNGKVTLVD
PAO1              KEGEQXMFFCTFPGHSALMKGTLTLK.
CONSENSUS>50      a#G#.YkFaCTFPGHgALmngkvtlvd
```

FIG. 5B

| Clone# | Homology to known sequences | Identity % | Reference |
|---|---|---|---|
| 1 | PAO1 sequence section 523-529 | 99 | Stover et al (2000) |
| 2 | Bacteriophage F10 sequence | 94 | Kwan et al. (2006) |
| 3 | PAO Sub gene, a virulence determinant | 84 | Direct submission |
| 4 | In vivo induced gene important for survival | 61 | Direct submission |
| 5 | Bacteriophage F10 sequence | 96 | Kwan et al. (2006) |
| 6 | DNAJ, protein Chaperone | 57 | Direct submission |
| 7 | RNA dependent DNA polymerase, RT | 38 | Direct submission |
| 8 | Glutathione Spermidine Synthase | 59 | Direct submission |
| 9 | Neisseria gonorrhoeae azurin gene | 85 | Direct submission |
| 10 | PAO1 genomic sequence | 98 | Stover et al (2000) |
| 11 | Flagellin Bordetella avium | 87 | Sebaihia et al (2006) |
| 12 | Brevibacillus borstelensis 16S ribosomal RNA | 94 | Kop et al (1984) |
| 13 | Temperature-sensitive lambda-repressor | 100 | Direct submission |
| 14 | 1-acyl-sn-glycerol-3-phosphate acyltransferase | 100 | Direct submission |
| 15 | Purine NTPase [Marinomonas sp. MED121] | 41 | Direct submission |
| 16 | Glucose-inhibited division protein A | 98 | Lee et al (2006) |
| 17 | Putative ABC transporter | 75 | Direct submission |
| 18 | Putative lipoprotein | 47 | Parkhill et al (2001) |
| 19 | Phosphoenolpyruvate carboxykinase (ATP) | 64 | Direct submission |
| 20 | Stage II sporulation protein Q | 42 | Ivanova et al (2003) |
| 21 | Transposase of IS658 [Bacillus halodurans] | 61 | Takami et al (2000) |
| 22 | Archaeal/vacuolar-type H+-ATPase subunit B | 59 | Direct submission |
| 23 | Hypothetical protein Bxe_A1507 | 79 | Direct submission |
| 24 | Catalase [Pseudomonas aeruginosa PA14] | 98 | Direct submission |
| 25 | Membrane protease, stomatin/prohibitin | 72 | Direct submission |

SEQUENCE LISTING

```
<160> NUMBER OF SEQ ID NOS: 66

<210> SEQ ID NO 1
<211> LENGTH: 128
<212> TYPE: PRT
<213> ORGANISM: Pseudomonas aeruginosa

<400> SEQUENCE: 1

Ala Glu Cys Ser Val Asp Ile Gln Gly Asn Asp Gln Met Gln Phe Asn
1               5                   10                  15

Thr Asn Ala Ile Thr Val Asp Lys Ser Cys Lys Gln Phe Thr Val Asn
            20                  25                  30
```

```
Leu Ser His Pro Gly Asn Leu Pro Lys Asn Val Met Gly His Asn Trp
        35                  40                  45

Val Leu Ser Thr Ala Ala Asp Met Gln Gly Val Val Thr Asp Gly Met
 50                  55                  60

Ala Ser Gly Leu Asp Lys Asp Tyr Leu Lys Pro Asp Asp Ser Arg Val
 65                  70                  75                  80

Ile Ala His Thr Lys Leu Ile Gly Ser Gly Glu Lys Asp Ser Val Thr
                 85                  90                  95

Phe Asp Val Ser Lys Leu Lys Glu Gly Glu Gln Tyr Met Phe Phe Cys
            100                 105                 110

Thr Phe Pro Gly His Ser Ala Leu Met Lys Gly Thr Leu Thr Leu Lys
        115                 120                 125

<210> SEQ ID NO 2
<211> LENGTH: 28
<212> TYPE: PRT
<213> ORGANISM: Pseudomonas aeruginosa

<400> SEQUENCE: 2

Leu Ser Thr Ala Ala Asp Met Gln Gly Val Val Thr Asp Gly Met Ala
 1               5                  10                  15

Ser Gly Leu Asp Lys Asp Tyr Leu Lys Pro Asp Asp
            20                  25

<210> SEQ ID NO 3
<211> LENGTH: 105
<212> TYPE: PRT
<213> ORGANISM: Phormidium laminosum

<400> SEQUENCE: 3

Glu Thr Phe Thr Val Lys Met Gly Ala Asp Ser Gly Leu Leu Gln Phe
 1               5                  10                  15

Glu Pro Ala Asn Val Thr Val His Pro Gly Asp Thr Val Lys Trp Val
            20                  25                  30

Asn Asn Lys Leu Pro Pro His Asn Ile Leu Phe Asp Asp Lys Gln Val
                 35                  40                  45

Pro Gly Ala Ser Lys Glu Leu Ala Asp Lys Leu Ser His Ser Gln Leu
 50                  55                  60

Met Phe Ser Pro Gly Glu Ser Tyr Glu Ile Thr Phe Ser Ser Asp Phe
 65                  70                  75                  80

Pro Ala Gly Thr Tyr Thr Tyr Tyr Cys Ala Pro His Arg Gly Ala Gly
                 85                  90                  95

Met Val Gly Lys Ile Thr Val Glu Gly
            100                 105

<210> SEQ ID NO 4
<211> LENGTH: 155
<212> TYPE: PRT
<213> ORGANISM: Thiobacillus ferrooxidans

<400> SEQUENCE: 4

Gly Thr Leu Asp Thr Thr Trp Lys Glu Ala Thr Leu Pro Gln Val Lys
 1               5                  10                  15

Ala Met Leu Glu Lys Asp Thr Gly Lys Val Ser Gly Asp Thr Val Thr
            20                  25                  30

Tyr Ser Gly Lys Thr Val His Val Val Ala Ala Val Leu Pro Gly
                 35                  40                  45

Phe Pro Phe Pro Ser Phe Glu Val His Asp Lys Lys Asn Pro Thr Leu
```

```
            50                  55                  60
Glu Ile Pro Ala Gly Ala Thr Val Asp Val Thr Phe Ile Asn Thr Asn
 65                  70                  75                  80

Lys Gly Phe Gly His Ser Phe Asp Ile Thr Lys Gly Pro Pro Tyr
                 85                  90                  95

Ala Val Met Pro Val Ile Asp Pro Ile Val Ala Gly Thr Gly Phe Ser
                100                 105                 110

Pro Val Pro Lys Asp Gly Lys Phe Gly Tyr Thr Asp Phe Thr Trp His
                115                 120                 125

Pro Thr Ala Gly Thr Tyr Tyr Tyr Val Cys Gln Ile Pro Gly His Ala
            130                 135                 140

Ala Thr Gly Met Phe Gly Lys Ile Val Val Lys
145                 150                 155

<210> SEQ ID NO 5
<211> LENGTH: 124
<212> TYPE: PRT
<213> ORGANISM: Achromobacter cycloclastes

<400> SEQUENCE: 5

Ala Asp Phe Glu Val His Met Leu Asn Lys Gly Lys Asp Gly Ala Met
  1               5                  10                  15

Val Phe Glu Pro Ala Ser Leu Lys Val Ala Pro Gly Asp Thr Val Thr
                 20                  25                  30

Phe Ile Pro Thr Asp Lys Gly His Asn Val Glu Thr Ile Lys Gly Met
             35                  40                  45

Ile Pro Asp Gly Ala Glu Ala Phe Lys Ser Lys Ile Asn Glu Asn Tyr
         50                  55                  60

Lys Val Thr Phe Thr Ala Pro Gly Val Tyr Gly Val Lys Cys Thr Pro
 65                  70                  75                  80

His Tyr Gly Met Gly Met Val Gly Val Gln Val Gly Asp Ala Pro
                 85                  90                  95

Ala Asn Leu Glu Ala Val Lys Gly Ala Lys Asn Pro Lys Lys Ala Gln
                100                 105                 110

Glu Arg Leu Asp Ala Ala Leu Ala Ala Leu Gly Asn
            115                 120

<210> SEQ ID NO 6
<211> LENGTH: 128
<212> TYPE: PRT
<213> ORGANISM: Alcaligenes faecalis

<400> SEQUENCE: 6

Ala Cys Asp Val Ser Ile Glu Gly Asn Asp Ser Met Gln Phe Asn Thr
  1               5                  10                  15

Lys Ser Ile Val Val Asp Lys Thr Cys Lys Glu Phe Thr Ile Asn Leu
                 20                  25                  30

Lys His Thr Gly Lys Leu Pro Lys Ala Ala Met Gly His Asn Val Val
             35                  40                  45

Val Ser Lys Lys Ser Asp Glu Ser Ala Val Ala Thr Asp Gly Met Lys
         50                  55                  60

Ala Gly Leu Asn Asn Asp Tyr Val Lys Ala Gly Asp Glu Arg Val Ile
 65                  70                  75                  80

Ala His Thr Ser Val Ile Gly Gly Gly Glu Thr Asp Ser Val Thr Phe
                 85                  90                  95

Asp Val Ser Lys Leu Lys Glu Gly Glu Asp Tyr Ala Phe Phe Cys Ser
```

```
                100                 105                 110
Phe Pro Gly His Trp Ser Ile Met Lys Gly Thr Ile Glu Leu Gly Ser
        115                 120                 125

<210> SEQ ID NO 7
<211> LENGTH: 129
<212> TYPE: PRT
<213> ORGANISM: Achromobacter xylosoxidans

<400> SEQUENCE: 7

Ala Gln Cys Glu Ala Thr Ile Glu Ser Asn Asp Ala Met Gln Tyr Asn
1               5                   10                  15

Leu Lys Glu Met Val Val Asp Lys Ser Cys Lys Gln Phe Thr Val His
            20                  25                  30

Leu Lys His Val Gly Lys Met Ala Lys Val Ala Met Gly His Asn Trp
        35                  40                  45

Val Leu Thr Lys Glu Ala Asp Lys Gln Gly Val Ala Thr Asp Gly Met
    50                  55                  60

Asn Ala Gly Leu Ala Gln Asp Tyr Val Lys Ala Gly Asp Thr Arg Val
65                  70                  75                  80

Ile Ala His Thr Lys Val Ile Gly Gly Gly Glu Ser Asp Ser Val Thr
                85                  90                  95

Phe Asp Val Ser Lys Leu Thr Pro Gly Glu Ala Tyr Ala Tyr Phe Cys
            100                 105                 110

Ser Phe Pro Gly His Trp Ala Met Met Lys Gly Thr Leu Lys Leu Ser
        115                 120                 125

Asn

<210> SEQ ID NO 8
<211> LENGTH: 129
<212> TYPE: PRT
<213> ORGANISM: Bordetella bronchiseptica

<400> SEQUENCE: 8

Ala Glu Cys Ser Val Asp Ile Ala Gly Thr Asp Gln Met Gln Phe Asp
1               5                   10                  15

Lys Lys Ala Ile Glu Val Ser Lys Ser Cys Lys Gln Phe Thr Val Asn
            20                  25                  30

Leu Lys His Thr Gly Lys Leu Pro Arg Asn Val Met Gly His Asn Trp
        35                  40                  45

Val Leu Thr Lys Thr Ala Asp Met Gln Ala Val Glu Lys Asp Gly Ile
    50                  55                  60

Ala Ala Gly Leu Asp Asn Gln Tyr Leu Lys Ala Gly Asp Thr Arg Val
65                  70                  75                  80

Leu Ala His Thr Lys Val Leu Gly Gly Gly Glu Ser Asp Ser Val Thr
                85                  90                  95

Phe Asp Val Ala Lys Leu Ala Ala Gly Asp Asp Tyr Thr Phe Phe Cys
            100                 105                 110

Ser Phe Pro Gly His Gly Ala Leu Met Lys Gly Thr Leu Lys Leu Val
        115                 120                 125

Asp

<210> SEQ ID NO 9
<211> LENGTH: 129
<212> TYPE: PRT
<213> ORGANISM: Methylomonas sp.
```

<400> SEQUENCE: 9

```
Ala Ser Cys Glu Thr Thr Val Thr Ser Gly Asp Thr Met Thr Tyr Ser
1               5                   10                  15

Thr Arg Ser Ile Ser Val Pro Ala Ser Cys Ala Glu Phe Thr Val Asn
            20                  25                  30

Phe Glu His Lys Gly His Met Pro Lys Thr Gly Met Gly His Asn Trp
        35                  40                  45

Val Leu Ala Lys Ser Ala Asp Val Gly Asp Val Ala Lys Glu Gly Ala
    50                  55                  60

His Ala Gly Ala Asp Asn Asn Phe Val Thr Pro Gly Asp Lys Arg Val
65                  70                  75                  80

Ile Ala Phe Thr Pro Ile Ile Gly Gly Gly Glu Lys Thr Ser Val Lys
                85                  90                  95

Phe Lys Val Ser Ala Leu Ser Lys Asp Glu Ala Tyr Thr Tyr Phe Cys
            100                 105                 110

Ser Tyr Pro Gly His Phe Ser Met Met Arg Gly Thr Leu Lys Leu Glu
        115                 120                 125

Glu
```

<210> SEQ ID NO 10
<211> LENGTH: 166
<212> TYPE: PRT
<213> ORGANISM: Neisseria meningitidis

<400> SEQUENCE: 10

```
Cys Ser Gln Glu Pro Ala Ala Pro Ala Glu Ala Thr Pro Ala Ala
1               5                   10                  15

Glu Ala Pro Ala Ser Glu Ala Pro Ala Ala Glu Ala Pro Ala Asp
            20                  25                  30

Ala Ala Glu Ala Pro Ala Ala Gly Asn Cys Ala Ala Thr Val Glu Ser
            35                  40                  45

Asn Asp Asn Met Gln Phe Asn Thr Lys Asp Ile Gln Val Ser Lys Ala
    50                  55                  60

Cys Lys Glu Phe Thr Ile Thr Leu Lys His Thr Gly Thr Gln Pro Lys
65                  70                  75                  80

Thr Ser Met Gly His Asn Ile Val Ile Gly Lys Thr Glu Asp Met Asp
                85                  90                  95

Gly Ile Phe Lys Asp Gly Val Gly Ala Ala Asp Thr Asp Tyr Val Lys
            100                 105                 110

Pro Asp Asp Ala Arg Val Val Ala His Thr Lys Leu Ile Gly Gly Gly
        115                 120                 125

Glu Glu Ser Ser Leu Thr Leu Asp Pro Ala Lys Leu Ala Asp Gly Glu
    130                 135                 140

Tyr Lys Phe Ala Cys Thr Phe Pro Gly His Gly Ala Leu Met Asn Gly
145                 150                 155                 160

Lys Val Thr Leu Val Asp
                165
```

<210> SEQ ID NO 11
<211> LENGTH: 128
<212> TYPE: PRT
<213> ORGANISM: Pseudomonas fluorescens

<400> SEQUENCE: 11

```
Ala Glu Cys Lys Thr Thr Ile Asp Ser Thr Asp Gln Met Ser Phe Asn
1               5                   10                  15
```

```
Thr Lys Ala Ile Glu Ile Asp Lys Ala Cys Lys Thr Phe Thr Val Glu
            20                  25                  30

Leu Thr His Ser Gly Ser Leu Pro Lys Asn Val Met Gly His Asn Leu
        35                  40                  45

Val Ile Ser Lys Gln Ala Asp Met Gln Pro Ile Ala Thr Asp Gly Leu
 50                  55                  60

Ser Ala Gly Ile Asp Lys Asn Tyr Leu Lys Glu Gly Asp Thr Arg Val
 65                  70                  75                  80

Ile Ala His Thr Lys Val Ile Gly Ala Gly Glu Lys Asp Ser Leu Thr
                85                  90                  95

Ile Asp Val Ser Lys Leu Asn Ala Ala Glu Lys Tyr Gly Phe Phe Cys
            100                 105                 110

Ser Phe Pro Gly His Ile Ser Met Met Lys Gly Thr Val Thr Leu Lys
        115                 120                 125

<210> SEQ ID NO 12
<211> LENGTH: 128
<212> TYPE: PRT
<213> ORGANISM: Pseudomonas chlororaphis

<400> SEQUENCE: 12

Ala Glu Cys Lys Val Asp Val Asp Ser Thr Asp Gln Met Ser Phe Asn
 1               5                  10                  15

Thr Lys Glu Ile Thr Ile Asp Lys Ser Cys Lys Thr Phe Thr Val Asn
            20                  25                  30

Leu Thr His Ser Gly Ser Leu Pro Lys Asn Val Met Gly His Asn Trp
        35                  40                  45

Val Leu Ser Lys Ser Ala Asp Met Ala Gly Ile Ala Thr Asp Gly Met
 50                  55                  60

Ala Ala Gly Ile Asp Lys Asp Tyr Leu Lys Pro Gly Asp Ser Arg Val
 65                  70                  75                  80

Ile Ala His Thr Lys Ile Ile Gly Ser Gly Glu Lys Asp Ser Val Thr
                85                  90                  95

Phe Asp Val Ser Lys Leu Thr Ala Gly Glu Ser Tyr Glu Phe Phe Cys
            100                 105                 110

Ser Phe Pro Gly His Asn Ser Met Met Lys Gly Ala Val Val Leu Lys
        115                 120                 125

<210> SEQ ID NO 13
<211> LENGTH: 129
<212> TYPE: PRT
<213> ORGANISM: Xylella fastidiosa

<400> SEQUENCE: 13

Lys Thr Cys Ala Val Thr Ile Ser Ala Asn Asp Gln Met Lys Phe Asp
 1               5                  10                  15

Gln Asn Thr Ile Lys Ile Ala Ala Glu Cys Thr His Val Asn Leu Thr
            20                  25                  30

Leu Thr His Thr Gly Lys Lys Ser Ala Arg Val Met Gly His Asn Trp
        35                  40                  45

Val Leu Thr Lys Thr Thr Asp Met Gln Ala Val Ala Leu Ala Gly Leu
 50                  55                  60

His Ala Thr Leu Ala Asp Asn Tyr Val Pro Lys Ala Asp Pro Arg Val
 65                  70                  75                  80

Ile Ala His Thr Ala Ile Ile Gly Gly Gly Glu Arg Thr Ser Ile Thr
                85                  90                  95
```

```
Phe Pro Thr Asn Thr Leu Ser Lys Asn Val Ser Tyr Thr Phe Phe Cys
            100                 105                 110

Ser Phe Pro Gly His Trp Ala Leu Met Lys Gly Thr Leu Asn Phe Gly
        115                 120                 125

Gly

<210> SEQ ID NO 14
<211> LENGTH: 138
<212> TYPE: PRT
<213> ORGANISM: Cucumis sativus

<400> SEQUENCE: 14

Met Gln Ser Thr Val His Ile Val Gly Asp Asn Thr Gly Trp Ser Val
1               5                   10                  15

Pro Ser Ser Pro Asn Phe Tyr Ser Gln Trp Ala Gly Lys Thr Phe
            20                  25                  30

Arg Val Gly Asp Ser Leu Gln Phe Asn Phe Pro Ala Asn Ala His Asn
        35                  40                  45

Val His Glu Met Glu Thr Lys Gln Ser Phe Asp Ala Cys Asn Phe Val
    50                  55                  60

Asn Ser Asp Asn Asp Val Glu Arg Thr Ser Pro Val Ile Glu Arg Leu
65                  70                  75                  80

Asp Glu Leu Gly Met His Tyr Phe Val Cys Thr Val Gly Thr His Cys
                85                  90                  95

Ser Asn Gly Gln Lys Leu Ser Ile Asn Val Val Ala Ala Asn Ala Thr
            100                 105                 110

Val Ser Met Pro Pro Ser Ser Pro Pro Ser Ser Val Met Pro
        115                 120                 125

Pro Pro Val Met Pro Pro Ser Pro Ser
    130                 135

<210> SEQ ID NO 15
<211> LENGTH: 162
<212> TYPE: PRT
<213> ORGANISM: Chloroflexus aurantiacus

<400> SEQUENCE: 15

Met Lys Ile Thr Leu Arg Met Met Val Leu Ala Val Leu Thr Ala Met
1               5                   10                  15

Ala Met Val Leu Ala Ala Cys Gly Gly Gly Ser Ser Gly Gly Ser
            20                  25                  30

Thr Gly Gly Gly Ser Gly Ser Gly Pro Val Thr Ile Glu Ile Gly Ser
        35                  40                  45

Lys Gly Glu Glu Leu Ala Phe Asp Lys Thr Glu Leu Thr Val Ser Ala
    50                  55                  60

Gly Gln Thr Val Thr Ile Arg Phe Lys Asn Asn Ser Ala Val Gln Gln
65                  70                  75                  80

His Asn Trp Ile Leu Val Lys Gly Gly Glu Ala Glu Ala Ala Asn Ile
                85                  90                  95

Ala Asn Ala Gly Leu Ser Ala Gly Pro Ala Ala Asn Tyr Leu Pro Ala
            100                 105                 110

Asp Lys Ser Asn Ile Ile Ala Glu Ser Pro Leu Ala Asn Gly Asn Glu
        115                 120                 125

Thr Val Glu Val Thr Phe Thr Ala Pro Ala Ala Gly Thr Tyr Leu Tyr
    130                 135                 140
```

```
Ile Cys Thr Val Pro Gly His Tyr Pro Leu Met Gln Gly Lys Leu Val
145                 150                 155                 160

Val Asn
```

<210> SEQ ID NO 16
<211> LENGTH: 140
<212> TYPE: PRT
<213> ORGANISM: Chloroflexus aurantiacus

<400> SEQUENCE: 16

```
Ala Ala Asn Ala Pro Gly Gly Ser Asn Val Val Asn Glu Thr Pro Ala
1               5                   10                  15

Gln Thr Val Glu Val Arg Ala Ala Pro Asp Ala Leu Ala Phe Ala Gln
                20                  25                  30

Thr Ser Leu Ser Leu Pro Ala Asn Thr Val Val Arg Leu Asp Phe Val
            35                  40                  45

Asn Gln Asn Asn Leu Gly Val Gln His Asn Trp Val Leu Val Asn Gly
50                  55                  60

Gly Asp Asp Val Ala Ala Val Asn Thr Ala Ala Gln Asn Asn Ala
65                  70                  75                  80

Asp Ala Leu Phe Val Pro Pro Asp Thr Pro Asn Ala Leu Ala Trp
                85                  90                  95

Thr Ala Met Leu Asn Ala Gly Glu Ser Gly Ser Val Thr Phe Arg Thr
            100                 105                 110

Pro Ala Pro Gly Thr Tyr Leu Tyr Ile Cys Thr Phe Pro Gly His Tyr
        115                 120                 125

Leu Ala Gly Met Lys Gly Thr Leu Thr Val Thr Pro
    130                 135                 140
```

<210> SEQ ID NO 17
<211> LENGTH: 96
<212> TYPE: PRT
<213> ORGANISM: Cucumis sativus

<400> SEQUENCE: 17

```
Ala Val Tyr Val Val Gly Gly Ser Gly Gly Trp Thr Phe Asn Thr Glu
1               5                   10                  15

Ser Trp Pro Lys Gly Lys Arg Phe Arg Ala Gly Asp Ile Leu Leu Phe
                20                  25                  30

Asn Tyr Asn Pro Ser Met His Asn Val Val Val Asn Gln Gly Gly
            35                  40                  45

Phe Ser Thr Cys Asn Thr Pro Ala Gly Ala Lys Val Tyr Thr Ser Gly
50                  55                  60

Arg Asp Gln Ile Lys Leu Pro Lys Gly Gln Ser Tyr Phe Ile Cys Asn
65                  70                  75                  80

Phe Pro Gly His Cys Gln Ser Gly Met Lys Ile Ala Val Asn Ala Leu
                85                  90                  95
```

<210> SEQ ID NO 18
<211> LENGTH: 166
<212> TYPE: PRT
<213> ORGANISM: Neisseria gonorrhoeae

<400> SEQUENCE: 18

```
Cys Ser Gln Glu Pro Ala Ala Pro Ala Ala Glu Ala Thr Pro Ala Gly
1               5                   10                  15

Glu Ala Pro Ala Ser Glu Ala Pro Ala Ala Glu Ala Ala Pro Ala Asp
                20                  25                  30
```

```
Ala Ala Glu Ala Pro Ala Ala Gly Asn Cys Ala Ala Thr Val Glu Ser
            35                  40                  45

Asn Asp Asn Met Gln Phe Asn Thr Lys Asp Ile Gln Val Ser Lys Ala
 50                  55                  60

Cys Lys Glu Phe Thr Ile Thr Leu Lys His Thr Gly Thr Gln Pro Lys
 65                  70                  75                  80

Ala Ser Met Gly His Asn Leu Val Ile Ala Lys Ala Glu Asp Met Asp
                 85                  90                  95

Gly Val Phe Lys Asp Gly Val Gly Ala Ala Asp Thr Asp Tyr Val Lys
                100                 105                 110

Pro Asp Asp Ala Arg Val Val Ala His Thr Lys Leu Ile Gly Gly Gly
            115                 120                 125

Glu Glu Ser Ser Leu Thr Leu Asp Pro Ala Lys Leu Ala Asp Gly Asp
130                 135                 140

Tyr Lys Phe Ala Cys Thr Phe Pro Gly His Gly Ala Leu Met Asn Gly
145                 150                 155                 160

Lys Val Thr Leu Val Asp
                165

<210> SEQ ID NO 19
<211> LENGTH: 150
<212> TYPE: PRT
<213> ORGANISM: Vibrio parahaemolyticus

<400> SEQUENCE: 19

Met Ser Leu Arg Ile Leu Ala Ala Thr Leu Ala Leu Ala Gly Leu Ser
 1               5                  10                  15

Phe Gly Ala Gln Ala Ser Ala Glu Cys Glu Val Ser Ile Asp Ala Asn
                 20                  25                  30

Asp Met Met Gln Phe Ser Thr Lys Thr Leu Ser Val Pro Ala Thr Cys
             35                  40                  45

Lys Glu Val Thr Leu Thr Leu Asn His Thr Gly Lys Met Pro Ala Gln
 50                  55                  60

Ser Met Gly His Asn Val Val Ile Ala Asp Thr Ala Asn Ile Gln Ala
 65                  70                  75                  80

Val Gly Thr Asp Gly Met Ser Ala Gly Ala Asp Asn Ser Tyr Val Lys
                 85                  90                  95

Pro Asp Asp Glu Arg Val Tyr Ala His Thr Lys Val Val Gly Gly Gly
            100                 105                 110

Glu Ser Thr Ser Ile Thr Phe Ser Thr Glu Lys Met Thr Ala Gly Gly
            115                 120                 125

Asp Tyr Ser Phe Phe Cys Ser Phe Pro Gly His Trp Ala Ile Met Gln
130                 135                 140

Gly Lys Phe Glu Phe Lys
145                 150

<210> SEQ ID NO 20
<211> LENGTH: 33
<212> TYPE: PRT
<213> ORGANISM: Chloroflexus aurantiacus

<400> SEQUENCE: 20

His Asn Trp Val Leu Val Asn Gly Gly Asp Asp Val Ala Ala Ala Val
 1               5                  10                  15

Asn Thr Ala Ala Gln Asn Asn Ala Asp Ala Leu Phe Val Pro Pro
                 20                  25                  30
```

Asp

<210> SEQ ID NO 21
<211> LENGTH: 28
<212> TYPE: PRT
<213> ORGANISM: Bordetella pertussis

<400> SEQUENCE: 21

Leu Thr Lys Thr Ala Asp Met Gln Ala Val Glu Lys Asp Gly Ile Ala
1               5                   10                  15

Ala Gly Leu Asp Asn Gln Tyr Leu Lys Ala Gly Asp
            20                  25

<210> SEQ ID NO 22
<211> LENGTH: 27
<212> TYPE: PRT
<213> ORGANISM: Neisseria meningitidis

<400> SEQUENCE: 22

Ile Gly Lys Thr Glu Asp Met Asp Gly Ile Phe Lys Asp Gly Val Gly
1               5                   10                  15

Ala Ala Asp Thr Asp Tyr Val Lys Pro Asp Asp
            20                  25

<210> SEQ ID NO 23
<211> LENGTH: 27
<212> TYPE: PRT
<213> ORGANISM: Pseudomonas syringae

<400> SEQUENCE: 23

Ser Lys Lys Ala Asp Ala Ser Ala Ile Thr Thr Asp Gly Met Ser Val
1               5                   10                  15

Gly Ile Asp Lys Asp Tyr Val Lys Pro Asp Asp
            20                  25

<210> SEQ ID NO 24
<211> LENGTH: 27
<212> TYPE: PRT
<213> ORGANISM: Vibrio parahaemolyticus

<400> SEQUENCE: 24

Ala Asp Thr Ala Asn Ile Gln Ala Val Gly Thr Asp Gly Met Ser Ala
1               5                   10                  15

Gly Ala Asp Asn Ser Tyr Val Lys Pro Asp Asp
            20                  25

<210> SEQ ID NO 25
<211> LENGTH: 27
<212> TYPE: PRT
<213> ORGANISM: Bordetella bronchiseptica

<400> SEQUENCE: 25

Thr Lys Thr Ala Asp Met Gln Ala Val Glu Lys Asp Gly Ile Ala Ala
1               5                   10                  15

Gly Leu Asp Asn Gln Tyr Leu Lys Ala Gly Asp
            20                  25

<210> SEQ ID NO 26
<211> LENGTH: 592
<212> TYPE: DNA
<213> ORGANISM: Pseudomonas aeruginosa

<400> SEQUENCE: 26

```
cgtggcaggc atacagcatt tcaatcggtt cggcaaaggt aacgctttgg gtttcaagcg    60
catgtgcctg tttcgctact ccaccggcac gtttaaaggc ggacgttcta atagaaaca    120
tcctgcacaa agcacgctgg ttgtccctt  cacacattta gcagaactac ggcaactgcc   180
tcacttggct gcttgtcaaa gcaccgtgac ccgggaaggt gcacgcaaat ttgtagtcgc   240
cgtcagccaa tttggcagga tccaaagtca gggaagactc ttcgccgccg ccgatcagtt   300
tggtgtgggc aacaacgcgc gcatcatcag gtttgacata gtcagtatcg gcagcaccta   360
cgccgtcttt aaatacgccg tccaagactt cagctcaggc aaacacaatg ttgtgaccaa   420
tgctggcttt gggttgcata ccaaaatgat taagatatat aaaaaaatca taaaaaaatt   480
aattagtaaa ataattatat tataaaacta catatagagc gctaagaaaa cattggataa   540
aaagaaagag atcatttgtc gaatatatat atataataaa atgtatttta at           592
```

<210> SEQ ID NO 27
<211> LENGTH: 612
<212> TYPE: DNA
<213> ORGANISM: Pseudomonas aeruginosa

<400> SEQUENCE: 27

```
atacctgccc ggtacttctg aacagcgtc  gtcaccttat cgggagatac cgagtaggtg    60
atgccgacgg cgccgccgac cttcatgccc tcaacggtct ggaagctgat cgcttcctcg   120
ccgcccagg  tctcggtctg cgtgaaggtg gggaacaggt agagctcctc gttcacgcct   180
acccagtagc gcccagttcc gacctcacgc gtctccacac ccttctcgga gccgtagaga   240
ttgacgatca cgccgacgtt gccggcaggc accttcgaac agcccgccag gacggcgagc   300
aggcacagca ttgcagcagc gggaatccgc ttcattggtc tttctccttg ctggtggtgg   360
ccgcttgttc gcggcgggtg ttggcgaggt ggacgccgag gcagaccgag gcgatcaacc   420
agacgccagg gatggcgaat cccgcgaaaa ccagaacgtc gtcgcgactg ctgaccaggg   480
ccggcccaat gccgccacc  agggcgactg acagtccggc ataggccagc agcgcgatac   540
agatcaggaa gagcttcccg ggcttgatga gaggtttctt gtccatgctt tcctccaggc   600
aagccgatgg cc                                                      612
```

<210> SEQ ID NO 28
<211> LENGTH: 231
<212> TYPE: DNA
<213> ORGANISM: Pseudomonas aeruginosa

<400> SEQUENCE: 28

```
atatcccccg tatttccctc atatttggga tatcgtcgcg tttcaccgct ctcttagtta    60
ctcgccccc  ctctcccgcc tcccctcct  cccctctccc tccctccgac ttccctgcgc   120
gcatcccgca tccctctcc  cctttcggat tgccccttc  accaacgcgt ccgtccccac   180
cgcttttctc gcccgctcag cgggccctac gcgcccccct cctccccgca t            231
```

<210> SEQ ID NO 29
<211> LENGTH: 782
<212> TYPE: DNA
<213> ORGANISM: Pseudomonas aeruginosa

<400> SEQUENCE: 29

```
tgagaccggg tacgagcttc ccaactggaa ccccgttcgc tgggaactgc gccacctgct    60
gatcgccctg cgcacccctcg ccccgccc  ggacagcccg ctgcacgccg gctacaacgg   120
```

-continued

```
catctcgccg tacaagctgg gcgaacacaa catcaagttc cgcgtcgtcc ccgccccgga    180
gaagtgcccg gcctaccagc taccgaagca gaaccaggac ctgcccaact tcctccgcgc    240
cgccctgtac cagcaactct ccatcgaccg caccccgcc tgctacgcct tccaggtgca     300
gcgccaggac ccggccaagt acatgccat cgaagacacc agcgtcgaat ggaaggagtc     360
ggacgcgccc ttcgctacca tagccgacat cattgtgcca gctcaggatt cgatagccg    420 ggaacagaac ctgttctgtg caacctttc gttcaacccc tggcacgcgc tgccggagca    480
tcggccgatc ggcgggatca accggttgcg gaaggcggtt tacgaggcgg tcagtgggta   540
taggttgggg aggaatgggt gagggtttag ggggaggagt gcttggtgtt acgttgatcg   600
ggaatggcca gaatcggcca gaaacggcca ttcgatcaac gcgctttcag gtctatcaag    660
cacgtggcgc gtcaccgttg agcaccttaa ctagaacgcg ttcctaccga ttgatacacg    720
accatcaact tacagtgtct ggcaggtaac aaagactcga atcgccctaa ggagtcgttc    780
at                                                                    782
```

<210> SEQ ID NO 30
<211> LENGTH: 115
<212> TYPE: DNA
<213> ORGANISM: Pseudomonas aeruginosa

<400> SEQUENCE: 30

```
agttcacgca ggaaccggtc gagcggtacg gcagcatcga tgcggggttc cgggatcccg     60
ccggcaatgg ctggaagatg atccagtcgc ccgcaggcgc ctcctgacga atagg          115
```

<210> SEQ ID NO 31
<211> LENGTH: 688
<212> TYPE: DNA
<213> ORGANISM: Pseudomonas aeruginosa

<400> SEQUENCE: 31

```
tagtcccggg tacgagaacc gcgaaggacc ggttcacctc cttctccttg gtgatgatgc     60
cagtgatcgc tccagacgta atgccgccaa tacgcacggc cgccccctgc cgtaccgtca    120
cggtcgtcgt ggattgtcct tcagggtagt cgtagggttc gcgaacgcgg cacagcgcgg    180
cgctattgtt gctaagcgcc acaatccaaa tctgatgctg atcttggtaa tcaagtaggt    240
tctccccgtt gtcgtcaaac cactcataac tcaccacggt attgcagacg tgcaggcctg    300
gagggaatgt tgccggcgca tcaagcttta cgccgcgata tcgatcggcc tgcaagaaac    360
tcgtcacatc atccgattcg ccagtgcatt gaatcgttcg agtcacagag aacccagtat    420
cgggcgaggc ctgcgcctcc aatatctcct tcagctcaat atgatctgca acttgtccag    480
agtccgttat gagttcaaga acgctggcgc gctccattct gctgtgctca acatcctgct    540
catatcggta agtcctcgta ccataatgtt gacggttata tctagccgac gaacatttc     600 cctgtgcgtc ataccacgct gtgatcaatg ccgaggtctg agtccactcg tcacgaagat    660
cgccgtcaca acagggctcg tacccggg                                        688
```

<210> SEQ ID NO 32
<211> LENGTH: 777
<212> TYPE: DNA
<213> ORGANISM: Pseudomonas aeruginosa
<220> FEATURE:
<221> NAME/KEY: modified_base
<222> LOCATION: (98)..(98)
<223> OTHER INFORMATION: a, c, t, g, unknown or other

<400> SEQUENCE: 32

```
atcagtcgct atcctatgta ttttggatgg cgtcttccct tttatagaga cggattgtaa    60
tatgaagtgc gacagctagg aaaaagaaaa ggcccatngc tggcatcgtg tacaatggaa   120
gttaccatac taaccatttt gtacaggagg acccaacatg agctactccc atcttagcat   180
aatcgagcgt ggacaactag aaactttgca tcgactcggt tggtcatgcc gggctatcgg   240
acttgaacta ggccgtcatc cttctaccat cgctcgagaa ttaaagcgag gcagcgacaa   300
tgagggctac tccgctgaat ccgctcagca agcgtcttac gagcgaagaa cgacatgcgt   360
gcctgctgga agtacacac ccgagcttgc cgatgaaatc aacctgaagc taaaggaaac   420
ctggtcaccc gagcagatcg cggaaaaaag acgggcgaca ggggcgtttt tcgtatgctt   480
caaaacaatc tacagatggc tctactccgg gcgccttgca gccggagagg ttacggttct   540
acggcacaag gggaagcggc agaagccggt ggaaacacgc ggccgattcc gggtgggcac   600
cccgattagc aaacgtccga agaagtccg cacacgcacg tcattcggcc attgggaact   660
cgatacggtt gtctccagcc gagggaaaag ccggcttgt gccgccacct ttatggaaag   720
gaagacgcgc ctgtacatgg ctggaaaatg ccggctcgat tcgccctata ggagtcg     777
```

<210> SEQ ID NO 33
<211> LENGTH: 44
<212> TYPE: DNA
<213> ORGANISM: Pseudomonas aeruginosa

<400> SEQUENCE: 33

```
actggtcggt gcggcgttcg cctggagcgt cctggccgtg ccgg                    44
```

<210> SEQ ID NO 34
<211> LENGTH: 603
<212> TYPE: DNA
<213> ORGANISM: Pseudomonas aeruginosa

<400> SEQUENCE: 34

```
atgatcgact ccttagggcg aatcgagtga attatcactg cggctttaaa aagttggcca    60
atttgctaag gatactggca gaatcattgc gtcatggaat tcactgatcg cctacgctga   120
atacattagt gatgccccaa aattggtggt ctgacgagaa cggctccaga tggtgggtca   180
tcaactttcg gaatacttag tcctttatat tagcgatcca aagttttatt aggtgaaatc   240
gaatgtcata tcacggagta gtgccacaat atcgctggat ttaatcgctt ggaagatat    300
ggatcatcta atgatagcaa tgtcgccaag tgtggttggt aaaatcattt cgtaatggag   360
ttcacgtaac gccttcgctc caaaacattg gtgataatgc aatatcaagt cgttggaatt   420
gcaataattc atcagttaca ttcggcaaac ccgcaacatc aacacaatat gtagaatagc   480
atttcaattt tgcgaagaag gcaagtcgct tcattacttt ataacactat gatttaatta   540
cttaacgcac taaagtgatg taactctcgc tctcggtatt gcagtaatc ctcaagttgc   600
tta                                                                603
```

<210> SEQ ID NO 35
<211> LENGTH: 621
<212> TYPE: DNA
<213> ORGANISM: Pseudomonas aeruginosa

<400> SEQUENCE: 35

```
tgatcgactc cttagggcga atcgagaagc ttacagttaa caaatttta cttttcccta    60
ttccatcagg tttatgcacc gaaaaagtgg tgatactggt ggatgaggtg ataaaaaatg   120
```

| | |
|---|---|
| gaagatcaaa aaaatccaaa tcaaccgatt cctttgaaga agtcaaaatc ctggaaaacc | 180 |
| tttctgggga agaagtgggc gtttcccgca atctacatcg gcttagcagc aatcatcctc | 240 |
| gcattcgtga tgtggtatca gggcaacgtg tttcatgcag taagcgatga gcttagcaag | 300 |
| cagccgacgc cagtcgcaca gaaccaaccg gaaacaacgg caccaaacac agaagtttcg | 360 |
| caagatgatg cagtaccagt cagcaaggca acacaaccgc tcgcatggcc agtggcagca | 420 |
| agcgtgagct actccaaagc catggatttc ttcaatgatg cagctgcgaa agaagagcaa | 480 |
| gccaaagcgt tggtcaagta caacaactcg tacatcccgc acacagggat cgacattgtc | 540 |
| tccacggata aaaaaggatt tgatgtcgcc gctgccctcg atggcaaggt gaaaaagtgg | 600 |
| aaaatgatcc gttggtaggc a | 621 |

<210> SEQ ID NO 36
<211> LENGTH: 876
<212> TYPE: DNA
<213> ORGANISM: Pseudomonas aeruginosa

<400> SEQUENCE: 36

| | |
|---|---|
| ataagtacct ggtacgagca cttactgacg tactttctgc ggcagtacac aatacaatct | 60 |
| ttcggtagct caactggtcg agattgctgt taagcgggga gaaggtgtgc tcacagacaa | 120 |
| gggtgcactt aacgcgttga caggcaagtt caccggtcgt tccccgaaag acaaattcgt | 180 |
| tgtggacgaa gcatccgttc atgacaaaat caactgggga cctgtgaacc aaccgatttc | 240 |
| ccgtgaaaaa ttcgacattc tctacgcgga tgtgatggag catctgcaag caaagatct | 300 |
| gtttgttttc gacggttttg ccggtgcgga aagacattc cgtctgccga tccgtgtagt | 360 |
| aaatgaatat gcatggcaca acctgtttgc tcgccaattg ttcgttcgcc catccgaggc | 420 |
| ggaattggct gatcataaag cggaattcac ccgtcgtata tgcacctagc tacaaggcga | 480 |
| atcctgcggt tcacggcacc gactccgaga cgttcatgct tatgagcttt ggcaaagag | 540 |
| tggtgctgat ctgcggaacc gaatacgccg gcgaaaggta gaatcgatc tgcagcgtga | 600 |
| tgggctggct cccgccttgc acaaaatgtt ttgtcgatgc cctgctcggc aaacgttgcg | 660 |
| cagcgaagta gatgtccctc tgatcttcgg tcttgccggc acaggcagat ggacgctatc | 720 |
| ggggtgagcc cggtcatgag cagattcggg ggaagcaatt ccggatggtc ggtaagacgt | 780 |
| gcgtatttga ggggagcgag tggggccgc ggcgagacgt tgcgcgactg tgggaaaagg | 840 |
| taatccccaa tatatggcgc ctcttatcct cttaat | 876 |

<210> SEQ ID NO 37
<211> LENGTH: 47
<212> TYPE: DNA
<213> ORGANISM: Pseudomonas aeruginosa

<400> SEQUENCE: 37

| | |
|---|---|
| cacccagctc gatacggtga gcatgtacat gtcccgcggg cgcaggt | 47 |

<210> SEQ ID NO 38
<211> LENGTH: 631
<212> TYPE: DNA
<213> ORGANISM: Pseudomonas aeruginosa

<400> SEQUENCE: 38

| | |
|---|---|
| tatcgactcc tatagggcga atcgaggctc gaattaccct ctgacggggg cacctccggg | 60 |
| aggacccgcc aaatttttcaa acttgtgctg gacaacaaga attcgcacca ctttggtgca | 120 |

```
ctcttcagcg cctcgcggcg aaccgagcgg caacgccgcg catcgccacc tcgaactcac      180
gcggcaggtt ctcgtcggtg tactgctgcg cgatctcgaa gaagctcagc cggcggcgat      240
acgaagggcg tgacacgaag gccatgatga tcgagacagc atcccggcct cggcctgttc      300
gctcagcaat gccaatgggc tggcccttgc gggtcatgac gaagtagcgg cgagcattac      360
ccttcgccct gctccgtctg ctatcggtcg cgttcgcgtt gtacccggcc tgagtgaagc      420 cccgaataccgctcagcgct ctggtcactt gacctcgcct gatgttcccg tagcgatcaa       480
gatcagcacc ggcgccgggc accacgtact taccttcggg caggatcccc ttggccctga      540
gctgaagctc ggccggcttg ttccgacgcg gcccaccgta gacctcgggg gcaatccaca      600
ccgatgcagg ctgcgcaccg tccgcttcgt a                                     631

<210> SEQ ID NO 39
<211> LENGTH: 148
<212> TYPE: DNA
<213> ORGANISM: Pseudomonas aeruginosa

<400> SEQUENCE: 39
gatattgctc gacaggtagg tgcggtgcac gccgatcacc ggatcgcccc agttgaagac       60
caggtcggtg gtcatgtcga aatcatggct ggcgatgcgc ttggcccagg tcgggaagtc      120
gggcgaagcg cgcacctgca ccgcgatc                                         148

<210> SEQ ID NO 40
<211> LENGTH: 619
<212> TYPE: DNA
<213> ORGANISM: Pseudomonas aeruginosa

<400> SEQUENCE: 40
tgagacccgg gtacgagcag cggcagttcg cgcagaccac gcgccagtgc gatggacggc       60
gggtcgccgg cgcgtccgcc tgagtagttc tccaggccga tgtggataag tccgccgagg      120
aaggtgccgg tagtcaggac cacgttgtcg gcatggaagc gcagtcccat ctgggtcact      180
acgccgcgga cctgatcctg ctcgacgatc aggtcgtcgc aggcctgctg gaatatccac      240
aggttcggct ggttttccag tgtatggcgg atagcggcct tatagagcac gcgatcggct      300
tgtgcacgag tggcgcgcac tgccggcccc ttgcggctgt taaggatgcg gaactggata      360
ccgcccttgt cggtggcttc ggccatgcgc cgccaagggc gtcgatttc cttgaccaga      420 tggctcttgc cgatgccgcc gatggcgggg ttgcagctca tctgccccag ggtttccaca      480
ttgtgggtca acagcagggt tttcacaccc atgcgcgcag ccgcgagtgc ggcttcggtg      540
cctgcatggc caccgccgat cacgattacg tcaaaacggg tagggaaatc caccacgcac      600
ctcggcctgt tcagaagca                                                   619

<210> SEQ ID NO 41
<211> LENGTH: 587
<212> TYPE: DNA
<213> ORGANISM: Pseudomonas aeruginosa

<400> SEQUENCE: 41
actacctact gctactgacc tttatccat cgttgcctct aagtttctgt accgagatat        60
atctccggtg agcagtaact caagagcatc aaaaaatgag gttttcccaa agccattcgg      120
tccatcaagg acagttaggt tctttgagcc aatattgaaa acctgaaatc gaatgccttt      180
aaaattcctc agagcaacct tatttataat taacttcata acctgcctcg gcgatagcat      240
ctaccaaatc agccagtgtc tttaccgggc tatctgttag atccatattt agaacgaagg      300
```

```
actctataaa tgaaagaagt tccggctgcc ttgtaccaag aactctttgg gtatgttttg      360
agtgcagtcc ctcaatgtcg actggagtac cgtctccaat atcaataaag ctaagtttta      420
taacaattct atagagcagt tcattccaac tctccaaccc aatcatctcc ttatagcgag      480
agaaggtgtc aggatcattt atcagaacac tcaatatatc gctcaggctc tcaaaaccaa      540
ttctcgcctt cagattatca agctcagagg gggtgtaata tagaaca                   587
```

<210> SEQ ID NO 42
<211> LENGTH: 190
<212> TYPE: DNA
<213> ORGANISM: Pseudomonas aeruginosa

<400> SEQUENCE: 42

```
cggccagcgc ctgaaggatc tctgctccag gggcgtgatg tggatcgccg agacctgggc       60
ggagatcgac aagtggatct tcgccacctg cacgccgacg gtctgggacg tgcgcggcgc      120
cggcgacctg cgccaggaca cctcgtacct ggtggtgagc aaccaccagt cctgggtcga      180
catccccgcc                                                             190
```

<210> SEQ ID NO 43
<211> LENGTH: 129
<212> TYPE: DNA
<213> ORGANISM: Pseudomonas aeruginosa

<400> SEQUENCE: 43

```
agcttagaac ctttaccaaa ggtgatgcgg agagatgggt aagcacaacc aaaaaagcca       60
gtgattctgc attctggctt gaggttgaag gtaattccat gaccgcacca acaggctcca      120
agccaagct                                                              129
```

<210> SEQ ID NO 44
<211> LENGTH: 619
<212> TYPE: DNA
<213> ORGANISM: Pseudomonas aeruginosa

<400> SEQUENCE: 44

```
tgagacccgg gtaccgaggg taattcgagc cccgctcgcc aaatatgtat gaccattttt       60
cggaggttgg ttgttgttta gtcatgagca aaaacgaaac aaccaaacag cgcggatggt      120
tgaacaagtc cgagatggcc gcgagcctcg ggatttctcc gcaagccttt gataaatggg      180
gcgttcaacc aatcgagcga ataggtcgag aggccttcta cacggtggcg gatgtggtcg      240
aaaaccgcat ccagcacgcc gctcggaaac aacaacctga gggggagcta ccggaaggtc      300
tcgatcccta cgctgaagcc aagctgacac aggagcgact ccggctcacc aaggcccagg      360
cctacgccca agagcagaag aaccaggtcc aggacaagct cctggtcccg gtcccgttcg      420
ccactttcgc cttggcgaag atcgccgcca agattggctc ggcgctggag accgtctgca      480
aaacggtcag tcgccgccac ccggatgctg atcccttgct gatggagtcc ttcgagcggg      540
agatcgcctt ggcgcgaaac cttccgctg agttcagcga cgacatcccg ggaatccttg      600
atgagtacct tgcaaccct                                                   619
```

<210> SEQ ID NO 45
<211> LENGTH: 912
<212> TYPE: DNA
<213> ORGANISM: Pseudomonas aeruginosa

<400> SEQUENCE: 45

```
atacaataaa cgtcgagacg tttattgctt taacctttgg agaatcactc tccgcctggc    60
aacgtcctac tctcccagtc cccttcggga caagtaccat cggcgctgga gggcttaacg   120
gccgtgttcg gtatgggaac gggtgtgtcc cctccgccat catcaccaga cgatgcacat   180
ggatgtgcta gtgtcagcgt tgcgacagga tgtcgcgcac ttagctgacc ttattgattc   240
tttttgctaa aagcgacagg cactaatgta tcacatctgc accatcgcaa tcaagcactt   300
ttttaagaaa aatggtggag ctgaacggga tcgaaccgat gacctcctgc ttgcaaggca   360
ggcgctctcc caactgagct acagccccat aatgggtata tgaaggcgaa aatggtgggc   420
ctaggctgac tcgaacagcc gacctcacgc ttatcaggcg tgcgctctaa ccaactgagc   480
tataggcccg agtttcgggt gcccttacat gctccctcaa aactgaacag cgagcgaaag   540
atctccatag aaaggaggtg atccatccgc accttccggt acggatacct tgttacgact   600
tcaccccagt catctacccc accttcggcg gctggctcct tacggttacc tcaccgactt   660
cgggggttgc aaactcccgt ggtgtgacgg gcggtgtgta caaggcccgg gaacgtattc   720
accgcggcat gctgatccgc gattactagc gattccgact tcatgcaggc gagttgcagg   780
ctgcgatccg aactgagact ggttttaaga gatttgcgaa gtctcgggag cgaacatccc   840
ggtgcaccag gcattggagc acgtgtggac gcccgggcct aggggggatg atggtttggc   900
ctcgaccccg gc                                                       912

<210> SEQ ID NO 46
<211> LENGTH: 269
<212> TYPE: DNA
<213> ORGANISM: Pseudomonas aeruginosa

<400> SEQUENCE: 46
gggacagctg accggtgaac tgggtgccgt gcagaaccgt ctggaatcga ccatcgccaa    60
cctgaacaac gtggttaaca acctgtcgaa cgcccgttcg cgcatccagg acgccgacta   120
cgccacggaa gtgtcgaaca tgtcgaaggc ccagatcctg caacaggctg gcacctcggt   180
tctggcgcaa gccaaccaag tgccgcaaac cgttctgtcg ctgctgcgtt aattcacggc   240
aaagcagtac ggacgggggg agctccggc                                     269

<210> SEQ ID NO 47
<211> LENGTH: 608
<212> TYPE: DNA
<213> ORGANISM: Pseudomonas aeruginosa

<400> SEQUENCE: 47
tgagatccgg gtacgaggtc acgaccgaaa tgttctccct gttgactgcc ttgttgtact    60
ggttttccgt tttggtcagc tcttcctccg cctgcacaac atccagaaa gtggacaacc   120
cgttctcata gcgaatctgt gctgcgcgga aattttcttc cgccatagcc tgcgactcct   180
tgtacatgtc gacgctggac agggatgctt ccatattgaa atacgcctgt tttacttcca   240
cttcaatgct gcgtttcgta tcctccagat cgattttcgt cgcctccaga tcatttttg   300
ccatggagcc ttgataggtc gacaaggccg aatactttg gaacagctcg acattcaatt   360
cggcgagctg gatctcgttt tgcttttgct gaatttcgta acgcttttcg ccagcttgct   420
tcaatgcctc atccaggctg ccaattgtcg gcttcgtcag ctgcgtttcc ttgaccaacg   480
tccactttt gtccaaatcg acacccaggt agttgttcaa gttcaagaat gcgaccggta   540
ccgcattttg cgcgctgagc aaagatgcct tcgcattcat cacgctcacg ctgtgcggac   600
ggcaagtc                                                            608
```

<210> SEQ ID NO 48
<211> LENGTH: 119
<212> TYPE: DNA
<213> ORGANISM: Pseudomonas aeruginosa

<400> SEQUENCE: 48
cgtttcatgc gcgttatttc gcgattaata tcggcggtgc gatcgggccg cttgttggct      60
tgaagctcgg cgccggaggg tccgcctcgt ttttgccgtt tttggtcagc agcgcgatc     119

<210> SEQ ID NO 49
<211> LENGTH: 305
<212> TYPE: DNA
<213> ORGANISM: Pseudomonas aeruginosa

<400> SEQUENCE: 49
ctcccccccc ccgcgaccgc cctccccgcc gcccgggtgc atgctgcggt cgcttcgccg      60
cgctccccgc gccccccgcc cccccctccg tcccgccccc cgcgctcccc tctcctcact     120 ctcccccgc tccctccgcg caccctgttc gccccgcgc ccccgcccc cccgcccc     180 cccatctctc ttcccacccc gccgcctcac gtttcttaac ccgtcagcgg ctcactgacc     240
cccacccgac cccacctcac tacctccccc cctcaggccc ccacgccctt ccccccccat     300
ccttc                                                                305

<210> SEQ ID NO 50
<211> LENGTH: 71
<212> TYPE: DNA
<213> ORGANISM: Pseudomonas aeruginosa

<400> SEQUENCE: 50
caattctaat atgagaatgg ttttcattaa aaattgagag cgggcggcgc cgcgcacggg      60
gcgcggtagt c                                                          71

<210> SEQ ID NO 51
<211> LENGTH: 136
<212> TYPE: DNA
<213> ORGANISM: Pseudomonas aeruginosa

<400> SEQUENCE: 51
atcgtggagc ctgtgatggg ggctgccggc gtcattcctc ctttgccggg atatttggag      60
ggattgcgcg agcttgcgaa ccgctatgac gtccttttga tttttgacga ggtgcagaca     120
ttgcgcttaa gcacag                                                    136

<210> SEQ ID NO 52
<211> LENGTH: 49
<212> TYPE: DNA
<213> ORGANISM: Pseudomonas aeruginosa

<400> SEQUENCE: 52
tactcaatgg cggaaatggc gcatgccagt gaacaccatc gcgatatcc                 49

<210> SEQ ID NO 53
<211> LENGTH: 792
<212> TYPE: DNA
<213> ORGANISM: Pseudomonas aeruginosa

<400> SEQUENCE: 53
atctcgtccg cctgctgcga agtgccatcg atggcgcgct cggcccactc ggggagctgc      60

```
ctttgcaacc gcatttcgtt gaggatcgtc cagaggcgcg aggtcaggtc gcgctctgcc    120
cggatcccgt ggcggagcat ggtgattgag gagttcattg ctggtcctcc tcacgcaggg    180
agtcgagcgc ggcgtcaacc aaatcgccag ccatctctgc agcaatctcc aaggcataca    240
agcacgcgtg ctcttcgtcg gaggtggtca gtgctccgag aatgctagaa acacttagcg    300
tcagggcgat ggccgtgctc aaggcctctt caaccgtcgt ggtcgggtta atcgctgcga    360
atcttcgcgg cggaagctga gacaccggcc ccttcagtac ggccggcccg agcttgagcg    420
cgctcatgcc gcaccgcctt cgtgtcgcga cacgttttca gcatttctgg attgggtcgc    480
gacaccagcc cggcaagctc tgagcaatgc gccagccatg ctccccagca gggcgagagt    540
attgagttcc tgagagagca gcggctcgcc ggcatcgtcc atcgcccggg tcattctcaa    600
aataatcagg gaaccgcctc cggtgatgtg ctcggggggg tgccgagtcg cgtcaacctg    660
gcgggccgta acactgtaga acaacaactc gtccccggtg agcggatctc aggaaatgtc    720
ggggggcgag gggcgggcg cctggggaga ggagggcgtg ggtgatgtgg gctcgggggg    780
gcgagggggg ag                                                         792

<210> SEQ ID NO 54
<211> LENGTH: 229
<212> TYPE: DNA
<213> ORGANISM: Pseudomonas aeruginosa

<400> SEQUENCE: 54
ttcgtcgtgc acgtagacct tctgcacctg tacctggttg ctcatcagga ccaggtcgtt     60
ggcgccgacg atctcgtagt tgatcgtgtt ggtcagctcg aactccgcgc cgcgcgcgga    120
accggtgtag ctgacggtgc gctgctggtt gtcctcgcgg accagcacca ggtggtaggg    180
cgcgttgctg gtgaccttca cgccgctgtt ttccagggtt tccttcagt                 229

<210> SEQ ID NO 55
<211> LENGTH: 612
<212> TYPE: DNA
<213> ORGANISM: Pseudomonas aeruginosa

<400> SEQUENCE: 55
atgatcgact ccttagggcg aatcgagcaa ctactacagc ccacagcctc gttatccgag     60
gcaactacgt ataactgctc ccagatacc cgcctcgctc cgcgatgaat attgccgga     120 gataggcgcg tccttccgcg tctcggttcc tgatgatttg ctggagatgt agccatgggc    180
caacgctgga tcaacaactg gcagacagag ctctcgggtc cgctatcggc gggtgggtt     240 tctcttacca tccccgctgc cgcggctgat cttctgccca tctcggctcc ttctgatttc    300
atcctgctca ctcttgccga tgagtcaggc tctgttcacg aagtggtcaa ggcgacggca    360
aagagcggcg ggaatatcac tgttgcgaga gcctctgagg gtgtgcccgt tgagtggcca    420
tcgggctcga aagtgtacgc ggcgcgacg gcgggaactc tcgcaagcat cgagaaccga    480
atcaccatcc tcgagcaggc tggtcctggg cctggtggcg gcacgttcaa ggcgcaggag    540
gtcaacgact cgactccggt agccctcgcc tcggatacaa cgatcgtgcg cgtatccgca    600
tcgtttgatg gg                                                         612

<210> SEQ ID NO 56
<211> LENGTH: 593
<212> TYPE: DNA
<213> ORGANISM: Pseudomonas aeruginosa

<400> SEQUENCE: 56
```

```
atctaccttt ccgcgatgca tccccggcgt tttgttctat caccgctgag cgtgccatca    60
aggtcgaact ggccaccggt ggcgccgtca ctcgcttcga gctcaggccg acatcgatt    120 ggggcggcct gccggctggc agcgttgccc ccgaccttga gcaaatcgta gctgcaccga   180
gcgtgatggt gcagggtgtc ggtagtgctg ttcaggcatc cagtgccgag gtggcgccgt   240
gactttcctt tcgaagatgg ctcgcttcct cgggctggat gttcagcgtg atcggatcgc   300
ggccgcctgg cgcgggcagg gctttgaggc tggtgtcatt tacgacgaag cagagattct   360
gcggcgtctt ggctggcgtg aacagcttca acggcgactt cgacaagttc tccggtggtt   420
cggtttatca gcatcgccat cccgttgtcg tctagggcgc cgcgcaccga gtccccaatc   480
cgaagctcgc caaccagcac atcaacgatc gcaaacccat cgtcggtgcg aatcgcatag   540
cgaggaaggt tagcgtgata gccgcatacc actcccatta ctgcgatacc tcg          593

<210> SEQ ID NO 57
<211> LENGTH: 155
<212> TYPE: DNA
<213> ORGANISM: Pseudomonas aeruginosa

<400> SEQUENCE: 57 caccccttggc gtcgccttgc ctgctcgtac ttggtgagga tgtggccgaa cagttccggg    60
ctgaccgaag agaagtaggt cggcggaacg ttctcgctcg gcttgaccag ttccggatag   120
gtgccgatcg acaggctggc cggtgccgcc ttgac                              155

<210> SEQ ID NO 58
<211> LENGTH: 114
<212> TYPE: DNA
<213> ORGANISM: Pseudomonas aeruginosa

<400> SEQUENCE: 58
cgcccttcgc tgaccgccgg gctggacggt gcgatcaacc gcgccaaggt cgatcccgcc    60
cgcgccgagc aggcccgacg catgcagcag gcggcccagc agcagatgca gcaa         114

<210> SEQ ID NO 59
<211> LENGTH: 67
<212> TYPE: DNA
<213> ORGANISM: Pseudomonas aeruginosa

<400> SEQUENCE: 59 cgcccttttgc ccctatgcgc tctactacat ccgcaaggga atcgctaagg tacagtccga    60
ggcggag                                                              67

<210> SEQ ID NO 60
<211> LENGTH: 602
<212> TYPE: DNA
<213> ORGANISM: Pseudomonas aeruginosa

<400> SEQUENCE: 60
atggcctggg gcatgggaaa gagtagccta gcgtgcccct gcgcattgag aaaggggaga    60
agtgccagcg acgcgctgcg gatcatgcag ccgatacttg tgtacaggcc gatcacgcag   120
atcgcaccga ccgcgcctgt ccggctgacc atccctgggc acgggttgcc tggcacgtgg   180
ctggcctggg ctgatggtgt ccagggcatg cccgaactga accgcgctcg acttcggcaa   240
ttgcctcacc gtgtcgcgtc catcgacgac gacacgatcg agatcaacct gctgtcagcc   300
gttgggctgg cgcctgttgg cggacagttg atctaccagc cacctgttga cctggctggc   360
```

```
gccgaggtac gaatgcagat ccgcgaagcg ccaggcggga ctgtgctgat gacgctggcg    420
ctcggctctg gcctggatct cgccggcgcc ggaacgatct cgcgggagat atcggcctcc    480
gctacctcgg agctgatgtg gtcgtcggcg gtctacgacc tggacgtgac ataccccggat   540 ggaacggtcc accgctatta cagcgggccg atcagtgtga gccatggggg agggtgctat    600
gg                                                                   602
```

<210> SEQ ID NO 61
<211> LENGTH: 482
<212> TYPE: DNA
<213> ORGANISM: Pseudomonas aeruginosa

<400> SEQUENCE: 61

```
taacagcttt ctgatcaatc ctcagcctgt aacgtgaccg tcataggagg gacgtcgcca     60
agccctacct gttccagggg agggtatgag cgagacctcc gtaaagccag ggtccagggc    120
aaggaagttc ccggcatgtc cagagaagag gtggaaagca tttatgggaa ggcgaaccgg    180
aatggcagca ctgctggtgc cggggccgtt acctactgga atgacaagta catcgatcag    240
accacggttt ctttcgaccg aaacggttgc gttcaaggct cataccagtc gggccacaaa    300
aactgatcca ccgtcgtcaa tcaccccgct ccggcgggt ttttattttg gagccctcaa    360
tcatgaagcc tgcctgcgtg cccctgcgca ttgagaaagg ggcgacgttc gcgacgcgc    420 tgcgtttcat gtagccgata cttgtgtaca ggccgatcac gcagatcgca ccgaccgcgc    480
ct                                                                   482
```

<210> SEQ ID NO 62
<211> LENGTH: 646
<212> TYPE: DNA
<213> ORGANISM: Pseudomonas aeruginosa

<400> SEQUENCE: 62

```
tctcgcccca gtgtaggcgt ggcttcatat gcggtaagtc ctcgtaccat aatgttgaag     60
gaaaaggcta gccgaccgaa catttccctg tgcgtcatac cacccctgtg atcaatgccg    120
aggtctgagt ccactcgtca cgataactcg ccgtcacaac agggtcctca ggaaggctgg    180
actcatcgat atgcacgtga gcagggcttc ccatcgcttg accgcgcgtc tcaatgacgg    240
tcattgtcag caccttggat cgatccgcat caggatctcg tatcgacgga gagacagtga    300
tttcaatcaa tccatagaag cccacgggag caccggaatt cgatgagcca ctaatccacg    360
atgttccagg cggttgctca attggtgaca aatcggtagt tcgaacgtaa acaccgaaaa    420
ggagacgatt ttgatagacc ccaagcattg atagctcgct caacacaact tgttcgtca    480 gttgccagcc gtcaaatgaa acatctttg ccctgacagc gcatgctggt tgttcttctc    540
cctgaccaat taaatctgca cccaagtcga gcgtggccat ggtgttgagg tcatttccaa    600
cccataggcg aaactgcggt gtacctgcct cgtcccctta aatcat                  646
```

<210> SEQ ID NO 63
<211> LENGTH: 90
<212> TYPE: PRT
<213> ORGANISM: Pseudomonas aeruginosa

<400> SEQUENCE: 63

Leu Asn His Phe Gly Met Gln Pro Lys Ala Ser Ile Gly His Asn Ile
1               5                   10                  15

Val Phe Ala Ala Glu Val Leu Asp Gly Val Phe Lys Asp Gly Val Gly
            20                  25                  30

```
Ala Ala Asp Thr Asp Tyr Val Lys Pro Asp Asp Ala Arg Val Val Ala
        35                  40                  45

His Thr Lys Leu Ile Gly Gly Gly Glu Glu Ser Ser Leu Thr Leu Asp
 50                  55                  60

Pro Ala Lys Leu Ala Asp Gly Asp Tyr Lys Phe Ala Cys Thr Phe Pro
 65                  70                  75                  80

Gly His Gly Ala Leu Thr Ser Ser Gln Val
                 85                  90

<210> SEQ ID NO 64
<211> LENGTH: 95
<212> TYPE: PRT
<213> ORGANISM: Neisseria gonorrhoeae

<400> SEQUENCE: 64

Leu Lys His Thr Gly Thr Gln Pro Lys Ala Ser Met Gly His Asn Leu
 1               5                  10                  15

Val Ile Ala Lys Ala Glu Asp Met Asp Gly Val Phe Lys Asp Gly Val
                 20                  25                  30

Gly Ala Ala Asp Thr Asp Tyr Val Lys Pro Asp Asp Ala Arg Val Val
                 35                  40                  45

Ala His Thr Lys Leu Ile Gly Gly Gly Glu Glu Ser Ser Leu Thr Leu
 50                  55                  60

Asp Pro Ala Lys Leu Ala Asp Gly Asp Tyr Lys Phe Ala Cys Thr Phe
 65                  70                  75                  80

Pro Gly His Gly Ala Leu Met Asn Gly Lys Val Thr Leu Val Asp
                 85                  90                  95

<210> SEQ ID NO 65
<211> LENGTH: 95
<212> TYPE: PRT
<213> ORGANISM: Neisseria meningitidis

<400> SEQUENCE: 65

Leu Lys His Thr Gly Thr Gln Pro Lys Ala Ser Met Gly His Asn Leu
 1               5                  10                  15

Val Ile Ala Lys Ala Glu Asp Met Asp Gly Val Phe Lys Asp Gly Val
                 20                  25                  30

Gly Ala Ala Asp Thr Asp Tyr Val Lys Pro Asp Asp Ala Arg Val Val
                 35                  40                  45

Ala His Thr Lys Leu Ile Gly Gly Gly Glu Glu Ser Ser Leu Thr Leu
 50                  55                  60

Asp Pro Ala Lys Leu Ala Asp Gly Asp Tyr Lys Phe Ala Cys Thr Phe
 65                  70                  75                  80

Pro Gly His Gly Ala Leu Met Asn Gly Lys Val Thr Leu Val Asp
                 85                  90                  95

<210> SEQ ID NO 66
<211> LENGTH: 96
<212> TYPE: PRT
<213> ORGANISM: Pseudomonas aeruginosa

<400> SEQUENCE: 66

Leu Ser His Pro Gly Asn Leu Pro Lys Asn Val Met Gly His Asn Trp
 1               5                  10                  15

Val Leu Ser Thr Ala Ala Asp Met Gln Gly Val Val Thr Asp Gly Met
                 20                  25                  30
```

-continued

```
Ala Ser Gly Leu Asp Lys Asp Tyr Leu Lys Pro Asp Asp Ser Arg Val
        35                  40                  45

Ile Ala His Thr Lys Leu Ile Gly Ser Gly Glu Lys Asp Ser Val Thr
        50                  55                  60

Glu Asp Val Ser Lys Leu Lys Glu Gly Glu Gln Tyr Met Phe Phe Cys
65                   70                  75                  80

Thr Phe Pro Gly His Ser Ala Leu Met Lys Gly Thr Leu Thr Leu Lys
                85                  90                  95
```

COMPOSITIONS AND METHODS TO TREAT CANCER WITH CPG RICH DNA AND CUPREDOXINS

RELATED APPLICATIONS

This application is a divisional and claims the benefit, under 35 U.S.C. § 121, of U.S. patent application Ser. No. 11/950,165, filed Dec. 4, 2007, which issued as U.S. Pat. No. 8,017,749, and which claims priority under 35 U.S.C. §§ 119 and 120 to U.S. Provisional Patent Application Ser. No. 60/872,471, filed Dec. 4, 2006.

STATEMENT OF GOVERNMENTAL INTEREST

This invention was made with government support under a research grant from the National Institutes of Health (NIH), Bethesda, Md., U.S.A., (Grant Numbers AI 16790-21, ES 04050-16, AI 45541, CA09432 and N01-CM97567). The government has certain rights in the invention.

FIELD OF THE INVENTION

The present invention relates to compositions comprising CpG rich DNA from *Pseudomonas aeruginosa* and, optionally, cupredoxins. The present invention includes specific CpG DNAs from *Pseudomonas aeruginosa* that are useful for treating patients, particularly suffering from conditions, specifically cancer, and preventing cancer. These compositions are optionally in a pharmaceutically acceptable carrier and optionally comprise a cupredoxin. The present invention further relates to methods to express proteins near cancer cells. These methods may be used to express therapeutic or diagnostic proteins near cancer cells in a patient suffering from conditions, and specifically cancer, preventing cancer, and diagnosing cancer in a patient. This method uses the gene for azurin from *P. aeruginosa* as an expression system for azurin or heterologous proteins in *P. aeruginosa* or heterologous cells.

BACKGROUND OF THE INVENTION

While the use of live bacteria in DNA vaccination and gene therapy has shown significant potential in cancer therapy, another avenue has been the use of bacterial products such as lipolysaccharides, peptidoglycans or even naked DNA. Vassaux et al., J. Pathol. 208:290-298 (2006). As early as in 1984, the DNA from *Mycobacterium bovis* BCG was shown to have antitumor properties. Indeed, Tokunaga et al. described the isolation of purified DNA from BCG that demonstrated significant tumor regression in mice and substantial regressing response in human skin malignancies. Tokunaga et al., Japan J. Infect. Dis. 52:1-11 (1999).

The immunostimulatory activity leading to tumor regression in the BCG DNA is due to the presence of DNA stretches rich in unmethyalted CpG dinucleotides. Unmethylated CpG sequences are 20 times more common in bacterial DNA as compared to mammalian DNA, and the presence of specific unmethylated CpG sequences (motifs) are recognized by the Toll-like receptor (TLR) 9. This interaction between the bacterial CpG DNA motif and TLR9 activates the monocytes and dendritic cells to produce interleukin-12 which in turn activates the T-helper 1 cells. In contrast to CpG DNA, bacterial lipopolysaccharides are recognized by TLR4 while the corresponding lipoproteins are recognized by TLR2. Modlin, Nature 408:659-660 (2000); Krieg, Nature Med. 9:831-835 (2003). Since the bacterial DNA rich in unmethylated CpG sequences is difficult to purify for human clinical trials, synthetic oligodeoxynucleotides (ODNs) of 8 to 30 bases and containing one or more CpG motifs, have been used with encouraging results in the immunotherapy of viral, bacterial and parasitic infections, as well as in limited phase I human clinical trials in patients with basal cell carcinoma or melanoma. Krieg, Id.

In contrast to bacterial CpG motifs, mammalian cell DNA contains CpG sequences where the cytosine residues are highly methylated. For example, about 6 to 8% of human DNA cytosine residues are believed to be methylated by DNA methyltransferases whose levels are modestly higher in human tumors than in normal cells. The promoter regions of a number of human genes have CpG islands that are hypermethylated leading to silencing of the downstream genes. Such epigenetic silencing of the downstream genes, particularly in tumor suppressor genes such as p16Ink4a, BRCA1 or hMLH1, triggers tumor formation and where development of specific DNA-demethylating agents can serve as antitumor drugs. Herman and Baylin, New Eng. J. Med. 349:2042-2054 (2003); Feinberg and Tycko, Nature Rev. Cancer 4:143-153 (2004). Transcriptional profiling of several breast cancer cell lines has demonstrated the presence of CpG islands that are highly methylated in the primary tumors and in the cell lines but not in the DNA from normal breast epithelia or matched lymphocytes from cancer patients. Treatment of a breast cancer cell line with the DNA methylation inhibitor 5-azacytidine resulted in the growth arrest of the cancer cells, demonstrating the importance of promoter CpG island methylation in tumor growth. Wang et al., Oncogene 24:2705-2714 (2005).

What is needed are new treatments for patients, specifically patients suffering from conditions, and specifically cancer, and preventative treatments for cancer. Such treatments may be new treatment methods, or variations or improvements on previously described treatment methods. Such cancer treatments should be able to slow the growth of tumors in mammalian patients, and/or decrease the size of tumors in mammalian patients. Also needed are methods to deliver therapeutic molecules to cancer cells in a patient as well as diagnose the existence and location of tumors in patients.

SUMMARY OF THE INVENTION

The present invention relates to compositions comprising CpG rich DNA polynucleotides from *Pseudomonas aeruginosa*. Specifically, these compositions may comprise CpG rich DNA from *P. aeruginosa*, and optionally a cupredoxin peptide, such as azurin from *Pseudomonas aeruginosa*, and/or the 50-77 residue region of azurin (p28). The invention further relates to the use of the compositions of the invention to treat patients, particularly mammalian patients suffering from conditions, and specifically cancer, and to prevent cancer. The present invention further relates to cells and methods to express a protein upon contact with cancer cells, and methods to administer the cells to diagnose and treat cancer.

In one aspect of the invention, an isolated nucleic acid molecule comprising a polynucleotide sequence selected from the group consisting of (a) a sequence selected from the group consisting of SEQ ID NOS: 26-62 and (b) a sequence that is at least 90% identical to a sequence selected from the group consisting of SEQ ID NOS: 26-62. In a specific embodiment, the polynucleotide is SEQ ID NO: 26. The isolated nucleic acid sequence may be in a pharmaceutically acceptable carrier. This pharmaceutical composition may also comprise at least one cupredoxin peptide. In some embodiments, the pharmaceutical composition is formulated for intravenous, subcutaneous or topical administration. In some embodiments, the cupredoxin peptide in the pharmaceutical composition may be from an organism selected from the group consisting of *Pseudomonas aeruginosa, Alcaligenes faecalis, Achromobacter xylosoxidan Bordetella bronchiseptica, Methylomonas* sp., *Neisseria meningitidis, Neisseria gonorrhea, Pseudomonas fluorescens, Pseudomonas chlororaphis, Xylella fastidiosa*, and *Vibrio parahaemolyticus*. In some embodiments, the cupredoxin peptide in the pharmaceutical composition may be part or all of a protein selected from the group consisting of an azurin, pseudoazurin, plastocyanin, rusticyanin, Laz, auracyanin, stellacyanin or cucumber basic protein. The pharmaceutical composition may also comprise part of all of a peptide selected from the group consisting of SEQ ID NOS: 1-25.

The present invention also includes methods. Any of the methods according to the present invention can be used to treat a patient suffering from a condition. In certain embodiments of the methods according to the present invention, the patient is suffering from a cancer.

Cancers treated in accordance with the present invention can include, without limitation melanoma, breast, pancreas, glioblastoma, astrocytoma, lung, colorectal, neck and head, bladder, prostate, skin, and cervical cancer.

Administration routes can include, without limitation, intravenous injection, intramuscular injection, subcutaneous injection, inhalation, topical administration, transdermal patch, suppository, vitreous injection and oral.

In one embodiment the method includes a method to treat a patient, comprising administering the patient an isolated nucleic acid molecule comprising a polynucleotide sequence selected from the group consisting of (a) a sequence selected from the group consisting of SEQ ID NOS: 26-62 and (b) a sequence that is at least 90% identical to a sequence selected from the group consisting of SEQ ID NOS: 26-62 wherein the isolated nucleic acid molecule is in a pharmaceutically acceptable carrier and co-administering a cupredoxin peptide.

In another embodiment of the methods according to the present invention, the method comprises administering to the patient a pharmaceutical composition comprising a pharmaceutically acceptable carrier, at least one cupredoxin peptide and an isolated nucleic acid molecule comprising a polynucleotide sequence selected from the group consisting of (a) a sequence selected from the group consisting of SEQ ID NOS: 26-62 and (b) a sequence that is at least 90% identical to a sequence selected from the group consisting of SEQ ID NOS: 26-62.

In another embodiment of the methods according to the present invention, the pharmaceutical composition is administered by a mode selected from the group consisting of intravenous injection, intramuscular injection, subcutaneous injection, inhalation, topical administration, transdermal patch, suppository, vitreous injection and oral.

In another embodiment of the methods according to the present invention, the method comprises administering the patient an isolated nucleic acid molecule comprising a polynucleotide sequence selected from the group consisting of (a) a sequence selected from the group consisting of SEQ ID NOS: 26-62 and (b) a sequence that is at least 90% identical to a sequence selected from the group consisting of SEQ ID NOS: 26-62 wherein the isolated nucleic acid molecule is in a pharmaceutically acceptable carrier and co-administering a cupredoxin peptide and further co-administering an additional prophylactic or therapeutic drug.

The present invention also includes cells. In one embodiment the cell harbors a heterologous gene for azurin from *Pseudomonas aeruginosa*, wherein the cell expresses the azurin upon contact with cancer cells. In another embodiment, the coding sequence for azurin in the heterologous gene for azurin has been replaced with a coding sequence for a target protein, wherein the cell expresses the target protein upon contact with cancer cells. In another embodiment the cell is a *Pseudomonas aeruginosa* cell, wherein the coding sequence for azurin in the genome has been replaced with a coding sequence for a target protein, and which expresses the target protein upon contact with cancer cells. In another embodiment, wherein the coding sequence for azurin in the heterologous gene for azurin has been replaced with a coding sequence for a target protein and wherein the cell expresses the target protein upon contract with cancer cells, the target protein is selected from the group consisting of a prophylactic protein, a therapeutic protein, a cytotoxic protein, and a diagnostic protein.

The present invention also includes methods of using the cells described in the preceding paragraph. In certain of these embodiments, the methods comprise treating a patient by administering one or more of the described cell types. The present invention also includes methods of diagnosing cancer in a patient using the described cell types described in the preceding paragraph. In one embodiment the method includes administering a cell that generally harbors a heterologous gene for azurin from *Pseudomonas aeruginosa*, wherein the cell expresses the azurin upon contact with cancer cells and wherein the coding sequence for azurin in the heterologous gene for azurin has been replaced with a coding sequence for a target protein, wherein the cell expresses the target protein upon contract with cancer cells and wherein the target protein is a diagnostic protein. In other embodiments, the target protein is selected from the group consisting of a prophylactic protein, a therapeutic protein, a cytotoxic protein, and a diagnostic protein. In additional embodiments the pharmaceutical composition can be administered by a mode selected from the group consisting of intravenous injection, intramuscular injection, subcutaneous injection, inhalation, topical administration, transdermal patch, suppository, vitreous injection and oral. Again, with these methods, the patient can be suffering from a condition and/or cancer. These and other aspects, advantages, and features of the invention will become apparent from the following figures and detailed description of the specific embodiments.

BRIEF DESCRIPTION OF THE SEQUENCES

SEQ ID NO: 1. Amino acid sequence of azurin from *Pseudomonas aeruginosa*.

SEQ ID NO: 2. Amino acid sequence of p28, *Pseudomonas aeruginosa* azurin residues 50-77.

SEQ ID NO: 3. Amino acid sequence of plastocyanin from *Phormidium laminosum*.

SEQ ID NO: 4. Amino acid sequence of rusticyanin from *Thiobacillus ferrooxidans*.

SEQ ID NO: 5. Amino acid sequence of pseudoazurin from *Achromobacter cycloclastes*.

SEQ ID NO: 6. Amino acid sequence of azurin from *Alcaligenes faecalis*.

SEQ ID NO: 7. Amino acid sequence of azurin from *Achromobacter xylosoxidans* ssp. *denitrificans* I.

SEQ ID NO: 8. Amino acid sequence of azurin from *Bordetella bronchiseptica*.

SEQ ID NO: 9. Amino acid sequence of azurin from *Methylomonas* sp. J.

SEQ ID NO: 10. Amino acid sequence of azurin from *Neisseria meningitidis* Z2491.

SEQ ID NO: 11. Amino acid sequence of azurin from *Pseudomonas fluorescen*.

SEQ ID NO: 12. Amino acid sequence of azurin from *Pseudomonas chlororaphis*.

SEQ ID NO: 13. Amino acid sequence of azurin from *Xylella fastidiosa* 9a5c.

SEQ ID NO: 14. Amino acid sequence of stellacyanin from *Cucumis sativus*.

SEQ ID NO: 15. Amino acid sequence of auracyanin A from *Chloroflexus aurantiacus*.

SEQ ID NO: 16. Amino acid sequence of auracyanin B from *Chloroflexus aurantiacus*.

SEQ ID NO: 17. Amino acid sequence of cucumber basic protein from *Cucumis sativus*.

SEQ ID NO: 18. Amino acid sequence of Laz from *Neisseria gonorrhoeae* F62.

SEQ ID NO: 19. Amino acid sequence of the azurin from *Vibrio parahaemolyticus*.

SEQ ID NO: 20. Amino acid sequence of amino acids 57 to 89 of auracyanin B of *Chloroflexus aurantiacus*.

SEQ ID NO: 21. Amino acid sequence of amino acids 51-77 of *Bordetella pertussis* azurin.

SEQ ID NO: 22. Amino acid sequence of amino acids 89-115 of *Neisseria meningitidis* Laz.

SEQ ID NO: 23. Amino acid sequence of amino acids 51-77 of *Pseudomonas syringae* azurin.

SEQ ID NO: 24. Amino acid sequence of amino acids 52-78 of *Vibrio parahaemolyticus* azurin.

SEQ ID NO: 25. Amino acid sequence of amino acids 51-77 of *Bordetella bronchiseptica* azurin.

SEQ ID NOS: 26. DNA sequence of polynucleotide in 15 kb band that is released from *P. aerugniosa* that encodes a polypeptide with similarity to Laz from *Neisseria*.

SEQ ID NOS: 27-62. DNA sequences of polynucleotides in 15 kb band that is released from *P. aerugniosa*.

BRIEF DESCRIPTION OF THE FIGURES

FIG. 2A. Strain 8822 cells transformed with plasmid pQF47 containing the lacZ gene were grown in the presence (MCF-7) or absence (control) of cancer cells, and extracellular and intracellular fractions were subjected to SDS-PAGE, followed by Western blotting using anti-LacZ antibody. Sample preparation was carried out as in FIG. 1. Standard LacZ is shown in the left lane. Asterisk indicates the intracellular fraction of the parental strain 8822 cells (without the pQF47 plasmid) incubated for 60 min with cancer cells. FIG. 2B. Extracellular fractions of strain 8822 cells transformed with pQF47 were subjected to SDS-PAGE, followed by Western blotting using anti-azurin antibody. FIG. 2C. Functional expression of LacZ in strain 8822 cells transformed with pQF47.

FIG. 3A, azurin secretion from *E. coli* JM109; FIG. 3B, cytochrome $c_{551}$ secretion form *E. coli* JCB7120; FIG. 3C, azurin secretion from *P. aeruginosa* 8822 when such cells were preincubated for 1 h with 0, 50 or 250 μM CCCP. FIG. 3D, azurin secretion from *E. coli* JM109 when such cells were preincubated with CCCP at 250 μM concentrations for 1 h before being exposed or not exposed to MCF-7 breast cancer cells. FIG. 3E, effect of CCCP on the growth of *P. aeruginosa* 8822 (left panel) and *E. coli* JM109 (right panel) cells. CCCP at the concentrations indicated were added in early to mid exponential phase of growth and the growth rate was followed for the next 60 min at an optical density of 600 nm.

FIG. 4A, *P. aeruginosa* 8822 strain secretes a 15 kb extrachromosomal DNA fragment. The DNA is purified from the culture medium filtrate by isopropanol precipitation of the nucleoprotein fractions followed by DNA purification through QIAGEN columns (Qiagen, Inc., Valencia Calif.). FIG. 4B, Extrachromosomal DNA secretion at different time points. The DNA is secreted as early as 5 min and the secretion is enhanced at 15, 30 and 60 min respectively. The DNA is efficiently secreted at all time points in the presence of MCF-7 human breast cancer cells. FIG. 4C, *Pseudomonas aeruginosa* strain 8822 secretes both azurin and the 15 kb DNA fragment into the culture medium filtrate in the presence of MCF-7 cancer cells. Strain 8822 was grown in the presence of the MCF-7 cancer cells and the secretion of azurin and extrachromosomal DNA in the extracellular fraction was examined by Western blotting using anti-azurin antibody and PCR using primers for PA clone and the precipitated DNA as template. The secretion of azurin and the DNA is time dependent. FIG. 4D, the secreted DNA is CpG rich. The DNA is subjected to restriction endonuclease digestion by EcoR1, HindIII, MspI and PvuI enzymes. MspI and PvuI, known to cut CpG-rich DNA, generates a smear of DNA bands indicating the presence of high ratio of CG sequences in the DNA.

FIG. 5A, this stretch of DNA (SEQ ID NO: 49) has no homology with any other sequence in the database and does not appear to be part of an open reading frame. FIG. 5B, comparative amino acid sequence homology of the putative azurin gene present in the CpG-rich released DNA (8822) (SEQ ID NO: 63) and the corresponding sequence from *P. aeruginosa* PAO1 (SEQ ID NO: 66) and *Neisseria gonorrhoeae* (NG) (SEQ ID NO: 64) and *N. meningitidis* (NM) (SEQ ID NO: 65).

FIG. 7 is a table of the CpG rich DNA sequences released from *P. aeruginosa* upon contact with cancer cells.

DETAILED DESCRIPTION OF THE INVENTION

Definitions

Figures 1, 1A:
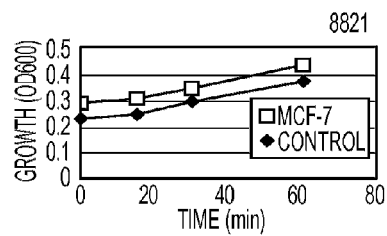
FIG. 1 depicts the secretion of azurin by *P. aeruginosa* strains 8821 and 8822 in the presence of cancer cells.
FIG. 1A. Two *P. aeruginosa* strains (8822, 8821) were grown in the presence (MCF-7) or absence (control) of cancer cells, and the secretion of azurin in the extracellular fraction was examined by Western blotting using anti-azurin antibody. Panel a: growth of *P. aeruginosa* cells by measurement of turbidity at 600 nm. Squares and diamonds indicate the secretion level of azurin in the presence and absence of cancer cells respectively. The difference in the turbidity at 0 min between the presence and absence of cancer cells is due to the addition of cancer cells. Panel b: diagrammatic representation of the secretion level of azurin by measurement of the signal intensity on Western blotting profiles. Squares and diamonds indicate the secretion level of azurin in the presence and absence of cancer cells respectively. Panel c: western blotting. Extracellular fractions were prepared at 0, 15, 30 and 60 min after the addition of cancer cells and then subjected to SDS-PAGE, followed by Western blotting. Arrows indicate the position of azurin.

As used herein, the term "cell" includes either the singular or the plural of the term, unless specifically described as a "single cell."

As used herein, the terms "polypeptide," "peptide," and "protein" are used interchangeably to refer to a polymer of amino acid residues. The terms apply to amino acid polymers in which one or more amino acid residue is an artificial chemical analogue of a corresponding naturally occurring amino acid. The terms also apply to naturally occurring amino acid polymers. The terms "polypeptide," "peptide," and "protein" are also inclusive of modifications including, but not limited to, glycosylation, lipid attachment, sulfation, gamma-carboxylation of glutamic acid residues, hydroxylation and ADP-ribosylation. It will be appreciated that polypeptides are not always entirely linear. For instance, polypeptides may be branched as a result of ubiquitination and they may be circular (with or without branching), generally as a result of post-translation events, including natural processing event and events brought about by human manipulation which do not occur naturally. Circular, branched and branched circular polypeptides may be synthesized by non-translation natural process and by entirely synthetic methods as well.

As used herein, the terms "polynucleotide," "oligonucleotide," "oligo," and "DNA" are used interchangeably to refer to a polymer of nucleic acid residues.

As used herein, the term "pharmacologic activity" means the effect of a drug or other chemical on a biological system. The effect of chemical may be beneficial (therapeutic) or harmful (toxic). The pure chemicals or mixtures may be of natural origin (plant, animal, or mineral) or may be synthetic compounds.

As used herein, the term "pathological condition" includes anatomic and physiological deviations from the normal that constitute an impairment of the normal state of the living animal or one of its parts, that interrupts or modifies the performance of the bodily functions, and is a response to various factors (as malnutrition, industrial hazards, or climate), to specific infective agents (as worms, parasitic protozoa, bacteria, or viruses), to inherent defects of the organism (as genetic anomalies), or to combinations of these factors.

As used herein, the term "condition" includes anatomic and physiological deviations from the normal that constitute an impairment of the normal state of the living animal or one of its parts, that interrupts or modifies the performance of the bodily functions.

As used herein, the term "suffering from" includes presently exhibiting the symptoms of a pathological condition, having a pathological condition even without observable symptoms, in recovery from a pathological condition, or recovered from a pathological condition.

A used herein, the term "treatment" includes preventing, lowering, stopping, or reversing the progression or severity of a condition or symptoms associated with a condition being treated. As such, the term "treatment" includes medical, therapeutic, and/or prophylactic administration, as appropriate. Treatment may also include preventing or lessening the development of a condition, such as cancer.

As used herein, the term "inhibit cell growth" means the slowing or ceasing of cell division and/or cell expansion. This term also includes the inhibition of cell development or increases in cell death.

A "therapeutically effective amount" is an amount effective to prevent, lower, stop or reverse the development of, or to partially or totally alleviate the existing symptoms of a particular condition for which the subject being treated. Determination of a therapeutically effective amount is well within the capability of those skilled in the art.

The term "substantially pure," as used herein, when used to modify a protein or other cellular product of the invention, refers to, for example, a protein isolated from the growth medium or cellular contents, in a form substantially free of, or unadulterated by, other proteins and/or other compounds. The term "substantially pure" refers to a factor in an amount of at least about 75%, by dry weight, of isolated fraction, or at least "75% substantially pure." More specifically, the term "substantially pure" refers to a compound of at least about 85%, by dry weight, of isolated fraction, or at least "85% substantially pure." Most specifically, the term "substantially pure" refers to a compound of at least about 95%, by dry weight, of isolated fraction, or at least "95% substantially pure." The term "substantially pure" may also be used to modify a synthetically-made protein or compound of the invention, where, for example, the synthetic protein is isolated from the reagents and by-products of the synthesis reaction(s).

The term "pharmaceutical grade," as used herein, when referring to a peptide or compound of the invention, is a peptide or compound that is isolated substantially or essentially from components which normally accompany the material as it is found in its natural state, including synthesis reagents and by-products, and substantially or essentially isolated from components that would impair its use as a pharmaceutical. For example, a "pharmaceutical grade" peptide may be isolated from any carcinogen. In some instances, "pharmaceutical grade" may be modified by the intended method of administration, such as "intravenous pharmaceutical grade," in order to specify a peptide or compound that is substantially or essentially isolated from any substance that would render the composition unsuitable for intravenous administration to a patient. For example, an "intravenous pharmaceutical grade" peptide may be isolated from detergents, such as SDS, and anti-bacterial agents, such as azide.

The terms "isolated," "purified" or "biologically pure" refer to material which is substantially or essentially free from components which normally accompany the material as it is found in its native state. Thus, isolated polynucleotides or peptides in accordance with the invention preferably do not contain materials normally associated with the polynucleotides or peptides in their in situ environment. An "isolated" region of a polynucleotides or polypeptide refers to a region that does not include the whole sequence of the polynucleotides or polypeptide from which the region was derived. An "isolated" nucleic acid, protein, or respective fragment thereof has been substantially removed from its in vivo environment so that it may be manipulated by the skilled artisan, such as but not limited to, nucleotide sequencing, restriction digestion, site-directed mutagenesis, and subcloning into expression vectors for a nucleic acid fragment as well as obtaining the protein or protein fragment in substantially pure quantities.

The term "variant" as used herein with respect to a peptide, refers to amino acid sequence variants which may have amino acids replaced, deleted, or inserted as compared to the wild-type polypeptide. Variants may be truncations of the wild-type peptide. A "deletion" is the removal of one or more amino acids from within the polypeptide, while a "truncation" is the removal of one or more amino acids from one or both ends of the polypeptide. Thus, a variant peptide may be made by manipulation of genes encoding the polypeptide. A variant may be made by altering the basic composition or characteristics of the polypeptide, but not at least some of its pharmacologic activities. For example, a "variant" of azurin can be a mutated azurin that retains its ability to inhibit the development of premalignant mammalian cells. In some cases, a variant peptide is synthesized with non-natural amino acids, such as ε-(3, 5-dinitrobenzoyl)-Lys residues. Ghadiri & Fernholz, J. Am. Chem. Soc., 112:9633-9635 (1990). In some embodiments, the variant has not more than 20 amino acids replaced, deleted or inserted compared to wild-type peptide or part thereof. In some embodiments, the variant has not more than 15 amino acids replaced, deleted or inserted compared to wild-type peptide or part thereof. In some embodiments, the variant has not more than 10 amino acids replaced, deleted or inserted compared to wild-type peptide or part thereof. In some embodiments, the variant has not more than 6 amino acids replaced, deleted or inserted compared to wild-type peptide or part thereof. In some embodiments, the variant has not more than 5 amino acids replaced, deleted or inserted compared to wild-type peptide or part thereof. In some embodiments, the variant has not more than 3 amino acids replaced, deleted or inserted compared to wild-type peptide or part thereof.

The term "amino acid," as used herein, means an amino acid moiety that comprises any naturally-occurring or non-naturally occurring or synthetic amino acid residue, i.e., any moiety comprising at least one carboxyl and at least one amino residue directly linked by one, two three or more carbon atoms, typically one (a) carbon atom.

The term "derivative" as used herein with respect to a peptide refers to a peptide that is derived from the subject peptide. A derivation includes chemical modifications of the peptide such that the peptide still retains some of its fundamental activities. For example, a "derivative" of azurin can, for example, be a chemically modified azurin that retains its ability to inhibit angiogenesis in mammalian cells. Chemical modifications of interest include, but are not limited to, amidation, acetylation, sulfation, polyethylene glycol (PEG) modification, phosphorylation or glycosylation of the peptide. In addition, a derivative peptide may be a fusion of a polypeptide or fragment thereof to a chemical compound, such as but not limited to, another peptide, drug molecule or other therapeutic or pharmaceutical agent or a detectable probe.

The term "percent (%) nucleotide sequence identity" is defined as the percentage of nucleotides in a polynucleotide that are identical with nucleotides in a candidate sequence when the two sequences are aligned. To determine % nucleotide identity, sequences are aligned and if necessary, gaps are introduced to achieve the maximum % sequence identity. Nucleotide sequence alignment procedures to determine percent identity are well known to those of skill in the art. Often publicly available computer software such as BLAST, BLAST2, ALIGN2 or Megalign (DNASTAR) software is used to align nucleotide sequences. In a specific embodiment, Blastn (available from the National Center for Biotechnology Information, Bethesda Md.) may be used using the default parameters of low complexity filter, expect 10, and word size 11.

The term "host cell" includes an individual cell or cell culture which can be or has been a recipient of any recombinant vector(s) or isolated polynucleotide of the invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention. A host cell which comprises a recombinant vector of the invention is a "recombinant host cell".

The term "transformation" is used interchangeably with "genetic modification" and refers to a permanent or transient genetic change induced in a cell following introduction of new DNA (i.e., DNA exogenous to the cell). Genetic change ("modification") can be accomplished either by incorporation of the new DNA into the genome of the host cell, or by transient or stable maintenance of the new DNA as an episomal element.

When amino acid sequences are aligned, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) can be calculated as:

% amino acid sequence identity=$X/Y*100$ where
X is the number of amino acid residues scored as identical matches by the sequence alignment program's or algorithm's alignment of A and B and
Y is the total number of amino acid residues in B.

If the length of amino acid sequence A is not equal to the length of amino acid sequence B, the % amino acid sequence identity of A to B will not equal the % amino acid sequence identity of B to A. When comparing longer sequences to shorter sequences, the shorter sequence will be the "B" sequence. For example, when comparing truncated peptides to the corresponding wild-type polypeptide, the truncated peptide will be the "B" sequence.

When nucleotide sequences are aligned, the % nucleotide sequence identity of a given nucleotide sequence A to, with, or against a given nucleotide sequence B (which can alternatively be phrased as a given nucleotide sequence A that has or comprises a certain % nucleotide sequence identity to, with, or against a given nucleotide sequence B) can be calculated as:

% nucleotide sequence identity=$X/Y*100$ where
X is the number of nucleotide residues scored as identical matches by the sequence alignment program's or algorithm's alignment of A and B and
Y is the total number of nucleotide residues in B.

If the length of nucleotide sequence A is not equal to the length of nucleotide sequence B, the % nucleotide sequence identity of A to B will not equal the % nucleotide sequence identity of B to A. When comparing longer sequences to shorter sequences, the shorter sequence will be the "B" sequence. For example, when comparing a region of a polynucleotide to the corresponding full-length polynucleotide, the region of the polynucleotide will be the "B" sequence.

General

The present invention provides compositions comprising isolated polynucleotides comprising CpG rich DNA from *Pseudomonas aeruginosa*. The invention also provides pharmaceutical compositions comprising CpG rich DNA from *Pseudomonas aeruginosa*, and optionally at least one cupredoxin peptide, which may be advantageously used to treat patients, specifically patients suffering from a condition, and specifically cancer, or to prevent cancer. The invention further provides methods to treat patients, specifically patients suffering from conditions, specifically cancer, or to prevent cancer, comprising administering the CpG rich DNA from *P. aeruginosa* optionally in combination with a cupredoxin peptide. The present also provides cells that are induced to express specific proteins when in contact with cancer cells using the azurin gene from *P. aeruginosa*. These cells maybe used in methods to treat a patient, specifically suffering from a condition, specifically cancer, or to prevent cancer, or to diagnose cancer in a patient.

Relating to a first aspect of the invention, it was previously known that a redox protein elaborated by *Pseudomonas aerugisnosa*, the cupredoxin azurin, selectively enters J774 lung cancer cells but not normal cells, and induces apoptosis. Zaborina et al., Microbiology 146:2521-2530 (2000). Azurin can also selectively enter and kill human melanoma UISO-Mel-2 or human breast cancer MCF-7 cells. Yamada et al., PNAS 99:14098-14103 (2002); Punj et al., Oncogene 23:2367-2378 (2004). Azurin from *P. aeruginosa* preferentially enters J774 murine reticulum cell sarcoma cells, forms a complex with and stabilizes the tumor suppressor protein p53, enhances the intracellular concentration of p53, and induces apoptosis. Yamada et al., Infection and Immunity 70:7054-7062 (2002). Detailed studies of various domains of the azurin molecule showed that amino acids 50-77 (p28) (SEQ ID NO: 2) represented a protein transduction domain (PTD) critical for internalization and subsequent apoptotic activity. Yamada et al., Cell. Microbial. 7:1418-1431 (2005).

It is now known that *Pseudomonas aeruginosa* also releases specific DNA sequences into the extracellular medium, in a manner enhanced by the presence of cancer cells. See Example 5. This DNA is released from *P. aeruginosa* as soon as 5 minutes after contact with cancer cells, suggesting that the released DNA is extrachromosomal in origin. See Example 6. Digestion of the released DNA with restriction enzymes indicates that the DNA is rich in G+C nucleotides, and thus is "CpG-rich DNA." See Example 7. Among the DNA sequences found among the released DNA is a sequence, SEQ ID NO: 26, that is CpG rich and is 95% identical to the nucleotide sequence from the azurin gene from *Neisseria*, laz. See Example 8. Finally, this *P. aeruginosa* CpG rich DNA preparation is now known to have anti-tumor properties, as documented by its ability to activate NF-kB in a TLR9-dependent manner. See Example 9.

It is contemplated that the *P. aeruginosa* CpG rich DNA may be administered with cupredoxins to treat patients, specifically suffering from a condition, specifically cancer, or to prevent cancer. Specifically, it is contemplated that the polynucleotide released from *P. aeruginosa* with the sequence that is very similar to the Neisserial laz gene, SEQ ID NO: 26, may be coadministered with a cupredoxin, such as azurin from *Pseudomonas aeruginosa*, and/or the 50-77 residue region of azurin (p28), to improve the efficaciousness of cupredoxin alone on treating patients with cancer, AIDS, malaria, inappropriate angiogenesis or at risk of developing cancer. While not limiting the function of this treatment method to any one means, it is contemplated that the CpG rich DNA released by *P. aeruginosa* will decrease the degree by which the immune system of the patient attacks the co-administered cupredoxin peptide. It is contemplated that *P. aeruginosa* has evolved as a parasite on mammalian species, and that tumor growth on the mammalian species inhibits the growth of *P. aeruginosa*. Further, it is thought that *P. aeruginosa* actively secretes azurin on exposure to cancer cells as a weapon against cancer. Since azurin can be targeted by the host immune system for antibody formation, it is contemplated that *P. aeruginosa* strain 8822 has also evolved CpG-rich DNA by to be released upon exposure to cancer cells so that it can be used as a decoy to divert the attention of the immune system from targeting azurin. Because the CpG rich DNA is thought to protect an optionally co-administered cupredoxin, it will be effective in improving the efficaciousness of any treatment method relating to administering a cupredoxin, regardless of the disease or condition being treated. It is further contemplated that the CpG rich DNA is useful in protecting any co-administered chemical compound from targeting by the immune system.

Relating to the second aspect of the invention, it was previously known that azurin from *Pseudomonas aeruginosa* is a periplasmic protein which is secreted in the growth medium at the late stage of growth. Zaborina et al., Microbiology 146:2521-2530 (2000). Its extracellular release is dependent on quorum sensing at high cell density and modulated by GacA or the two small RNA products RsmY and RsmZ. Kay et al., J. Bacteriol. 188:6026-6033 (2006).

It is now known that the presence of human cancer cells induces *P. aeruginosa* to release azurin into the extracellular medium. In the presence of cancer cell lines MCF-7 and Mel-2, *P. aeruginosa* released azurin into the medium within 20 to 30 min of exposure to the cancer cells, but no secretion was observed in the absence of the cancer cells. See Example 1. Further, this release of azurin was not due to cell lysis, and required the actual presence of the cancer cells, in contrast to diffusible factors from the cancer cells. See Example 2. Further, it is now known that cancer cells will also induce the release of azurin from *E. coli* harboring the *P. aeruginosa* azurin gene. See Example 3. Finally, energy is not required to release azurin from *P. aeruginosa* or *E. coli*. See Example 4.

Live cells of *M. bovis* are widely used today in the treatment for superficial bladder cancer, and the use of attenuated bacteria in the potential therapy against cancer is attracting wide attention. Chakrabarty, J. Bacterial. 185: 2683-2686 (2003); Minton, Nature Rev. Microbiol. 1:237-243 (2003); Dang et al., Cancer Biol. Therap., 3:326-337 (2004); Vassaux et al., J. Pathol. 208:290-298 (2006). It is contemplated that the azurin gene from *P. aeruginosa* can be used in *P. aeruginosa* or in another cell, such as *E. coli*, to express azurin or a heterologous protein when in contact with cancer cells. A cell harboring the azurin gene expressing azurin or a heterologous protein will be useful to treat cancer by delivering the expressed protein to the site of the cancer cells, or to provide a means by which the location of cancer could be diagnosed by the expression of the protein.

Compositions of the Invention

The invention provides for isolated polynucleotides that are released from *P. aeruginosa* and that are useful for treating patients, specifically suffering from conditions, and specifically cancer. In some embodiments, the isolated polynucleotides are CpG rich DNA. In some embodiments, the isolated polynucleotides are those released by *P. aeruginosa* upon contact with cancer cells and prepared according to the procedure provided in Example 5. In other embodiments, the isolated CpG rich DNA may comprise one or more isolated polynucleotides with the sequences provided in SEQ ID NOS: 26-62. In specific embodiments, the isolated CpG rich DNA comprises isolated polynucleotides with the sequence in SEQ ID NO: 26. In other specific embodiments, the CpG rich DNA consists of an isolated polynucleotide with the sequence in SEQ ID NOS: 26-62.

The invention provides compositions comprising isolated CpG rich DNA from *P. aeruginosa*, optionally with at least one isolated cupredoxin peptide. In some embodiments, these compositions also comprise a pharmaceutically acceptable carrier. In specific embodiments, the composition is designed for a particular mode of administration, for example, but not limited to, oral, intraperitoneal, or intravenous. Such compositions may be hydrated in water, or may be dried (such as by lyophilization) for later hydration. Such compositions may be in solvents other than water, such as but not limited to, alcohol.

The CpG rich DNA may be in the form of stabilized DNA. In one embodiment, the DNA can be stabilized by condensing the DNA via treatment with calcium chloride in 20% (v/v) tert-butanol, so as to form small (about 50 nm) toroids as well as larger (about 300 nm) rods and spheres i.e. condensed particles of DNA. The condensed particles retain a negative surface charge, indicating sub-stoichiometric concentrations of calcium. More particularly, in one embodiment, purified deionized DNA at a concentration of about 0.1 µg/mL to about 1 mg/mL can be dissolved in an aqueous solution of t-butanol ranging in concentration from about 17% to about 25% (v/v). An appropriate divalent cation consisting of $Ca^{+2}$, $Mg^{+2}$, or $Zn^{2+}$ at concentrations of about 0.2 mM to about 2 mM can then be added to the t-butanol cosolvent solution to condense the DNA. In one embodiment, the stoichiometric ratio of anionic phosphates of the DNA backbone to divalent cations is between (anions/cations) about 0.1 and about 1.0, with about 0.3 being a most preferred ratio. The solution can then be allowed to equilibrate, for about 45 minutes to permit thermodynamic equilibrium condensation to be attained. The rods, toroids, and spherical DNA particulates will fall in the size range of about 20 to about 500 nm. The solution containing the condensed DNA can then be transferred to downstream process unit operations, such as, without limitation, sterile filtration through 0.22 um filters, spray-drying, or lyophilization.

The sterile filtered condensed DNA can then be processed by lyophilization or spray-drying to obtain stable pharmaceutical dosage forms. Prior to lyophilization the DNA can be combined with bulking agents such as sucrose, mannitol, trehalose, lactose, or other common bulking agents. The t-butanol solution freezes and forms a single phase amenable to lyophilization due to the sublimation properties of t-butanol. In the dried lyophilized cake the DNA toroids and rods remain intact. Upon reconstitution the lyophile cake may rapidly dissolve and the DNA becomes completely solubilized into uncondensed native plasmid DNA ready for dosing with the only traces of the original process being the cations and any added bulking agents. It is substantially free of t-butanol at this stage of the process.

An alternate approach to processing the DNA is to utilize spray drying. Spray drying may involve three fundamental unit processes: liquid atomization, gas-droplet mixing, and drying from liquid droplets. Atomization is accomplished usually by one of three atomizing devices: high-pressure nozzles, two-fluid nozzles, and high-speed centrifugal disks. With these atomizers, thin solutions may be dispersed into droplets as small as about 2 µm. The largest drop sizes rarely exceed about 500 µm (35 mesh). Because of the large total drying surface and small droplet sizes created, the actual drying time in a spray dryer is typically not more than about 30 seconds.

One of the principal advantages of spray drying is the production of a spherical particle, which is usually not obtainable by any other drying methods. The spherical particle may be solid or hollow, depending on the material, the feed condition, and the drying conditions. Because of the high heat-transfer rates to the drops, the liquid at the center of the particle vaporizes, causing the outer shell to expand and form a hollow sphere.

The dried DNA particles can be used as a powdered form of the DNA ready to be reconstituted into a hydrating solution for parenteral administration including, but not limited to intravenous, intramuscular and intraperitoneal administration. The reconstituted DNA can also be administered subcutaneously and intraocularly. The reconstituted DNA can also be administered by aerosol means and can be delivered in a dried particulate form directly in a powder by aerosol or other inhalatory administration means. The composition of powdered DNA for dosing is substantially free of the solvents used to modify its structure.

The isolated polynucleotide may be similar but not identical to one or more of the DNA sequences found in the DNA released by *P. aeruginosa* upon contact with cancer cells. In one embodiment, the isolated polynucleotide may have more than about 80% nucleotide sequence identity with one or more of SEQ ID NOS: 26-62. In another embodiment, the isolated polynucleotide may have more than about 90% nucleotide sequence identity with one or more of SEQ ID NOS: 26-62. In another embodiment, the isolated polynucleotide may have more than about 95% nucleotide sequence identity with one or more of SEQ ID NOS: 26-62.

The compositions of the invention may further comprise a cupredoxin peptide which has anti-tumor activity or other pharmacologic activity of interest. Cupredoxin peptides may be cupredoxins, variants, derivatives or structural equivalents thereof, as provided in U.S. Pat. No. 7,084,105, U.S. Patent Application Publication No. 20060040269, published Feb. 23, 2006, now U.S. Pat. No. 7,491,394; U.S. Patent Application Publication No. 20060149037, published Jul. 6, 2006, now U.S. Pat. No. 7,691,383; U.S. Patent Application Publication No. 20080213185, published Sep. 4, 2008, now U.S. Pat. No. 7,807,183; U.S. Patent Application Publication No. 20080089878, published Apr. 17, 2008, now U.S. Pat. No. 7,381,701; U.S. Patent Application Publication No. 20080103087, published May 1, 2008, now U.S. Pat. No. 7,556,810; U.S. Patent Application Publication No. 20060251669, now U.S. Pat. No. 7,338,766; U.S. Patent Application Publication No. 20060251639, published Nov. 9, 2006, now U.S. Pat. No. 7,301,010; U.S. Patent Application Publication No. 20100267608, published Oct. 21, 2010; and U.S. Patent Application Publication No. 20080139471, published Jun. 12, 2008, now U.S. Pat. No. 7,618,939, each of which is incorporated herein by reference. In specific embodiments, the cupredoxin peptide may have at least one pharmacologic activity of a cupredoxin. Specific pharmacologic activities of interest include (1) entering a mammalian cancer cell, (2) not entering non-cancerous mammalian cells, (3) entering pre-malignant mammalian cells, (4) killing mammalian cancer cells, (5) killing pre-malignant mammalian cells, (6) inhibiting the growth of a mammalian cancer cell, (7) inhibiting HIV-1 infection, (8) inhibiting parasitemia of malaria-infected red blood cells, (9) interfering with the ephrin signaling system, (10) inhibiting angiogenesis and (11) inhibiting the development of premalignant lesions.

The cupredoxin peptide may be a full length wild-type cupredoxin, or variants, derivatives or structural equivalents of cupredoxin that exhibit one or more of the pharmacologic activities in mammalian cells, tissues and/or animals. In some embodiments, the cupredoxin peptide is isolated. In some embodiments, the cupredoxin peptide is substantially pure or pharmaceutical grade. In other embodiments, the cupredoxin peptide is in a composition that comprises, or consists essentially of, the peptide. In another specific embodiment, the cupredoxin peptide does not raise an immune response in a mammal, and more specifically a human. In some embodiments, the cupredoxin peptide is less than a full length cupredoxin, and retains some of the pharmacologic activities of the cupredoxins.

Because of the high structural homology between the cupredoxins, it is contemplated that cupredoxin peptides will have the same pharmacologic activity as p28 (SEQ ID NO: 2). In some embodiments, the cupredoxin peptide is, but is not limited to, azurin, pseudoazurin, plastocyanin, rusticyanin, auracyanin or Laz. In particularly specific embodiments, the azurin is derived from *Pseudomonas aeruginosa, Alcaligenes faecalis, Achromobacter xylosoxidans* ssp. *denitrificans* I, *Bordetella bronchiseptica, Methylomonas* sp., *Neisseria meningitidis, Neisseria gonorrhea, Pseudomonas fluorescens, Pseudomonas chloraphis, Xylella fastidiosa* or *Vibrio parahaemolyticus*. In a very specific embodiment, the azurin is from *Pseudomonas aeruginosa*. In other specific embodiments, the cupredoxin peptide comprises an amino acid sequence that is SEQ ID NO: 1, 3-19.

The cupredoxin peptides may be amino acid sequence variants which have amino acids replaced, deleted, or inserted as compared to the wild-type cupredoxin. The cupredoxin peptides may be truncations of the wild-type cupredoxin. In some embodiments, the cupredoxin peptide comprises a region of a cupredoxin that is less than the full length wild-type polypeptide. In some embodiments, the cupredoxin peptide comprises more than about 10 residues, more than about 15 residues or more than about 20 residues of a truncated cupredoxin. In some embodiments, the cupredoxin peptide comprises not more than about 100 residues, not more than about 50 residues, not more than about 40 residues, not more than about 30 residues or not more than about 20 residues of a truncated cupredoxin. In some embodiments, a cupredoxin has to the cupredoxin peptide, and more specifically SEQ ID NOS: 1-19, at least about 70% amino acid sequence identity, at least about 80% amino acid sequence identity, at least about 90% amino acid sequence identity, at least about 95% amino acid sequence identity or at least about 99% amino acid sequence identity.

In specific embodiments, the cupredoxin peptide comprises *P. aeruginosa* azurin residues 50-77, azurin residues 50-67, or azurin residues 36-88. In other embodiments, the cupredoxin peptide consists of *P. aeruginosa* azurin residues 50-77, azurin residues 50-67, or azurin residues 36-88. In other specific embodiments, the cupredoxin peptide consists of the equivalent residues of a cupredoxin other than azurin. It is also contemplated that other cupredoxin peptides can be designed that have a similar activity to azurin residues 50-77, azurin residues 50-67, or azurin residues 36-88. To do this, the subject cupredoxin amino acid sequence will be aligned to the *Pseudomonas aeruginosa* azurin sequence using BLAST, BLAST2, ALIGN2 or Megalign (DNASTAR), the relevant residues located on the *P. aeruginosa* azurin amino acid sequence, and the equivalent residues found on the subject cupredoxin sequence, and the equivalent cupredoxin peptide thus designed.

In one embodiment of the invention, the cupredoxin peptide contains at least amino acids 57 to 89 of auracyanin B of *Chloroflexus aurantiacus* (SEQ ID NO: 20). In another embodiment of the invention, the cupredoxin peptide contains at least amino acids 51-77 of *Bordetella pertussis* azurin (SEQ ID NO: 21). In another embodiment of the invention, the cupredoxin peptide contains at least amino acids 51-77 of *Pseudomonas syringae* azurin (SEQ ID NO: 23). In another embodiment of the invention, the cupredoxin peptide contains at least amino acids 89-115 of *Neisseria meningitidis* Laz (SEQ ID NO: 22). In another embodiment of the invention, the cupredoxin peptide contains at least amino acids 52-78 of *Vibrio parahaemolyticus* azurin (SEQ ID NO: 24). In another embodiment of the invention, the cupredoxin peptide contains at least amino acids 51-77 of *Bordetella bronchiseptica* azurin (SEQ ID NO: 25).

The cupredoxin peptides also include peptides made with synthetic amino acids not naturally occurring. For example, non-naturally occurring amino acids may be integrated into the cupredoxin peptide to extend or optimize the half-life of the composition in the bloodstream. Such variants include, but are not limited to, D,L-peptides (diastereomer), (for example Futaki et al., J. Biol. Chem. 276(8):5836-40 (2001); Papo et al., Cancer Res. 64(16):5779-86 (2004); Miller et al, Biochem. Pharmacol. 36(1):169-76, (1987); peptides containing unusual amino acids (for example Lee et al., J. Pept. Res. 63(2):69-84 (2004)), olefin-containing non-natural amino acid followed by hydrocarbon stapling (for example Schafmeister et al., J. Am. Chem. Soc. 122:5891-5892 (2000); Walenski et al., Science 305:1466-1470 (2004)), and peptides comprising ε-(3,5-dinitrobenzoyl)-Lys residues.

In other embodiments, the cupredoxin peptide is a derivative of a cupredoxin. The derivatives of cupredoxin are chemical modifications of the peptide such that the peptide still retains some of its fundamental activities. For example, a "derivative" of azurin can be a chemically modified azurin that retains its ability to kill mammalian cancer cells, tissues or animals. Chemical modifications of interest include, but are not limited to, hydrocarbon stabling, amidation, acetylation, sulfation, polyethylene glycol (PEG) modification, phosphorylation and glycosylation of the peptide. In addition, a cupredoxin peptide may be a fusion of a cupredoxin peptide to a chemical compound, such as but not limited to, another peptide, drug molecule or other therapeutic or pharmaceutical agent or a detectable probe. Derivatives of interest include chemical modifications by which the half-life in the bloodstream of the peptides and compositions of the invention can be extended or optimized, such as by several methods well known to those in the art, including but not limited to, circularized peptides (for example Monk et al., BioDrugs 19(4):261-78, (2005); DeFreest et al., J. Pept. Res. 63(5):409-19 (2004)), N- and C-terminal modifications (for example Labrie et al., Clin. Invest. Med. 13(5):275-8, (1990)), and olefin-containing non-natural amino acid followed by hydrocarbon stapling (for example Schafmeister et al., J. Am. Chem. Soc. 122:5891-5892 (2000); Walenski et al., Science 305:1466-1470 (2004)).

In addition, a cupredoxin peptide may be a fusion of a cupredoxin peptide to a cargo, such as a chemical compound, including but not limited to, another peptide, drug molecule or other therapeutic or pharmaceutical agent or a detectable probe. In one embodiment, a detectable substance, for example, a fluorescent substance, such as green fluorescent protein; a luminescent substance; an enzyme, such as β-galactosidase; or a radiolabelled or biotinylated protein is delivered to confer a detectable phenotype to a cell. Similarly, microparticles or nanoparticles labeled with a detectable substance, for example, a fluorescent substance, can be delivered. One example of suitable nanoparticles is found in U.S. Pat. No. 6,383,500, issued May 7, 2002, which is expressly incorporated by reference herein. Many such detectable substances are known to those skilled in the art.

In some embodiments, the cargo compound is a detectable substance that is suitable for X-ray computed tomography, magnetic resonance imaging, ultrasound imaging or radionuclide scintigraphy. In these embodiments, the cargo compound is administered to the patient for purposes of diagnosis. A contrast agent is administered as a cargo compound to enhance the image obtained by X-ray CT, MRI and ultrasound. The administration of a radionuclide cargo compound that is targeted to tumor tissue via the cupredoxin entry domain can be used for radionuclide scintigraphy. In some embodiments, the cupredoxin entry domain may contain the radionucleotide with or without a cargo compound. In other embodiments, the cargo compound is a gamma ray or positron emitting radioisotope, a magnetic resonance imaging contrast agent, an X-ray contrast agent, or an ultrasound contrast agent.

Ultrasound contrast agents suitable for use as cargo compounds include, but are not limited to, a microbubble of a biocompatible gas, a liquid carrier, and a surfactant microsphere, further comprising an optional linking moiety, L., between the targeting moieties and the microbubble. In this context, the term liquid carrier means aqueous solution and the term surfactant means any amphiphilic material which produces a reduction in interfacial tension in a solution. A list of suitable surfactants for forming surfactant microspheres is disclosed in EP0727225A2, herein expressly incorporated by reference. The term surfactant microsphere includes nanospheres, liposomes, vesicles and the like. The biocompatible gas can be air, or a fluorocarbon, such as a $C_3$-$C_5$ perfluoroalkane, which provides the difference in echogenicity and thus the contrast in ultrasound imaging. The gas is encapsulated or contained in the microsphere to which is attached the cupredoxin entry domain, optionally via a linking group. The attachment can be covalent, ionic or by van der Waals forces. Specific examples of such contrast agents include lipid encapsulated perfluorocarbons with a plurality of tumor neovasculature receptor binding peptides, polypeptides or peptidomimetics.

X-ray contrast agents suitable for use as cargo compounds include, but are not limited to, one or more X-ray absorbing or "heavy" atoms of atomic number 20 or greater, further comprising an optional linking moiety, L., between the cupredoxin entry domain and the X-ray absorbing atoms. The frequently used heavy atom in X-ray contrast agents is iodine. Recently, X-ray contrast agents comprised of metal chelates (e.g., U.S. Pat. No. 5,417,959) and polychelates comprised of a plurality of metal ions (e.g., U.S. Pat. No. 5,679,810) have been disclosed. More recently, multinuclear cluster complexes have been disclosed as X-ray contrast agents (e.g., U.S. Pat. No. 5,804,161, PCT WO91/14460, and PCT WO 92/17215).

MRI contrast agents suitable for use as cargo compounds include, but are not limited to, one or more paramagnetic metal ions, further comprising an optional linking moiety, $L_n$, between the cupredoxin entry domain and the paramagnetic metal ions. The paramagnetic metal ions are present in the form of metal complexes or metal oxide particles. U.S. Pat. Nos. 5,412,148, and 5,760,191, describe examples of chelators for paramagnetic metal ions for use in MRI contrast agents. U.S. Pat. No. 5,801,228, U.S. Pat. No. 5,567,411, and U.S. Pat. No. 5,281,704, describe examples of polychelants useful for complexing more than one paramagnetic metal ion for use in MRI contrast agents. U.S. Pat. No. 5,520,904, describes particulate compositions comprised of paramagnetic metal ions for use as MRI contrast agents.

In another embodiment, a cargo compound is delivered to kill or retard cell cycle progression in a cell, such as a cancer cell. Such a cancer cell can be, for example, an osteosarcoma cell, lung carcinoma cell, colon carcinoma cell, lymphoma cell, leukemia cell, soft tissue sarcoma cell or breast, liver, bladder or prostate carcinoma cell. For example, the cargo compound can be a cell cycle control protein, such as p53; a cyclin-dependent kinase inhibitor, such as p16, p21 or p2'7; a suicide protein such as thymidine kinase or nitroreductase; a cytokine or other immunomodulatory protein such as interleukin 1, interleukin 2 or granulocyte-macrophage colony stimulating factor (GM-CSF); or a toxin, such as *Pseudomonas aeruginosa* exotoxin A. In other embodiments, a biologically active fragment of one of the above classes of compounds is delivered.

In yet another embodiment, the cargo compound is a nucleic acid coding for one of the above classes of compounds. In yet another embodiment, the cargo compound is a drug used to treat cancer. Such drugs include, for example, 5-fluorouracil; Interferon α; Methotrexate; Tamoxifen; and Vincristine. The above examples are provided for illustration only, many other such compounds are known to those skilled in the art.

Cargo compounds suitable for treating cancer include, but not limited to, alkylating agents such as nitrogen mustards, alkyl sulfonates, nitrosoureas, ethylenimines, and triazenes; antimetabolites such as folate antagonists, purine analogues, and pyrimidine analogues; antibiotics such as anthracyclines, bleomycins, mitomycin, dactinomycin, and plicamycin; enzymes such as L-asparaginase; farnesyl-protein transferase inhibitors; 5.alpha.-reductase inhibitors; inhibitors of 17β-hydroxysteroid dehydrogenase type 3; hormonal agents such as glucocorticoids, estrogens/antiestrogens, androgens/antiandrogens, progestins, and luteinizing hormone-releasing hormone antagonists, octreotide acetate; microtubule-disruptor agents, such as ecteinascidins or their analogs and derivatives; microtubule-stabilizing agents such as taxanes, for example, paclitaxel, docetaxel, and their analogs, and epothilones, such as epothilones A-F and their analogs; plant-derived products, such as vinca alkaloids, epipodophyllotoxins, taxanes; and topiosomerase inhibitors; prenyl-protein transferase inhibitors; and miscellaneous agents such as hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators and monoclonal antibodies.

Representative examples of these classes of anti-cancer and cytotoxic agents include but are not limited to mechlorethamine hydrochloride, cyclophosphamide, chlorambucil, melphalan, ifosfamide, busulfan, carmustin, lomustine, semustine, streptozocin, thiotepa, dacarbazine, methotrexate, thioguanine, mercaptopurine, fludarabine, pentastatin, cladribin, cytarabine, fluorouracil, doxorubicin hydrochloride, daunorubicin, idarubicin, bleomycin sulfate, mitomycin C, actinomycin D, safracins, saframycins, quinocarcins, discodermolides, vincristine, vinblastine, vinorelbine tartrate, etoposide, etoposide phosphate, teniposide, paclitaxel, tamoxifen, estramustine, estramustine phosphate sodium, flutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, altretamine, and topoteca and any analogs or derivatives thereof.

Preferred members of these classes include, but are not limited to, paclitaxel, cisplatin, carboplatin, doxorubicin, carminomycin, daunorubicin, aminopterin, methotrexate, methopterin, mitomycin C, ecteinascidin 743, or pofiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine and leurosine.

Examples of anticancer and other cytotoxic agents useful as cargo compounds include the following: epothilone derivatives as found in German Patent No. 4138042.8; WO 97/19086, WO 98/22461, WO 98/25929, WO 98/38192, WO 99/01124, WO 99/02224, WO 99/02514, WO 99/03848, WO 99/07692, WO 99/27890, WO 99/28324, WO 99/43653, WO 99/54330, WO 99/54318, WO 99/54319, WO 99/65913, WO 99/67252, WO 99/67253 and WO 00/00485; cyclin dependent kinase inhibitors as found in WO 99/24416 (see also U.S. Pat. No. 6,040,321); and prenyl-protein transferase inhibitors as found in WO 97/30992 and WO 98/54966; and agents such as those described generically and specifically in U.S. Pat. No. 6,011,029 (the compounds of which U.S. patent can be employed together with any NHR modulators (including, but not limited to, those of present invention) such as AR modulators, ER modulators, with LHRH modulators, or with surgical castration, especially in the treatment of cancer).

The above other therapeutic agents, when employed as cargo compounds with the compounds of the present invention, may be used, for example, in those amounts indicated in the Physicians' Desk Reference (PDR) or as otherwise determined by one of ordinary skill in the art.

In another embodiment, the cupredoxin peptide is a structural equivalent of a cupredoxin. Examples of studies that determine significant structural homology between cupredoxins and other proteins include Toth et al. (Developmental Cell 1:82-92 (2001)). Specifically, significant structural homology between a cupredoxin and the structural equivalent is determined by using the VAST algorithm. Gibrat et al., Curr Opin Struct Biol 6:377-385 (1996); Madej et al., Proteins 23:356-3690 (1995). In specific embodiments, the VAST p value from a structural comparison of a cupredoxin to the cupredoxin peptide is less than about $10^{-3}$, less than about $10^{-5}$, or less than about $10^{-7}$. In other embodiments, significant structural homology between a cupredoxin and the cupredoxin peptide is determined by using the DALI algorithm. Holm & Sander, J. Mol. Biol. 233:123-138 (1993). In specific embodiments, the DALI Z score for a pairwise structural comparison is at least about 3.5, at least about 7.0, or at least about 10.0.

It is contemplated that the cupredoxin peptides may be more than one of a variant, derivative and/or structural equivalent of a cupredoxin. For example, the cupredoxin peptides may be a truncation of azurin that has been PEGylated, thus making it both a variant and a derivative. In one embodiment, the cupredoxin peptides are synthesized with α,α-disubstituted non-natural amino acids containing olefin-bearing tethers, followed by an all-hydrocarbon "staple" by ruthenium catalyzed olefin metathesis. Scharmeister et al., J. Am. Chem. Soc. 122:5891-5892 (2000); Walensky et al., Science 305:1466-1470 (2004). Additionally, cupredoxin peptides that are structural equivalents of azurin may be fused to other peptides, thus making a peptide that is both a structural equivalent and a derivative. These examples are merely to illustrate and not to limit the invention. Cupredoxin peptides may or may not bind copper.

In some embodiments, the cupredoxin peptide has some of the functional characteristics of the *P. aeruginosa* azurin, and specifically p28. In a specific embodiment, the cupredoxin peptides may inhibit angiogenesis in mammalian cells, tissues or animals, and specifically but not limited to, HUVECs. The cupredoxin peptides may have the ability to inhibit the growth of mammalian cancer cells, and specifically but not limited to, melanoma, breast, pancreas, glioblastoma, astrocytoma, or lung cancer cells. The cupredoxin peptide may have the ability to inhibit the development of premalignant mammalian cells. The cupredoxin peptide may have the ability to enter mammalian cancer cells as compared to equivalent non-cancer cells, specifically, but not limited to, melanoma, breast, pancreas, glioblastoma, astrocytoma, or lung cancer cells Inhibition of angiogenesis or growth of cancer cells is any decrease, or lessening of the rate of increase, of that activity that is statistically significant as compared to control treatments. The entry into cells is any rate of entry into the cells that is statistically significant when compared to the rate of entry into equivalent normal cells.

In some embodiments, the cupredoxin peptide is derived from, but is not limited to, azurin, pseudoazurin, plastocyanin, rusticyanin, auracyanin, stellacyanin, cucumber basic protein or Laz. In particularly specific embodiments, the azurin is derived from *Pseudomonas aeruginosa, Alcaligenes faecalis, Achromobacter xylosoxidans* ssp. *denitrificans* I, *Bordetella bronchiseptica, Methylomonas* sp., *Neisseria meningitidis, Neisseria gonorrhea, Pseudomonas fluorescens, Pseudomonas chlororaphis, Xylella fastidiosa, Ulva pertussis* or *Vibrio parahaemolyticus*. In a very specific embodiment, the azurin is derived from *Pseudomonas aeruginosa*. In other specific embodiments, the cupredoxin peptide comprises an amino acid sequence that is SEQ ID NO: 1-25.

In some embodiments, the cupredoxin peptide has some of the pharmacologic activities of the *P. aeruginosa* azurin, and specifically p28. In a specific embodiment, the cupredoxin peptide may inhibit the development of tumors, decrease the growth of tumors or kill tumor cells in mammalian cells, tissues or animals. In some embodiments, the mammalian tumor is composed of, but is not limited to, melanoma, breast, pancreas, glioblastoma, astrocytoma, lung, colorectal, neck and head, bladder, prostate, skin and cervical cancer cells. Inhibition of the development of tumors is any decrease, or lessening of the rate of increase, of the development of tumors that is statistically significant as compared to control treatments.

Cells of the Invention

The invention provides cells which express proteins of choice when contacted by cancer cells. This aspect of the invention uses the azurin gene from *P. aeruginosa*, which has been disclosed herein to be inducible by contact with cancer cells. In one embodiment, the cell of the invention is from *P. aeruginosa*, and harbors in its genome a copy of the *P. aeruginosa* azurin gene in which the coding sequence for azurin has been replaced by the coding sequence for a target protein, and which expresses the target protein upon contact with cancer cells. In another embodiment, the cell may be a species other than *P. aeruginosa*, which harbors in its genome a copy of the *P. aeruginosa* azurin gene, and which expresses *P. aeruginosa* azurin when contacted with cancer cells. An example of this embodiment is provided in Example 3. In another embodiment, the cell may be a species other than *P. aeruginosa* which harbors in its genome a copy of the *P. aeruginosa* azurin gene in which the coding sequence for azurin has been replaced by the coding sequence of a target protein, and which expresses the target protein upon contact with cancer cells.

Target proteins of interest include therapeutic proteins, cytotoxic proteins and diagnostic proteins, and any other protein for which production near cancer cells would be advantageous. Examples of therapeutic proteins of interest include the cupredoxin peptides provided herein. Methods to make such cells are well known to those of ordinary skill in the art, and instructional manuals are available, including Sambrook et al., *Molecular Cloning: A Laboratory Manual* (Cold Spring Harbor Laboratory Press, Cold Spring Harbor, Mass. (2001)). Nonetheless, the following non-limiting cell preparation and translation treatment methods are provided.

Exemplary Host Cell Preparation Methodology.

Host cells to be transformed may be grown in any growth conducive medium. Examples of such media include but are not limited to Luria Broth, Luria Broth supplemented with 20 mM MgCl.sub.2, 0.001% thiamine, and 0.2% glucose; SOB medium containing 0.001% PPG (recipe given below); and 15/10 medium (recipe given below). Other suitable media will be readily recognized by one of skill in the art.

The incubation temperatures for growing the cells may vary from about 10° to about 42° C. In one embodiment, the temperature ranges from about 12° to about 37° C. In another embodiment, the temperature ranges from about 15° C. to about 32° C., and in another embodiment from about 20° to about 25° C. In one particular embodiment, the cells may be grown at about 23° C.

As one of ordinary skill in the art will understand, growth conditions and culture age can affect both the viability and the transformation efficiency of cells following cryopreservation. Cells grown in shake flask culture are generally more resistant to the stress of freeze-drying than are static broth cultures. Furthermore, the age of a culture also affects the ability of the culture to survive freeze-drying. Generally, cells harvested in late log or early stationary growth exhibit the greatest resistance to freeze-drying if such freeze-drying is contemplated.

Thus, when freeze-drying is contemplated, the cells are preferably grown in shake flasks, although other means of growth may be used including fermentators. Shake flasks used can be of any size and any type. In one embodiment, baffled 2.8 liter shake flasks may be used for this processing. Incubation times will vary according to the conditions used (temperature, medium, aeration, etc.) and the cell type. Aeration in flasks will also vary according to the rotation per minute (rpm) used, with higher rpms resulting in higher aeration. In certain embodiments, flasks are typically shaken at 100-500 rpms, at 200-400 rpms, and at 200-300 rpms, although one of ordinary skill in the art may determine other preferred ranges. Cells are typically grown for a time and under conditions sufficient to reach an optical density (OD) at 550 nm between about 0.1 to about 2.0. In one embodiment, the OD ranges from about 0.1 to about 1.0. In another embodiment, the OD ranges from about 0.3 to about 0.8. In another embodiment, the OD ranges from about from 0.5 to about 0.8. In another embodiment, the OD ranges from about 0.5 to about 0.7. In another embodiment, the OD ranges from about 0.6 to about 0.8. And in yet another embodiment, the OD ranges from about 0.66 to about 0.75.

After the cells have reached the desired OD, the cells may be collected for further processing. If the desired OD is not reached or is exceeded, the cells can again be reinoculated and the growth process repeated until a culture of sufficient optical density is obtained.

After the cells are collected (by, without limitation, centrifugation, filtration, etc.), they may optionally be chilled (e.g., 0° to 4° C. for 5 minutes to 2 hours). Collection of the cells may be accomplished by centrifuging the cells to obtain a cell pellet. Collection may also be accomplished by concentrating the cells and then centrifuging the concentrated cultures to obtain a cell pellet. Methods of concentrating the cells include, but are not limited to, dewatering the culture, filtering, or subjecting the culture to size exclusion chromatography, e.g. using by Centricon™ columns (Amicon Corp., Lexington, Mass.).

After the cells are collected, the cells may be resuspended in a competence buffer. A competence buffer is any solution that enables cells to take up and establish exogenous DNA. Non-limiting examples of competence buffers include 50 mM $CaCl_2$, 10 mM Tris/HCl (Maniatis, T. et al., *Molecular Cloning: A Laboratory Manual,* 2nd ed., Cold Spring Harbor, N.Y. (1989)); 0.1 M MOPS (pH 6.5), 50 mM $CaCl_2$, 10 mM $RbCl_2$, 23% V/V DMSO; CCMB80 buffer (10 mM potassium acetate pH 7.0, 80 mM $CaCl_2.H_2O$, 20 mM $MnCl_2 4H_2O$, 10 mM $MgCl_2 6H_2O$, 10% glycerol adjusted to pH 6.4 with 0.1 N HCl); TFB buffer (Liu et al., Biotechniques 8(1):23-25 (1990)); and n1776 buffer (Maniatis, T. et al., Molecular Cloning: A Laboratory Manual (2nd ed., Cold Spring Harbor, N.Y. (1989)). Other suitable buffers are disclosed in Tang et al., Nucl. Acids Res. 22(14):2857-2858 (1994); Chung et al., Proc. Natl. Acad Sci. U.S.A. 86:2172-2175 (1989); M. Dagert and S. D. Ehrlich, Gene 6:23-28 (1974); Kushner, S. R., In: Genetic Engineering (H. W. Boyer and S. Nicosia, eds.) pp. 17-23, Elsevier/North Holland, Amsterdam (1978); Mandel and Higa, J. Mol. Biol. 53:159-162 (1970); U.S. Pat. No. 4,981,797 by Jessee; and Hanahan, D., J. Mol. Biol. 166:557-580 (1983) which are incorporated by reference herein.

The cells suspended in the competence buffer are incubated for a sufficient time and at a temperature sufficient to make the cells competent to DNA uptake. In one embodiment, the cells are incubated at low temperature (0 to 4° C.) for about 0 to about 3 hours. In another embodiment, the cells are incubated at low temperature (0 to 4° C.) for about 5 minutes to about 1 hour. In another embodiment, the cells are incubated at low temperature (0 to 4° C.) for about 5 minutes to about 30 minutes.

After the cells have been made competent, a cryoprotectant may be added directly to the cell suspension. In one embodiment, the cells can be collected and then resuspended in a cryoprotectant. The concentration of the cryoprotectant can vary depending on the cell type, buffers used, the type of cryoprotectant and other factors. Optimal conditions can be determined by one of ordinary skill in the art without undue experimentation. When used, cryoprotectants provide protection of the cells during the freezing process by depressing the freezing point, minimizing the effect of solution changes external to the cell, penetrating the cell to protect against solute concentration effects, and/or shifting the optimum cooling rate to lower values (F. P. Simione, Journal of Parenteral Science & Technology, 46(6):226-232 (1992)). Of course, the cryoprotectant must not be toxic to the cells.

Any cryoprotectant and combination thereof may be and as will be apparent, the type and amount used may vary depending on the cell type and conditions used. Cryoprotectants that can be used in the present invention include, but are not limited to, carbohydrates and carbohydrate derivatives such as trehalose, sucrose, lactose, maltose, mannitol, galactose, ribose, fructose, xylose, mannose, dextrose, glucose, and sorbitol, and polymers such as polyethyleneamine, polyvinylpyrrolidone (PVP), ficoll, etc. Other cryoprotectants which can be used in accordance with the invention, such as acacia gum, albumin, gelatin, and sugar alcohols, will be readily recognized by one skilled in the art.

After the cells have been mixed with the cryoprotectant, the cell suspension may be aliquoted into containers to be used for lyophilization and storage, such as chilled cryovials, e.g., NUNC tubes (Gibco BRL, Gaithersburg, Md., Cat. No. 366656), or glass vials (Wheaton, Millville, N.J.). Prior to lyophilization, in one embodiment the cells may be frozen at about −20° C. to about −180° C. In another embodiment they may be frozen at about −80° C. to about −180° C. In a particular embodiment they may be frozen at about −80° C.

Methods of freezing a sample to a temperature from about −80° to about −180° C. are well known in the art. These include overnight storage (about 16 hours) of the vials which contain the cells in a −80° C. freezer, or immersion of the vials which contain the cells in dry ice, or in a low temperature bath, such as dry ice ethanol, or in a bath containing liquid nitrogen. Other such systems are disclosed in The Chemist's Companion: A Handbook of Practical Data, Techniques, and References, Gordon, A. J., et al., eds., John Wiley and Sons, NY (1972) which is incorporated by reference herein.

If desired, the cells can then be lyophilized by techniques which are well known in the art. Lyophilization is a process by which ice and/or moisture is removed from frozen cells by sublimation under vacuum at low, subzero temperatures (e.g., −40° to −50° C.). Any residual moisture associated with the "dried" preparation is then removed by gradually raising the temperature, resulting in evaporation. Thus, lyophilization comprises subjecting frozen cells to a vacuum under conditions sufficient to substantially remove moisture and/or ice from said cells (also referred to herein as substantially dried cells). The substantially dried cells may then be stored at various temperatures (room temperature to about −180° C., and in certain embodiments, from about 4° C. to about −80° C., from about −20° C. to about −80° C., and in one particular embodiment at about −20° C.).

One non-limiting example of a cell lyophilization process comprises the steps of (a) loading a container containing frozen cells into a lyophilizer, the lyophilizer having a temperature of about −40° to about −50° C.; (b) subjecting the cells to a vacuum; and (c) substantially drying the cells. In one embodiment the vacuum is less than about 100 μm, and the cells are dried by: (i) holding the temperature of the chamber at about −45° C. for about 2 hours; and (ii) increasing the temperature of the chamber from about −45° C. to about 10° C. at the rate of about 0.1° to about 1.0° C./hr (in one embodiment, about 0.5° to about 0.8° C./hr, and in a particular embodiment about 0.6° to about 0.8° C./hr). The cell container may then be sealed and stored for extended time at various temperatures.

The viable host cell count of competent cells produced by the described method should remain at greater than about $1\times10^7$ to about $1\times10^9$ cells/ml when stored at −20° C. for any time period from about 0 days to about 450 days. The cells likely retain a transformation efficiency of at least about $1\times10^5$ and preferably at least about $1\times10^9$ transformants per microgram of DNA (T/μg). Suitable storage temperatures vary from about room temperature to about −180° C. In one embodiment the storage temperature ranges from about 4° C. to about −80° C. In another embodiment the storage temperature ranges from about −20° C. to about −80° C. In another particular embodiment the storage temperature ranges from about −20° C. The storage period or time may range from about 0 days to about 45 days, from about 0 days to about 90 days, from about 0 days to about 150 days, from about 240 days to about 365 days, or from about 365 days to about 450 days, although longer storage times may be used at temperatures of about −20° C. and below. Competent host cells produced by this method may be stored at −20° C. for at least one year while retaining substantially their transformation efficiency.

Exemplary Host Cell Transformation Methodology. In order to transform host cells, and as will be understood by those of ordinary skill in the art, generally the cells can be mixed with a DNA molecule of interest and incubated under conditions sufficient to transform the cells with said DNA molecule. Any DNA molecules (e.g. vectors, plasmids, phagemids, expression vectors, etc.) may be used. Preferably, the cells are mixed with the DNA molecule in the presence of a competence buffer. The competence buffer may be added to competent host cells prior to adding the DNA molecule or the DNA molecule and competence buffer may be added simultaneously to the competent host cells. Although mixing the competent host cells with the DNA molecule and a competence buffer is preferred, any solution may be used to rehydrate and mix the cells with the DNA molecule of interest. Such solutions include water, saline, or any suitable buffer.

The following more detailed non-limiting example is also provided. About 25-200 µl cells can be thawed and kept on ice. The cells should not be placed in glass tubes as glass will adsorb the DNA of interest. DNA can be gently pipetted into the cell mixture, keeping the volume of DNA to less than about 5% of the cell volume. The cells can be incubated with the DNA of interest for about 5 to about 30 minutes. Next, the cells can be incubated for about 30 seconds at about 42° C. and then incubated for about 2 minutes on ice. At this stage, about 4 volumes of SOC Medium can be added but this addition should not be critical to the success of the transformation. The cells can then be incubated for about 30 minutes to about 1 hour on a shaker at 37° C. Following this incubation, about 100-300 µl of the cell/DNA mixture can be spread onto a plate made with an appropriate antibiotic, if desired.

Once the cells have been transformed with the DNA molecule of interest, the transformed cells may be grown in a growth conducive medium. Typically, such a growth conducive medium will also contain an antibiotic to assist in selection of the transformed cells. That is, the DNA molecule to be transformed may contain a selective marker (e.g. an antibiotic resistance gene), allowing selection of the transformed cells when the corresponding antibiotic is used in the medium. These aspects of the process are not, however, required.

When transformed host cells (and condensed DNA) are used as a treatment according to the present invention, particularly useful administration methods may include, without limitation, local delivery through a catheter and drug pump system, delivery by direct local injection or through the use of polymers. In one embodiment, a "controlled administration system" including a direct and local administration system can be used. A controlled administration system can be a depot or a pump system, such as, without limitation, an osmotic pump or an infusion pump. An infusion pump can be implantable and can be, without limitation, a programmable pump, a fixed rate pump, and the like. A catheter can be operably connected to the pump and configured to deliver cells of the present invention to a target tissue region of a subject. Other delivery methods described throughout the remainder of the specification may also be appropriate.

Methods of Use

The invention provides methods to treat patients, specifically patients suffering from a condition, specifically cancer, and to prevent cancer in patients, comprising co-administering to said patients CpG rich DNA from *P. aeruginosa* and at least one cupredoxin peptide. Such treatment can be carried out by administering at least one of the isolated CpG rich polynucleotides of the invention. Cancers that may be prevented or treated by treatment with the compositions of the invention include, but are not limited to, melanoma, breast, pancreas, glioblastoma, astrocytoma, lung, colorectal, neck and head, bladder, prostate, skin, and cervical cancer. In other embodiments, the patients are suffering from AIDS, malaria, inappropriate angiogenesis, or are at a higher at risk to develop cancer than the general population. In some embodiments, the patient may be human. In other embodiments, the patient is not human.

The compositions comprising at least one CpG rich DNA from *P. aeruginosa* and at least one cupredoxin peptide can be administered to the patient by many routes and in many regimens that will be well known to those in the art. In specific embodiments, the CpG rich DNA from *P. aeruginosa* and cupredoxin peptide are administered intravenously, intramuscularly, subcutaneously, topically, orally, or by inhalation. The compositions may be administered to the patient by any means that delivers the polynucleotides and polypeptides to the patient. In some embodiments, the patient is suffering from cancer and the compositions are administered in a manner that delivers the polynucleotides and polypeptides to the site of the tumor. In specific embodiments, the CpG rich DNA from *P. aeruginosa* and cupredoxin peptide are administered intravenously.

In some embodiments, the methods of the invention comprise administering to a patient at least one composition comprising one unit dose of a cupredoxin peptide and one unit dose of a CpG rich DNA from *P. aeruginosa*.

In other embodiments, the methods may comprise co-administering to a patient one unit dose of at least one composition comprising a cupredoxin peptide and one unit dose of at least one composition comprising a CpG rich DNA from *P. aeruginosa* in either order, administered at about the same time, or within about a given time following the administration of the other, for example, about one minute to about 60 minutes following the administration of the other drug, or about 1 hour to about 12 hours following the administration of the other drug.

In other embodiments, the methods may comprise co-administering to a patient one unit dose of at least one composition comprising a cupredoxin peptide, one unit dose of at least one composition comprising a CpG rich DNA from *P. aeruginosa*, and one unit dose of a composition comprising another prophylactic or therapeutic drug, in either order, administered at about the same time, or within about a given time following the administration of the others, for example, about one minute to about 60 minutes following the administration of the other drug, or about 1 hour to about 12 hours following the administration of the other drug. The additional therapeutic drug may be one or more of many that are commonly used to treat the condition suffered by the patient or the side effects of the treatment. Such therapeutic drugs include, but are not limited to, those used to treat cancer, AIDS, malaria, inappropriate angiogenesis, inflammatory bowel disease, viral diseases, cardiovascular disease, peripheral vascular diseases, central nervous system disorders, degeneration of the central nervous system and Alzheimer's disease and to prevent cancer. Examples of such therapeutic drugs are provided in U.S. Pat. No. 7,084,105, U.S. Patent Application Publication No. 20060040269, published Feb. 23, 2006, now U.S. Pat. No. 7,491,394; U.S. Patent Application Publication No. 20060149037, published Jul. 6, 2006, now U.S. Pat. No. 7,691,383; U.S. Patent Application Publication No. 20080213185, published Sep. 4, 2008, now U.S. Pat. No. 7,807,183; U.S. Patent Application Publication No. 20080089878, published Apr. 17, 2008, now U.S. Pat. No. 7,381,701; U.S. Patent Application Publication No. 20080103087, published May 1, 2008, now U.S. Pat. No. 7,556,810; U.S. Patent Application Publication No. 20060251669, now U.S. Pat. No. 7,338,766; U.S. Patent Application Publication No. 20060251639, published Nov. 9, 2006, now U.S. Pat. No. 7,301,010; U.S. Patent Application Publication No. 20100267608, published Oct. 21, 2010; and U.S. Patent Application Publication No. 20080139471, published Jun. 12, 2008, now U.S. Pat. No. 7,618,939, each of which in incorporated herein by reference. Further therapeutic drugs of interest may be found in the *Thomson Physician's Desk Reference* (Thomson Healthcare, Stamford Conn., 2006), and other references that are well known to those of ordinary skill in the art.

Drugs for treating cancer include but are not limited to mechlorethamine hydrochloride, cyclophosphamide, chlorambucil, melphalan, ifosfamide, busulfan, carmustin, lomustine, semustine, streptozocin, thiotepa, dacarbazine, methotrexate, thioguanine, mercaptopurine, fludarabine, pentastatin, cladribin, cytarabine, fluorouracil, doxorubicin hydrochloride, daunorubicin, idarubicin, bleomycin sulfate, mitomycin C, actinomycin D, safracins, saframycins, quinocarcins, discodermolides, vincristine, vinblastine, vinorelbine tartrate, etoposide, etoposide phosphate, teniposide, paclitaxel, tamoxifen, estramustine, estramustine phosphate sodium, flutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, altretamine, and topoteca and any analogs or derivatives thereof.

Preferred members of these classes include, but are not limited to, paclitaxel, cisplatin, carboplatin, doxorubicin, carminomycin, daunorubicin, aminopterin, methotrexate, methopterin, mitomycin C, ecteinascidin 743, or pofiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine and leurosine.

Drugs for treating cancer include the following: epothilone derivatives as found in German Patent No. 4138042.8; WO 97/19086, WO 98/22461, WO 98/25929, WO 98/38192, WO 99/01124, WO 99/02224, WO 99/02514, WO 99/03848, WO 99/07692, WO 99/27890, WO 99/28324, WO 99/43653, WO 99/54330, WO 99/54318, WO 99/54319, WO 99/65913, WO 99/67252, WO 99/67253 and WO 00/00485; cyclin dependent kinase inhibitors as found in WO 99/24416 (see also U.S. Pat. No. 6,040,321); and prenyl-protein transferase inhibitors as found in WO 97/30992 and WO 98/54966; and agents such as those described generically and specifically in U.S. Pat. No. 6,011,029 (the compounds of which U.S. patent can be employed together with any NHR modulators (including, but not limited to, those of present invention) such as AR modulators, ER modulators, with LHRH modulators, or with surgical castration, especially in the treatment of cancer).

Drugs for treating HIV infection include, but are not limited to, reverse transcriptase inhibitors: AZT (zidovudine), ddC (zalcitabine, dideoxyinosine), d4T (stavudine), and 3TC (lamivudine), nonnucleoside reverse transcriptase inhibitors (NNRTIS): delavirdine and nevirapine, protease inhibitors: ritonavir, a lopinavir and ritonavir combination, saquinavir, indinavir sulphate, amprenavir, and nelfinavir. Presently, a combination of several drugs called highly active antiretroviral therapy (HAART) is used to treat people with HIV.

Drugs for treating malaria include, but are not limited to, proguanil, chlorproguanil, trimethoprim, chloroquine, mefloquine, lumefantrine, atovaquone, pyrimethamine-sulfadoxine, pyrimethamine-dapsone, halofantrine, quinine, quinidine, amodiaquine, amopyroquine, sulphonamides, artemisinin, arteflene, artemether, artesunate, primaquine, pyronaridine, proguanil, chloroquine, mefloquine, pyrimethamine-sulfadoxine, pyrimethamine-dapsone, halofantrine, quinine, proguanil, chloroquine, mefloquine, 1,16-hexadecamethylenebis(N-methylpyrrolidinium)dibromide, and combinations thereof.

Drugs for treating with inflammatory bowel disease, include, but are not limited to, aminosalicylates, such as, sulfasalazine, olsalazine, mesalamine, and balsalazide; corticosteroids, such as, prednisone, methylprednisolone, hydrocortisone, Budesonide; immunomodulators, such as, azathioprine, 6-mercaptopurine (6-MP) and cyclosporine A; antibiotics, such as, metronidazole and ciprofloxacin; biologic therapies, such as, infliximab; and miscellaneous therapies, such as, tacrolimus (FK506) and mycophenolate mofetil.

Drugs for treating HIV infection include, but are not limited to, reverse transcriptase inhibitors: AZT (zidovudine), ddC (zalcitabine, dideoxyinosine), d4T (stavudine), and 3TC (lamivudine), nonnucleoside reverse transcriptase inhibitors (NNRTIS): delavirdine and nevirapine, protease inhibitors: ritonavir, a lopinavir and ritonavir combination, saquinavir, indinavir sulphate, amprenavir, and nelfinavir.

Drugs for treating viral diseases include, but are not limited to, acyclovir, varicella zoster immune globulin, peginterferon, ribavirin, acyclovir, valacyclovir, famciclovir, amantadine, rimantadine, zanamivir, oseltamivir, and alpha interferon.

Drugs for treating cardiovascular disorders include, but are not limited to, anticoagulants, antiplatelet agents, thrombolytic agents, adrenergic blockers, adrenergic stimulants, alpha/beta adrenergic blockers, angiotensin converting enzyme (ACE) inhibitors, angiotensin converting enzyme (ACE) inhibitors with calcium channel blockers, angiotensin converting enzyme (ACE) inhibitors with diuretics, angiotensin II receptor antagonists, calcium channel blockers, diuretics (including carbonic anhydrase inhibitors, loop diuretics, potassium-sparing diuretics, thiazides and related diuretics, vasodilators, vasopressors, etc.

Drugs for treating peripheral vascular disease include, but are not limited to, pentoxifylline, an oral methylxanthine derivative, and cilostazol, a phosphodiesterase III inhibitor; antiplatelet/antithrombotic therapy such as aspirin; anticoagulants such as heparin and warfarin; cholesterol lowering drugs, such as, niacin, statins, fibrates, gemfibrozil; fenofibrate; bile acid sequestrants, micronized colestipol hydrochloride; colesevelam hydrochloride; calcium channel blockers; vitamins and dietary supplements, such as, folate, B-6, B-12, L-arginine and omega-3 fatty acids; and HMG-COA Reductase inhibitors, such as, Niacin/Lovastatin; lovastatin; fluvastatin sodium; atorvastatin; lovastatin; Pravastatin sodium; Buffered Aspirin and Pravastatin Sodium; Simvastatin; Merck); nicotinic acid agents, such as, Niacin/Lovastatin (also listed as a HMG-COA Reductase inhibitor); niacin; and miscellaneous agents, such as, ezetimibe.

Drugs for treating central nervous system disorders include, but are not limited to, psychotherapeutic agents, such as, various benzodiazepine preparations and combinations, antianxiety agents, antidepressants (including monoamine oxidase inhibitors (MAOI), selective serotonin reuptake inhibitors (SSRIs), tricyclic antidepressants), antimanic agents, antipanic agents, antipsychotic agents, psychostimulants, and obsessive-compulsive disorder management agents; migraine preparations, such as beta adrenergic blocking agents, isometheptene and serotonin receptor agonists, as well as miscellaneous migraine preparations including Divalproex sodium and acetaminophen; sedatives and hypnotics; anticonvulsants; and pimozide. Drugs for treating Parkinson's disease include, but are not limited to, anticholinergic agents, catechol-o-methyltransferase inhibitors, dopamine agents and monoamine oxidase (MAO) inhibitors.

Drugs for treating Central Nervous System (CNS) degeneration disorders include the following: Drugs for treating Multiple Sclerosis include, but are not limited to, interferon beta-1a; BETASERON for SC injection (modified form of Interferon beta-1b; Berlex); Glatiramer Acetate; Methylprednisolone acetate; Mitoxantrone supplied as mitoxantrone hydrochloride; prednisolone sodium phosphate oral solution. Drugs for treating Huntington's Disease include, but are not limited to, tranquilizers such as clonazepam; antipsychotic drugs such as haloperidol and clozapine; fluoxetine, sertraline, nortriptyline, and lithium.

Drugs for treating Alzheimer's disease include, but are not limited to, Donepezil Hydrochloride; rivastigmine (as the hydrogen tartrate salt); rivastigmine tartrate; galantamine hydrobromide; or galantamine hydrobromide.

Chemopreventive drugs of interest include, but are not limited to, tamoxifen, aromatase inhibitors such as letrozole and anastrozole, retinoids such as N-[4-hydroxyphenyl] retinamide (4-HPR, fenretinide), nonsteriodal antiinflammatory agents (NSAIDs) such as aspirin and sulindac, celecoxib (COX-2 inhibitor), defluoromethylornithing (DFMO), ursodeoxycholic acid, 3-hydroxy-3-methylglutaryl coenzyme A reductase inhibitors, EKI-785 (EGFR inhibitor), bevacizumab (antibody to VEGF-receptor), cetuximab (antibody to EGFR), retinol such as vitamin A, beta-carotene, 13-cis retinoic acid, isotretinoin and retinyl palmitate, α-tocopherol, interferon, oncolytic adenovirus dl1520 (ONYX-015), gefitinib, etretinate, finasteride, indole-3-carbinol, resveratrol, chlorogenic acid, raloxifene, and oltipraz.

The methods of the invention further comprise methods of administering the cells of the invention. Such methods include methods for treating patients, specifically suffering from conditions, specifically cancer, and methods for diagnosing cancer in patients. In some embodiments, patients suffering from cancer may be treated by administering either a cell expressing azurin when in contact with cancer cells, or expressing a therapeutic or cytotoxic target protein when in contact with cancer cells. In other embodiments, the patients are suffering from cancer, such as, but not limited to, melanoma, breast, pancreas, glioblastoma, astrocytoma, lung, colorectal, neck and head, bladder, prostate, skin, and cervical cancer. In other embodiments, the method diagnoses cancer in a patient by administering a cell expressing a diagnostic protein when contacted by cancer cells, and then detecting the diagnostic protein, either in the blood stream or at its site of expression.

The cells of the invention may be administered to patients by any means suitable, including but not limited to, intravenous injection, intramuscular injection, subcutaneous injection, inhalation, topical administration, suppository, vitreous injection and oral. In a specific embodiment, the cells are administered intravenously.

Pharmaceutical Compositions Comprising CpG Rich DNA or Cells

Pharmaceutical compositions comprising CpG rich DNA from *P. aeruginosa* or the cells of the invention may be manufactured in any suitable conventional manner, e.g., by conventional mixing, dissolving, granulating, dragee-making, emulsifying, encapsulating, entrapping, or lyophilizing processes. The substantially pure or pharmaceutical grade CpG rich DNA from *P. aeruginosa* or the cells of the invention can be readily combined with a pharmaceutically acceptable carrier well-known in the art. Such carriers enable the preparation to be formulated as a tablet, pill, dragee, capsule, liquid, gel, syrup, slurry, suspension, and the like. Suitable carriers or excipients can also include, for example, fillers and cellulose preparations. Other excipients can include, for example, flavoring agents, coloring agents, detackifiers, thickeners, and other acceptable additives, adjuvants, or binders. In some embodiments, the pharmaceutical preparation is substantially free of preservatives. In other embodiments, the pharmaceutical preparation may contain at least one preservative. General methodology on pharmaceutical dosage forms is found in Ansel et al., *Pharmaceutical Dosage Forms and Drug Delivery Systems* (Lippencott Williams & Wilkins, Baltimore Md. (1999)).

The composition comprising CpG rich DNA from *P. aeruginosa* or the cells of the invention may be administered in a variety of ways, including by injection (e.g., intradermal, subcutaneous, intramuscular, intraperitoneal and the like), by inhalation, by topical administration, by suppository, by using a transdermal patch or by mouth. General information on drug delivery systems can be found in Ansel et al., id. In some embodiments, the composition comprising CpG rich DNA from *P. aeruginosa* or the cells of the invention can be formulated and used directly as injectibles, for subcutaneous and intravenous injection, among others. The injectable formulation, in particular, can advantageously be used to treat patients that are appropriate for chemopreventive therapy. The composition comprising a CpG rich DNA from *P. aeruginosa* or the cells of the invention can also be taken orally, optionally after mixing with protective agents such as polypropylene glycols or similar coating agents.

When administration is by injection, the CpG rich DNA from *P. aeruginosa* or the cells of the invention may be formulated in aqueous solutions, specifically in physiologically compatible buffers such as Hanks solution, Ringer's solution, or physiological saline buffer. The solution may contain formulatory agents such as suspending, stabilizing and/or dispersing agents. Alternatively, the CpG rich DNA from *P. aeruginosa* may be in powder form for constitution with a suitable vehicle, e.g., sterile pyrogen-free water, before use. In some embodiments, the pharmaceutical composition does not comprise an adjuvant or any other substance added to enhance the immune response stimulated by the polynucleotide. In some embodiments, the pharmaceutical composition comprises a substance that inhibits an immune response to the polynucleotide.

When administration is by intravenous fluids, the intravenous fluids for use administering the CpG rich DNA from *P. aeruginosa* or the cells of the invention may be composed of crystalloids or colloids. Crystalloids as used herein are aqueous solutions of mineral salts or other water-soluble molecules. Colloids as used herein contain larger insoluble molecules, such as gelatin. Intravenous fluids may be sterile.

Crystalloid fluids that may be used for intravenous administration include but are not limited to, normal saline (a solution of sodium chloride at 0.9% concentration), Ringer's lactate or Ringer's solution, and a solution of 5% dextrose in water sometimes called D5W, as described in Table 1.

TABLE 1

Composition of Common Crystalloid Solutions

| Solution | Other Name | [Na+] | [Cl−] | [Glucose] |
|---|---|---|---|---|
| D5W | 5% Dextrose | 0 | 0 | 252 |
| ⅔ & ⅓ | 3.3% Dextrose/ 0.3% saline | 51 | 51 | 168 |
| Half-normal saline | 0.45% NaCl | 77 | 77 | 0 |
| Normal saline | 0.9% NaCl | 154 | 154 | 0 |
| Ringer's lactate* | Ringer's solution | 130 | 109 | 0 |

*Ringer's lactate also has 28 mmol/L lactate, 4 mmol/L K+ and 3 mmol/L $Ca^{2+}$.

When administration is by inhalation, the CpG rich DNA from *P. aeruginosa* or the cells of the invention may be delivered in the form of an aerosol spray from pressurized packs or a nebulizer with the use of a suitable propellant, e.g., dichlorodifluoromethane, trichlorofluoromethane, carbon dioxide or other suitable gas. In the case of a pressurized aerosol, the dosage unit may be determined by providing a valve to deliver a metered amount. Capsules and cartridges of, e.g., gelatin, for use in an inhaler or insufflator may be formulated containing a powder mix of the polynucleotides and a suitable powder base such as lactose or starch.

When administration is by topical administration, the CpG rich DNA from *P. aeruginosa* or the cells of the invention may be formulated as solutions, gels, ointments, creams, jellies, suspensions, and the like, as are well known in the art. In some embodiments, administration is by means of a transdermal patch. When administration is by suppository (e.g., rectal or vaginal), CpG rich DNA from *P. aeruginosa* or the cells of the invention compositions may also be formulated in compositions containing conventional suppository bases.

When administration is oral, the CpG rich DNA from *P. aeruginosa* or the cells of the invention can be readily formulated by combining the CpG rich DNA from *P. aeruginosa* or the cells of the invention with pharmaceutically acceptable carriers well known in the art. A solid carrier, such as mannitol, lactose, magnesium stearate, and the like may be employed; such carriers enable the CpG rich DNA from *P. aeruginosa* or the cells of the invention to be formulated as tablets, pills, dragees, capsules, liquids, gels, syrups, slurries, suspensions and the like, for oral ingestion by a subject to be treated. For oral solid formulations such as, for example, powders, capsules and tablets, suitable excipients include fillers such as sugars, cellulose preparation, granulating agents, and binding agents.

Other convenient carriers, as well-known in the art, also include multivalent carriers, such as bacterial capsular polysaccharide, a dextran or a genetically engineered vector. In addition, sustained-release formulations that include a CpG rich DNA from *P. aeruginosa* allow for the release of the CpG rich DNA over extended periods of time, such that without the sustained release formulation, the CpG rich DNA from *P. aeruginosa* would be cleared from a subject's system, and/or degraded by, for example, proteases and simple hydrolysis before eliciting or enhancing a therapeutic effect.

In various embodiments, the pharmaceutical composition includes carriers and excipients (including but not limited to buffers, carbohydrates, mannitol, proteins, polypeptides or amino acids such as glycine, antioxidants, bacteriostats, chelating agents, suspending agents, thickening agents and/or preservatives), water, oils, saline solutions, aqueous dextrose and glycerol solutions, other pharmaceutically acceptable auxiliary substances as required to approximate physiological conditions, such as buffering agents, tonicity adjusting agents, wetting agents and the like. It will be recognized that, while any suitable carrier known to those of ordinary skill in the art may be employed to administer the compositions of this invention, the type of carrier will vary depending on the mode of administration. Compounds may also be encapsulated within liposomes using well-known technology. Biodegradable microspheres may also be employed as carriers for the pharmaceutical compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252.

The pharmaceutical compositions comprising CpG rich DNA may be sterilized by conventional, well-known sterilization techniques, or may be sterile filtered. The resulting aqueous solutions may be packaged for use as is, or lyophilized, the lyophilized preparation being combined with a sterile solution prior to administration.

Administration of CpG Rich DNA or Cells

The CpG rich DNA from *P. aeruginosa* or cells of the invention can be administered formulated as pharmaceutical compositions and administered by any suitable route, for example, by oral, buccal, inhalation, sublingual, rectal, vaginal, transurethral, nasal, topical, percutaneous, i.e., transdermal or parenteral (including intravenous, intramuscular, subcutaneous and intracoronary) or vitreous administration. The pharmaceutical formulations thereof can be administered in any amount effective to achieve its intended purpose. More specifically, the composition is administered in a prophylactically or therapeutically effective amount. In specific embodiments, the prophylactically or therapeutically effective amount is generally from about 0.01-20 mg/day/kg of body weight.

The compounds comprising CpG rich DNA from *P. aeruginosa* or cells of the invention are useful for the treatment of conditions, and specifically cancer, and preventing cancer, alone or in combination with other active agents. The appropriate dosage will, of course, vary depending upon, for example, the compound of CpG rich DNA from *P. aeruginosa* or the cells of the invention employed, the host, the mode of administration and the nature and severity of the condition. However, in general, satisfactory results in humans are indicated to be obtained at daily dosages from about 0.01-20 mg/kg of body weight. An indicated daily dosage in humans is in the range from about 0.7 mg to about 1400 mg of a compound of CpG rich DNA from *P. aeruginosa* or the cells of the invention conveniently administered, for example, in daily doses, weekly doses, monthly doses, and/or continuous dosing. Daily doses can be in discrete dosages from 1 to 12 times per day. Alternatively, doses can be administered every other day, every third day, every fourth day, every fifth day, every sixth day, every week, and similarly in day increments up to 31 days or over. Alternatively, dosing can be continuous using patches, i.v. administration and the like.

The exact formulation, route of administration, and dosage is determined by the attending physician in view of the patient's condition. Dosage amount and interval can be adjusted individually to provide plasma levels of the CpG rich DNA from *P. aeruginosa* and cupredoxin peptide which are sufficient to maintain prophylactic or therapeutic effect. Generally, the desired CpG rich DNA from *P. aeruginosa* is administered in an admixture with a pharmaceutical carrier selected with regard to the intended route of administration and standard pharmaceutical practice. In the case of the cells, of the invention, dosage and interval can be adjusted individually to provide levels of the target protein or azurin at the site of the cancer cells which are sufficient to maintain a prophylactic or therapeutic effect or diagnostic presence.

Kits Comprising CpG Rich DNA or Cells

In one aspect, the invention provides regimens or kits comprising one or more of the following in a package or container: (1) a pharmaceutical composition comprising CpG rich DNA from *P. aeruginosa*; (2) a pharmaceutical composition comprising at least one cupredoxin peptide; (3) an additional prophylactic or therapeutic drug; and (4) apparatus to administer the biologically active composition to the patient, such as a syringe, nebulizer etc.

In another aspect, the invention provides regimens or kits comprising one or more of the following in a package or container: (1) a cell of the invention; and (2) an apparatus to administer the cells to the patient.

When a kit is supplied, the different components of the composition may be packaged in separate containers, if appropriate, and admixed immediately before use. Such packaging of the components separately may permit long-term storage without losing the active components' functions.

The reagents included in the kits can be supplied in containers of any sort such that the life of the different components are preserved and are not adsorbed or altered by the materials of the container. For example, sealed glass ampules may contain lyophilized CpG rich DNA, or buffers that have been packaged under a neutral, non-reacting gas, such as nitrogen. Ampules may consist of any suitable material, such as glass, organic polymers, such as polycarbonate, polystyrene, etc., ceramic, metal or any other material typically employed to hold similar reagents. Other examples of suitable containers include simple bottles that may be fabricated from similar substances as ampules, and envelopes, that may comprise foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to be mixed. Removable membranes may be glass, plastic, rubber, etc.

Kits may also be supplied with instructional materials. Instructions may be printed on paper or other substrate, and/or may be supplied as an electronic-readable medium, such as a floppy disc, CD-ROM, DVD-ROM, Zip disc, videotape, audiotape, flash memory device etc. Detailed instructions may not be physically associated with the kit; instead, a user may be directed to an internet web site specified by the manufacturer or distributor of the kit, or supplied as electronic mail.

A more complete understanding of the present invention can be obtained by reference to the following specific Examples. The Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations. Modifications and variations of the invention as hereinbefore set forth can be made without departing from the spirit and scope thereof.

EXAMPLES

Example 1

*Pseudomonas aeruginosa* Released Azurin into the Medium in the Presence of MCF-7 Cells Azurin from *Pseudomonas aeruginosa* is a periplasmic protein but is known to be secreted in the growth medium at the late stage of growth. Zaborina et al., Microbiology 146:2521-2530 (2000). Its extracellular release is dependent on quorum sensing at high cell density and modulated by GacA or the two small RNA products RsmY and RsmZ. Kay et al., J. Bacteriol. 188:6026-6033 (2006). Experiments were performed to determine if *P. aeruginosa* released azurin into the extracellular medium when contacted with cancer cells.

A mucoid isolate strain 8821 of *P. aeruginosa* from a cystic fibrosis patient and its spontaneous nonmucoid (non-alginate secreting) derivative 8822 were used as described previously by Darzins et al. (J. Bacteriol. 161:249-257 (1985)). When grown in a glucose-minimal medium supplemented with histidine, strain 8822 secreted azurin in the growth medium at the mid exponential growth phase after about 4 hours of growth. No azurin was seen in the growth medium during the lag or very early log phase of about 2 hours of growth. The mucoid strain 8821 was deficient in azurin secretion even at late log or early stationary phase. It is known that mucoid strains are deficient in extracellular protein secretion because of copious secretion of the exopolysaccharide alginate. Ohman and Chakrabarty, Infect. Immun. 37:662-669 (1982); Woods et al., J. Infect. Dis. 163:143-149 (1991).

$1.6 \times 10^4$ to $4 \times 10^5$ cells of the human breast cancer cell line MCF-7 were added to the 8821 and 8822 cells (at an optical density at 660 nm of about 0.3), grown for several hours and measured the level of azurin by Western blotting using anti-azurin antibodies in the extracellular growth medium after centrifugation of the cells and filtering the growth medium through a 0.22 μm membrane filter. Punj et al., Oncogene 23:2367-2378 (2004). A control without the MCF-7 cells but with an equivalent amount of the growth medium used.

The addition of MCF-7 cells to either mucoid strain 8821 or the nonmucoid strain 8822 had very little effect on the growth rates of the *Pseudomonas* cells (FIG. 1A, a). Most interestingly, however, the exposure to the MCF-7 cells elicited significant amounts of azurin secretion to the extracellular growth medium within 20 min (FIG. 1A, b), as determined by Western blotting (FIG. 1A, c), but only from strain 8822. No secretion of azurin was seen in absence of the MCF-7 cells (FIG. 1A, b and c) up to an hour or for several hours in the mucoid strain 8821 which is known to be deficient in extracellular protein secretion. Quantization of azurin secretion by Western blotting was done using a standard curve (FIG. 1B). Similar results were obtained with another human cancer cell line melanoma Mel-2 (data not shown). In case of both MCF-7 and Mel-2, the secretion of azurin was observed within 20 to 30 min of exposure to the cancer cells, but no secretion in absence of the cancer cells, strongly indicated that strain 8822 is capable of sensing the presence of human cancer cells and starts to secrete azurin in response to their presence.

Similar secretion, albeit delayed to 40 min or so, was seen in presence of MCF-10A cells, which are immortalized normal breast epithelial cells. The extent of azurin secretion was also dependent upon the concentrations of the cancer cells: a much higher level of azurin was seen in growth medium when $1 \times 10^8$/ml 8822 cells were exposed to $2 \times 10^6$/ml cancer cells (1.4 nM azurin) than when exposed to $1.6 \times 10^4$/ml MCF-7 cells (<0.1 nM azurin) or $8 \times 10^4$ cells/ml (0.7 nM azurin), showing a dose-dependence of azurin secretion on exposure to MCF-7 cells.

To ensure that the mucoid strain 8821 was not deficient in azurin production, the intracellular levels of azurin were also measured in both strains 8821 and 8822 (FIG. 1C) by making cellular lysates, and separating the azurin by SDS-PAGE using a fixed amount (50 μg) of the lysate protein. Both strains 8821 and 8822 demonstrated the presence of intracellular (periplasmic) azurin, although secretion was observed only from the nonmucoid cells. Quantization of azurin from the standard curve (FIG. 1B) in the intracellular and extracellular fractions of strain 8822 grown in absence (control) or in presence of MCF-7 cells demonstrated that

Example 2

MCF-7 Cells Induce Azurin Release from *P. aeruginosa* without Cell Lysis

To determine if addition of the cancer cells may induce lysis in *P. aeruginosa*, thereby releasing azurin and other proteins in the growth medium, into strain 8822 was introduced the broad host range plasmid pQF47 which harbors a functional lacZ gene encoding β-galactosidase. The release of azurin and β-galactosidase (LacZ) in the growth medium was then assessed in absence and in presence of MCF-7 cells during a 60 min period.

Figures 1, 1A, 2:
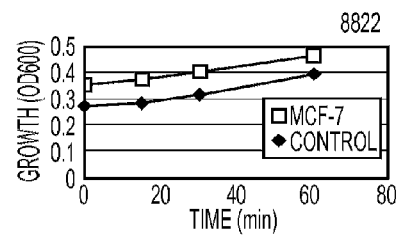
FIG. 2 depicts the lack of *P. aeruginosa* cell lysis in the presence of cancer cells.

There was no measurable release into the extracellular growth medium of LacZ either in absence (control) or in presence of MCF-7 cells during the 60 min incubation period (FIG. 2A). Examination of the cellular lysates demonstrated the presence of intracellular LacZ either in absence or in presence of cancer cells (FIG. 2A), indicating very little cellular lysis and therefore very little release of the intracellular LacZ into the external growth medium.

An examination of the presence of azurin in the growth medium, however, clearly indicated that while azurin was secreted and therefore detected in presence of MCF-7 cells, very little azurin was detected in its absence (FIG. 2B), clearly demonstrating the role of MCF-7 cells in inducing azurin secretion, but not LacZ release, from the cells. An estimation of intracellular LacZ in both strain 8822 alone and in strain 8822 harboring the pQF47 plasmid (8822/pQF47) demonstrated, as expected, that while the *P. aeruginosa* strain 8822 lacked a functional lacZ gene and therefore produced no LacZ protein, 8822/pQF47 produced significant quantities of intracellular LacZ (FIG. 2C). That the presence of azurin in the external medium is not due to lysis is also confirmed by the fact that the mucoid strain 8821, normally deficient in protein secretion, is also deficient in azurin secretion (FIG. 1A): lysis of the cells would have released azurin in its growth medium.

Concentrated filtered growth medium of MCF-7 cells was used to determine if *P. aeruginosa* strain 8822 responds to any diffusable metabolite from the cancer cells. No secretion of azurin was observed under such conditions, demonstrating that azurin secretion was contact-dependent, but energy independent for secretion. Such a mode of secretion distinguishes azurin secretion on exposure to cancer cells from other modes of protein secretion. Kostakioti et al., J. Bacteriol. 187:187:4306-4314 (2005); Thanassi et al., Mol. Membr. Biol. 22:63-72 (2005).

Example 3

MCF-7 Cells Specifically Induce the Release of Azurin from *E. coli*

Azurin is a periplasmic protein in *P. aeruginosa*. When the *P. aeruginosa* azurin gene is expressed in *Escherichia coli* JM109, the resultant azurin protein is found in the periplasm and is purified from the periplasmic fractions of *E. coli* cells. Goto et al., Mol. Microbiol. 47:549-559 (2003). Another periplasmic protein of *P. aeruginosa* is cytochrome $c_{551}$ which acts as a partner of azurin during electron transfer in vitro and which also can be purified from the periplasmic fraction of *E. coli* JCB7120 cells grown under anaerobic conditions. Id.

The secretion of azurin and cytochrome $c_{551}$ from both *P. aeruginosa* and *E. coli* strains in absence or in presence of MCF-7 cells was investigated. This investigation determined if exposure to MCF-7 breast cancer cells allows disruption of the bacterial outer membrane to release any periplasmic protein or if there is specificity in the secretion of azurin. Further, this investigation determined if azurin secretion is specific for *P. aeruginosa* or could occur from other bacteria such as *E. coli*.

Figures 1, 1A, 2, 3:
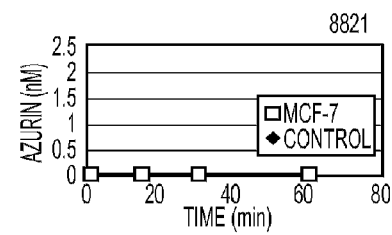
FIG. 3 depicts azurin, but not cytochrome $c_{551}$, is secreted from the periplasmic space of *E. coli* cells in response to the presence of human breast cancer MCF-7 cells in an energy-independent manner. Sample preparation was carried out as in FIG. 1. Asterisks (0*) indicate the intracellular fraction just before incubation with cancer cells. Positions of azurin and cytochrome $c_{551}$ (cyt $c_{551}$) are indicated by arrows.

The level of intracellular or extracellular cytochrome $c_{551}$ in *P. aeruginosa* 8822 under the defined conditions of aerobic growth was too low to be detectable by Western blotting. However, both azurin and cytochrome $c_{551}$ were clearly detectable in the extracts of the *E. coli* cells that hyper-expressed the proteins (FIG. 3, A and B, time 0*). Similar to *P. aeruginosa*, exposure of *E. coli* cells harboring the *P. aeruginosa* azu gene to MCF-7 cells elicited significant secretion of the azurin to the external medium, but only in presence of the cancer cells (FIG. 3A). Interestingly, however, when the *E. coli* cells harboring periplasmic cytochrome $c_{551}$ were exposed to MCF-7 cells, very little cytochrome $c_{551}$ was detected in the external growth medium (FIG. 3B), suggesting that exposure to MCF-7 cells specifically induces azurin, but not cytochrome $c_{551}$, secretion from *E. coli* even when intracellular cytochrome $c_{551}$ was clearly detectable (FIG. 3B).

Example 4

Secretion of Azurin from *P. aeruginosa* or *E. coli* is Energy-Independent

To determine if azurin secretion from either *P. aeruginosa* 8822 or *E. coli* JM109 required energy, the bacteria were incubated in presence of the protonophore carbonyl cyanide chlorophenylhdrazone (CCCP) for 1 hr at two different concentrations (50 and 250 µM for *P. aeruginosa* 8822; 250 µM for *E. coli* JM109) before exposure to the MCF-7 cancer cells. CCCP is an uncoupler of oxidative phosphorylation and inhibited bacterial growth at the concentrations used (FIG. 3E; left panel, *P. aeruginosa* 8822; right panel, *E. coli* JM109). Nevertheless, CCCP had very little effect on azurin secretion by either *P. aeruginosa* 8822 (FIG. 3C) or *E. coli* JM109 (FIG. 3D), indicating the energy-independence of azurin secretion.

Example 5

MCF-7 Cells Induced the Release of 15 kb DNA from *P. aeruginosa*

Bacterial DNA is known to be released or transferred during conjugation in response to cellular demands, using type IV secretion systems. Cascales and Christie, Nature Rev. Microbiol. 1:137-149 (2003). In such a system, direct transfer of proteins and DNA may occur in target host cells from the cytoplasm as well as from the periplasm of the donor bacteria. However, the presence of the host cells or the dependence on host cell contact is not mandatory because protein or chromosomal DNA secretion by type IV system into the growth medium in absence of any host cells has also been demonstrated. Burns, Curr. Opin. Microbiol. 2:25-29, 1999; Hamilton et al., Mol. Microbiol. 55: 1704-1721 (2005). In *P. aeruginosa*, released DNA is known to contribute to the proinflammatory processes during infection in the lungs of cystic fibrosis patients or during formation of biofilms. Delgado et al., Infect. Immun. 74: 2975-2984

(2006); Whitchurch et al., Science 295:1487 (2002). The release of any specific CpG-rich extrachromosomal DNA, however, has not been reported.

Figures 1, 1A, 2, 3, 4:
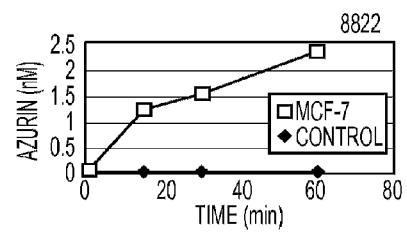
FIG. 4 depicts *Pseudomonas aeruginosa* 8822 strain secretes extrachromosomal DNA into the culture medium.

In an effort to see if *P. aeruginosa* strain 8822 might release into its growth medium not only azurin but also genomic DNA, the growth medium of strain 8822 was examined during growth for 1 or 2 hr under conditions where very little azurin was seen in absence of exposure to MCF-7 cells. To detect the presence of any nucleoprotein complex, 3 volumes of normal-isopropanol were added to the growth media followed by incubation at −80° C. for 1 hr. The nucleoprotein pellet was centrifuged, resuspended in double-distilled water and passed through the Qiagen® DNA preparation kit (Qiagen, Inc., Valencia, Calif.) before elution with double-distilled water. While there was no DNA detected at 0 h (start of the experiment), a specific band of DNA of about 15 kb size was detected at 1 and 2 h, both in absence or in presence of MCF-7 cells (FIG. 4A).

The amount of DNA was higher in presence of the cancer cells, suggesting enhanced release as is the case with azurin, but in contrast to azurin, the DNA could be detected even in the absence of the cancer cells presumably because of a much higher sensitivity for detection, using PicoGreen® (Invitrogen, Inc., Carlsbad, Calif.) and PCR reactions. Interestingly, no other significant DNA bands were seen, and this band is highly reproducible under repeated experimental conditions, suggesting that it is not a random product of chromosomal DNA digestion.

Example 6

Release Profile Suggests 15 kb DNA is Extrachromosomal

Genomic islands carrying virulence-associated genes are well-known in *P. aeruginosa*. Kiewitz et al., Microbiology 146: 2365-2373 (2000); He et al., Proc. Natl. Acad. Sci. 101:2530-2535 (2004); Klockgether et al., J. Bacteriol. 186:518-534 (2004); Kulasekara et al., J. Bacteriol. 188: 4037-4050 (2006). Biodegradative gene clusters conferring selective growth advantage in xenobiotic-contaminated environments are also known as mobile genetic elements in *Pseudomonas* species that are often associated with phage genes. van der Meer et al., Arch. Microbiol. 175:79-85 (2001). A single genomic island, PAGI-1, having at least two different DNA segments of G+C content 63.7% and 54.9% with genes involved in possible detoxification of reactive oxygen species, has been shown to be present in a number of clinical isolates of *P. aeruginosa*. Liang et al., J. Bacteriol. 185:843-853 (2001).

Similar to azurin secretion, the kinetics of the release of this DNA fragment showed its extracellular presence as early as in 5 min (FIG. 4B), even in absence of MCF-7 cells. No other DNA bands were seen under such conditions. A kinetic study of the release of azurin and the 15 kb DNA fragment in absence of any other chromosomal DNA fragment on exposure to MCF-7 cells demonstrated a similar time course of release (FIG. 4C), suggesting that the DNA is an extrachromosomal element, perhaps looping out of the chromosome as a horizontally acquired genomic island.

Example 7

15 kb DNA Release from *P. aeruginosa* is CpG-Rich DNA

In order to examine the nature of the released DNA, the DNA was subjected to various restriction endonuclease digestions. Interestingly, only MSP-1 and PvuI, which are known to cleave between G and C residues, induced extensive digestion of the DNA, indicating that the DNA is rich in G+C (FIG. 4D). When fragments of the partial digestions of these restriction enzymes, or mechanically sheared fragments, were sequenced and the homologies of the sequences were compared with those in the databases, several DNA sequences both present and absent in the *P. aeruginosa* PAO genome, were seen (FIG. 7) and SEQ ID NOS: 26-62, suggesting that the released DNA came from a genomic island in strain 8822. No plasmid DNA isolated by the usual methods of isolation has been obtained. An interesting sequence present in the CpG-rich DNA is a stretch of cytosines (FIG. 5A) and with many CpG dinucleotide sequences in it.

Example 8

The 15 kb CpG-Rich DNA Band Contains a Sequence Similar to Azurin

Figures 1, 1A, 2, 3, 4, 5:
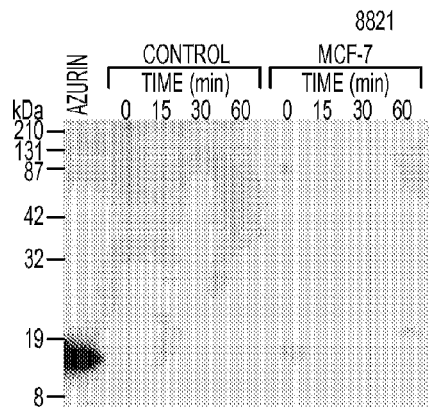
FIG. 5 depicts the DNA sequence and amino acid translation of a highly C and G-rich stretch of DNA in the released CpG-rich DNA.
Figures 1, 1A, 2, 3, 4, 5, 6:
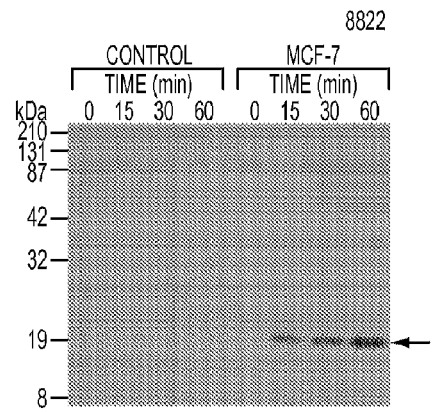
FIG. 6 depicts the induction of NF-kB by extrachromosomal CpG-rich *P. aeruginosa* DNA.
Figure 1B:
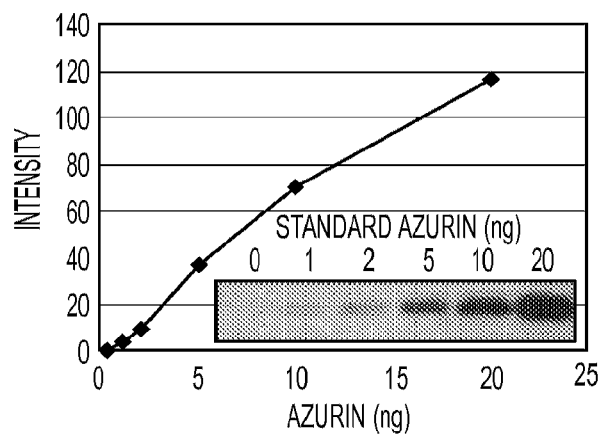
FIG. 1B. Quantitative Western blotting. The signal intensity on the Western blotting profile increases linearly with the increase of standard azurin (0 to 20 ng).
Figure 1C:
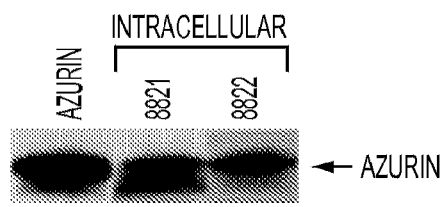
FIG. 1C. Production of azurin in *P. aeruginosa* strains 8821 and 8822. Intracellular fractions from such cells (8821, 8822) harvested at exponential growth phase were subjected to SDS-PAGE, followed by Western blotting using anti-auzrin antibody. Standard azurin is shown in the left lane.
Figure 1D:
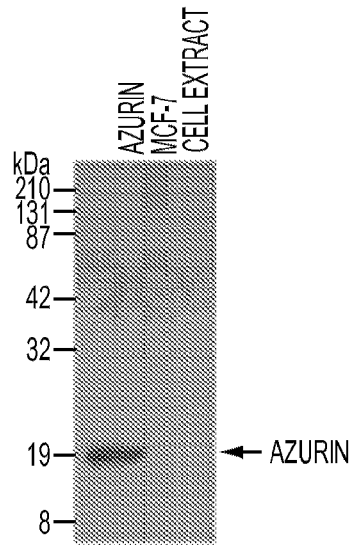
FIG. 1D. Lack of detection of azurin in MCF-7 cell extracts (100 μg protein) by Western blotting.
Figure 2:
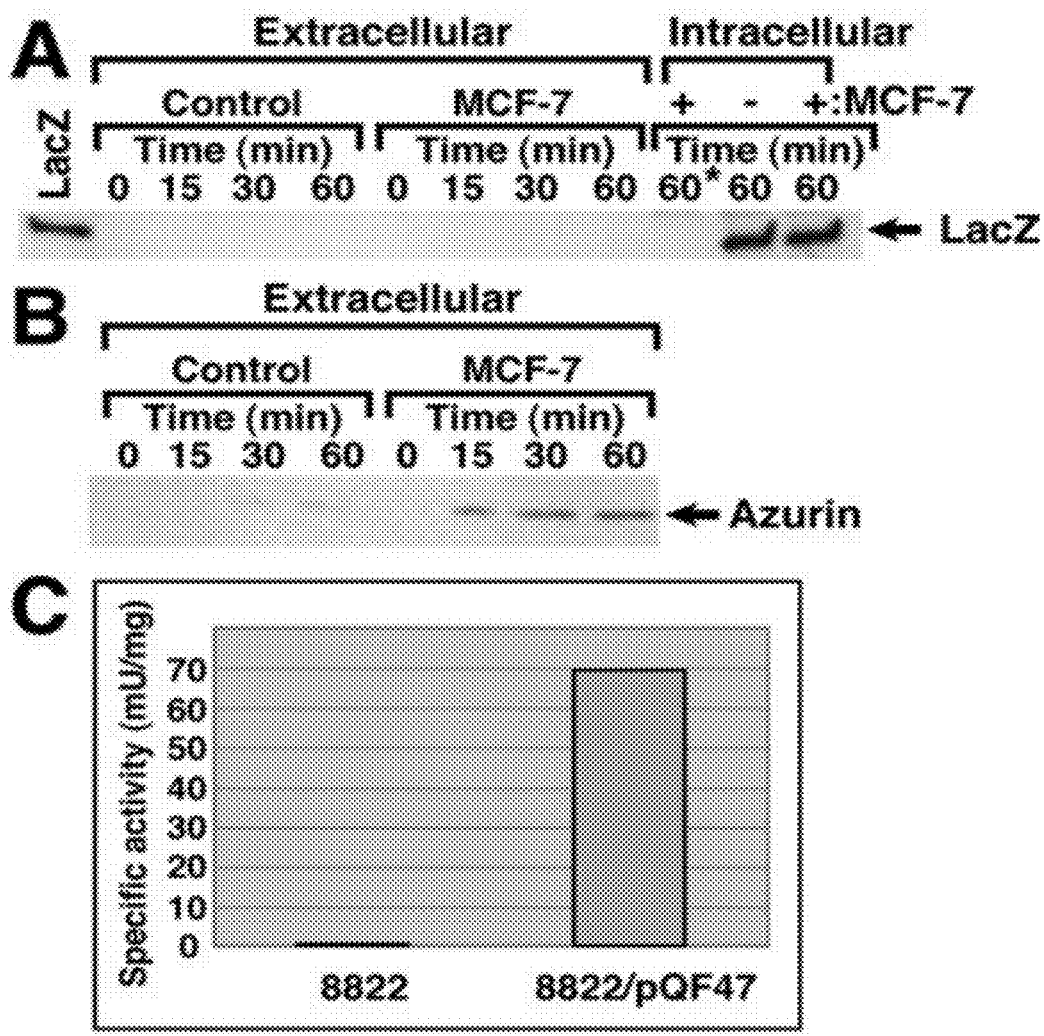
Figure 3:
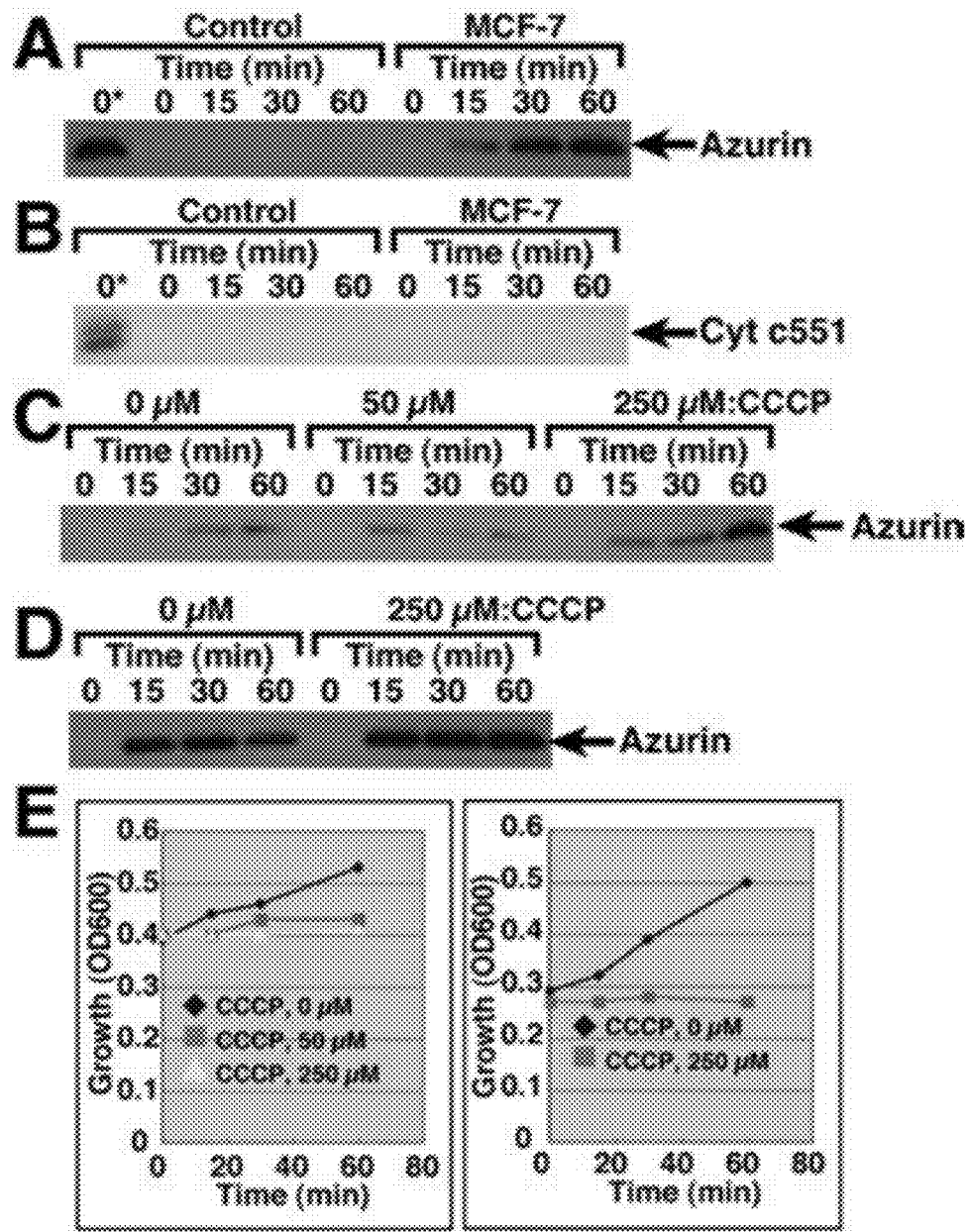
Figure 4:
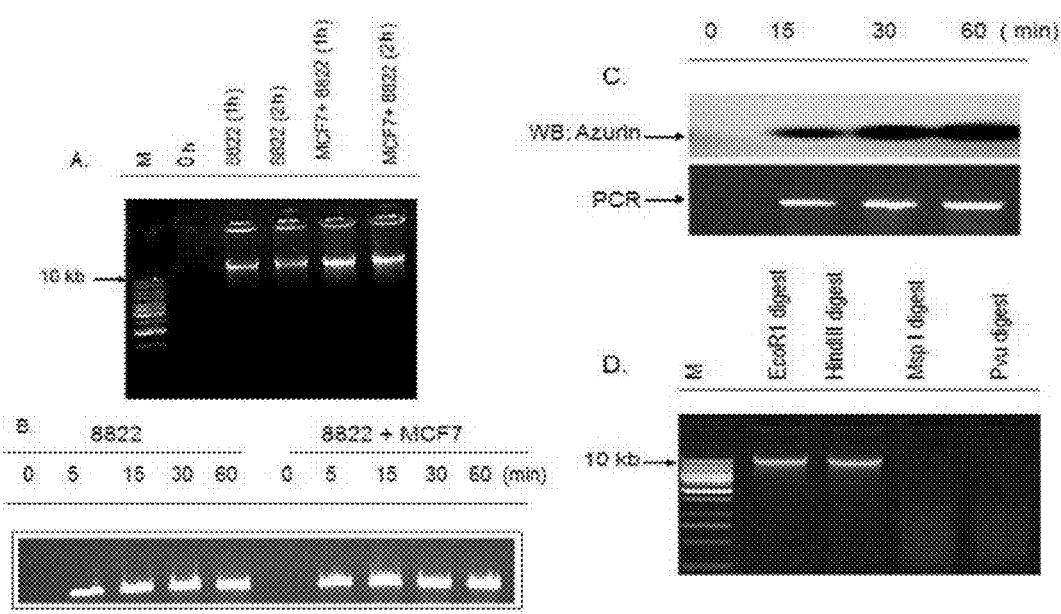

An interesting sequence present is that of the azurin gene, but resembling the azurin gene from *Neisseria* and demonstrating 95% nucleotide sequence identity with it. The amino acid sequence comparisons are shown in FIG. 5B. Since the *Neisseria*) azurin gene has an additional DNA sequence in the 5'-end, encoding the 39 amino acid H.8 epitope at the N-terminal of azurin, the CpG-rich released DNA was used as a template and both the H.8 and the azurin gene sequences were used as well as the whole gene from the *Neisseria*) H.8-azurin gene called laz. Hong et al., Cell Cycle 5:1633-1641 (2006). All three fragments could be amplified by PCR, demonstrating the presence of both the components of the *Neisseria*) laz gene in the CpG rich DNA.

Example 9

The Released CpG-Rich DNA Activates TLR9-Mediated NF-kB and has Antitumor Property CpG deoxyoligonucleotides have been reported to have antitumor properties. Krieg, Nature Med. 9:831-835 (2003); Krieg, Curr. Oncol. Rep. 6:88-95 (2004). To determine if the 15 kb CpG-rich DNA released from *P. aeruginosa* strain 8822, has properties similar to CpG synthetic oligodeoxynucleotides (ODNs), the ability of the DNA to activate NF-kB in a TLR9-dependent manner was tested. HEK293 cells, deficient in TLR9, were transfected with a TLR9-expressing plasmid. Kandimalla et al., Proc. Natl. Acad. Sci. USA 102:6925-6930 (2005). A pNIFty plasmid expressing the SEAP (secreted embryonic alkaline phosphatase) under the control of an NF-kB inducible ELAM1 composite promoter (Invitrogen, Inc., Carlsbad, Calif.) was then used. SEAP expression following NF-kB activation was measured in supernatants of transfected HEK293 cells, using the SEAP reporter assay kit (Invitrogen, Inc., Carlsbad, Calif.). The SEAP reporter assay was conducted as described by Schindler and Baichwal (Mol. Cell. Biol. 14:5820-5831 (1994)).

Figure 6A:
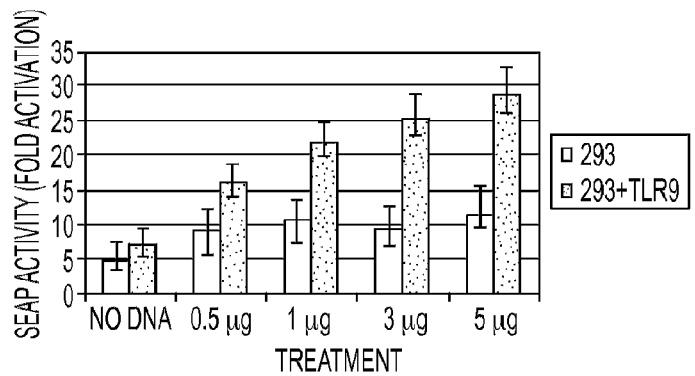
FIG. 6A, NF-kB induction is TLR9 dependent and requires the extrachromosomal CpG-rich DNA. HEK293 cells transfected with TLR9-expressing plasmid and NF-kB promoter inducible SEAP (secreted embryonic alkaline phosphatase) reporter plasmid (Invitrogen, Inc. Carlsbad, Calif.) were treated with various concentrations of CpG-rich 15 kb DNA. SEAP expression following NF-kB activation was measured in supernatants of transfected cells. SEAP levels were evaluated quantitatively using the HEK-Blue TM SEAP reporter assay kit (Invitrogen, Inc. Carlsbad, Calif.). Stimulation of HEK293 cells with CpG-rich DNA caused NF-kB induction, leading to SEAP activity in a dose dependent manner.

There was very little expression of the NF-kB-promoter inducible SEAP in the TLR9-deficient HEK293 cells (FIG. 6A). However, in TLR9-expressing-HEK293 cells, there was increasing SEAP activity with increasing amounts of the CpG-rich 15 kb DNA, suggesting that the DNA could activate the NF-kB promoter only in TLR9-proficient cells (FIG. 6A).

Figure 6B:
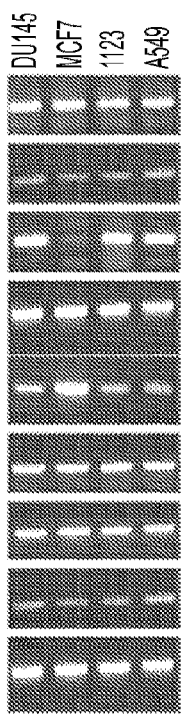
FIG. 6B, different cancer cell lines express a broad range of Toll-like receptors (TLRs). Expression of TLRs was analyzed by quantitative RT-PCR. The data are normalized to the expression of cyclophilin B.
Figure 6C:
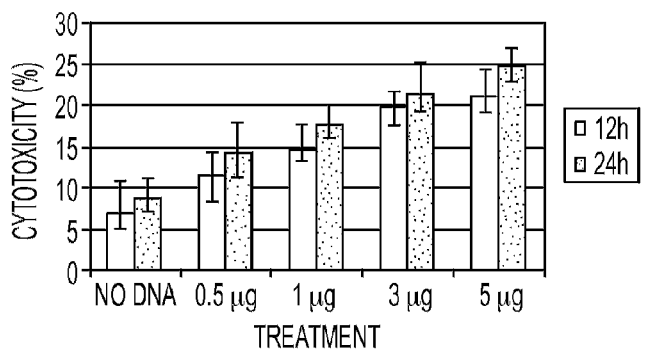
FIG. 6C, effect of CpG-rich DNA treatment on cellular proliferation of MCF-7 breast cancer cells. Cells were treated with various concentrations of the 15 kb CpG-rich DNA (0.5, 1, 3 and 5 μg) for 12 and 24 h and cell survival was determined. MTT assay was done to measure the extent of live cells to account for cytotoxicity (percent cell death) as described previously (Yamada et al., 2002). To calculate percentage cytotoxicity, the value of nontreated viable cells as 100% was used to determine the number of viable cells treated with 2.5 μg calf thymus DNA and different concentrations of the CpG-rich DNA.

To determine if the activation of TLR9-dependent NF-kB results in tumor cell death, the expression of TLR9 was measured in a range of cancer cells. Essentially all the cancer cell lines, the prostate cancer DU145, the breast cancer MCF-7 and the lung cancers H23 and A549 expressed TLR9 and other Toll-like receptors like TLR4 (FIG. 6B). When the CpG-rich DNA was incubated with the lung cancer cells A549 at increasing concentrations for 12 and 24 h, there was increasing, albeit limited, cell death, suggesting that the CpG-rich DNA had low antitumor activity (FIG. 6C).

Example 10

Efficacy Study

A double-blind, placebo controlled study will be conducted over a six-month period. A total of 80 subjects with cancer, aged 45-60 years, will be chosen for the study. Primary recruitment of subjects will occur through physician referrals. Subjects who are successfully prescreened will be contacted by telephone and invited to a screening/orientation session. Prospective subjects will be provided with a verbal and written description of the study and requirements for participation. Written informed consent will be obtained from each participant at the screening/orientation session, and medical record releases will be obtained and reviewed by the project oncologist. Participants giving consent will be assigned a study ID number. During the screening session the following information will be collected:

Demographics: Name, address, phone number, primary physician and oncologist, date of birth, race, ethnicity, occupation and years of completed education.

Medical history: Current and past medical conditions including an assessment of cancer status, medications and supplements, hospitalizations, surgery, allergies, tobacco, alcohol and illicit drug use.

Basic Physical Examination: Height, weight, blood pressure, pulse readings, and examination of the breasts, heart, lungs and abdomen.

Blood samples: Negative pregnancy test and normal liver function testing (ALT, AST) and hemoglobin.

The 80 subjects will be separated into 2 separate groups of 40 subjects. The first group will be administered one dosage form comprising SEQ ID NO: 26 and a pharmaceutically acceptable carrier once a day. The second group will be administered one dosage form of placebo once a day. Body weight and tumor volume (including tumor progression, stasis, regression and multiplicity) will be monitored every 3 days during the treatment period. The following tumor volume categories will be used for scoring: Progression: the tumor grows more than 40% in area compared to commencement of treatment; Stasis: the tumor did not fluctuate more than 40% from its initial area throughout the course of treatment; Regression: the tumor regressed more than 40% from its initial area; Multiplicity: appearance of new tumors during the treatment.

Body Weight. There will be an observable difference in body weight between the subjects receiving SEQ ID NO: 26 and a pharmaceutically acceptable carrier versus placebo. Those receiving SEQ ID NO: 26 and a pharmaceutically acceptable carrier will, on average, weigh more than those receiving placebo when height and sex is controlled for.

Tumor Volume. At the beginning of treatment, tumor sizes in both groups will be comparable and not significantly different from each other. On average, the tumor volume of placebo subjects will increase at a variable rate. Subjects receiving SEQ ID NO: 26 and a pharmaceutically acceptable carrier will show reduced growth in tumor size when compared to placebo treated subjects.

Tumor Progression. The percent of tumors that progress will be calculated as described above. Subjects receiving SEQ ID NO: 26 and a pharmaceutically acceptable carrier will demonstrate less tumor progression over the course of the study than subjects receiving placebo.

Tumor Stasis. The percent of tumors that remain in stasis will be calculated as described above. Subjects receiving SEQ ID NO: 26 and a pharmaceutically acceptable carrier will demonstrate more tumor stasis as compared to tumor growth than subjects receiving placebo.

Tumor Regression. The percent of tumors that regress will be calculated as described above. Subjects receiving SEQ ID NO: 26 and a pharmaceutically acceptable carrier will demonstrate more tumor regression than subjects receiving placebo.

Tumor Multiplicity. The percent of tumors that multiply will be determined as described above. Subjects receiving SEQ ID NO: 26 and a pharmaceutically acceptable carrier will demonstrate less tumor multiplicity than subjects receiving placebo.

Although the illustrated embodiments of the present invention have been described herein with reference to the accompanying drawings, it is understood that the invention is not limited to those precise embodiments and that various other changes and modifications may be effected thereon by one skilled in the art without departing from the scope or spirit of the invention, and that it is intended to claim all such changes and modifications as fall within the scope of the invention.

What is claimed is:

1. A pharmaceutical composition comprising:
   a polynucleotide comprising a sequence selected from the group consisting of: SEQ ID NOS: 36, 38-41 and 43-45, wherein the polynucleotide has been stabilized by condensation or spray-dried to produce a particulate form in one or a combination of shapes selected from the group consisting of spherical, rod and toroid; and
   a pharmaceutically acceptable carrier;
   wherein the polynucleotide remains in the particulate form in the pharmaceutically acceptable carrier.

2. The pharmaceutical composition of claim 1 which additionally comprises at least one cupredoxin peptide.

3. The pharmaceutical composition of claim 1, wherein the pharmaceutical composition is formulated for intravenous administration.

4. The pharmaceutical composition of claim 1, wherein the pharmaceutical composition is formulated for subcutaneous administration.

5. The pharmaceutical composition of claim 1, wherein the pharmaceutical composition is formulated for topical administration.

6. The pharmaceutical composition of claim 1, wherein the particulate form has a size in the range of about 20 nm to about 500 nm.

7. The pharmaceutical composition of claim 1, wherein the particulate form is hollow.

8. The pharmaceutical composition of claim 1, wherein the particulate form is solid.

* * * * *